(12) United States Patent
Krueger

(10) Patent No.: US 11,389,059 B2
(45) Date of Patent: *Jul. 19, 2022

(54) OCULAR-PERFORMANCE-BASED HEAD IMPACT MEASUREMENT USING A FACEGUARD

(71) Applicant: Wesley W. O. Krueger, San Antonio, TX (US)

(72) Inventor: Wesley W. O. Krueger, San Antonio, TX (US)

( * ) Notice: Subject to any disclaimer, the term of this patent is extended or adjusted under 35 U.S.C. 154(b) by 275 days.

This patent is subject to a terminal disclaimer.

(21) Appl. No.: 16/805,253

(22) Filed: Feb. 28, 2020

(65) Prior Publication Data

US 2020/0214559 A1    Jul. 9, 2020

Related U.S. Application Data

(63) Continuation-in-part of application No. 16/351,326, filed on Mar. 12, 2019, now Pat. No. 10,602,927, which is a continuation-in-part of application No. 16/264,242, filed on Jan. 31, 2019, now Pat. No. 10,716,469, which is a continuation-in-part of application No. 15/713,418, filed on Sep. 22, 2017, (Continued)

(51) Int. Cl.
| | |
|---|---|
| *A61B 3/113* | (2006.01) |
| *A42B 3/04* | (2006.01) |
| *A61B 5/00* | (2006.01) |
| *G02B 27/00* | (2006.01) |
| *G02B 27/01* | (2006.01) |

(52) U.S. Cl.
CPC .............. *A61B 3/113* (2013.01); *A42B 3/046* (2013.01); *A61B 5/4064* (2013.01); *A61B 5/6821* (2013.01); *G02B 27/0093* (2013.01); *G02B 2027/0187* (2013.01)

(58) Field of Classification Search
CPC ..... A63B 71/10; A61B 5/6803; A61B 5/1121; A61B 3/113; A61B 3/112; A61B 3/028; A61B 3/18; A42B 3/20; A42B 3/0433
USPC ................ 351/200, 203, 205, 206, 210, 246
See application file for complete search history.

(56) References Cited

U.S. PATENT DOCUMENTS

| | | |
|---|---|---|
| 3,616,463 A | 11/1971 | Theodore et al. |
| 4,817,633 A | 4/1989 | McStravick et al. |

(Continued)

FOREIGN PATENT DOCUMENTS

WO    2013-117727    8/2013

OTHER PUBLICATIONS

Allison, et al. "Combined Head and Eye Tracking System for Dynamic Testing of the Vestibular System" IEEE Transactions on Biomedical Engineering, vol. 43, No. 11, Nov. 1996, all pages.

(Continued)

*Primary Examiner* — James R Greece

(57) ABSTRACT

A faceguard is configured for measuring a human eye muscle movement response. The faceguard is configured for protecting at least one part of a human face and has an aperture for human vision through the faceguard. The faceguard comprises an eye sensor, a head orientation sensor, and an electronic circuit. The eye sensor comprises a video camera and is configured for measuring eyeball movement, pupil size, and/or eyelid movement. The head orientation sensor senses pitch and/or yaw of a person's head. The electronic circuit is responsive to the eye sensor and the head orientation sensor.

20 Claims, 11 Drawing Sheets

Related U.S. Application Data now Pat. No. 10,231,614, which is a continuation-in-part of application No. 15/162,300, filed on May 23, 2016, now Pat. No. 9,788,714, which is a continuation-in-part of application No. 14/326,335, filed on Jul. 8, 2014, now Pat. No. 9,370,302, said application No. 16/264,242 is a continuation-in-part of application No. 13/749,873, filed on Jan. 25, 2013, now abandoned.

(56) References Cited

U.S. PATENT DOCUMENTS

| | | |
|---|---|---|
| 5,180,907 A | 1/1993 | Udden et al. |
| 5,204,998 A | 4/1993 | Liu |
| 5,550,601 A | 8/1996 | Donaldson |
| 5,553,330 A * | 9/1996 | Carveth .............. A42B 3/0473 2/414 |
| 5,555,895 A | 9/1996 | Ulmer et al. |
| 5,621,922 A | 4/1997 | Rush, III |
| 5,838,420 A | 11/1998 | MacGregor Donaldson |
| 5,919,149 A | 7/1999 | Allum |
| 5,942,954 A | 8/1999 | Galiana et al. |
| 5,953,102 A | 9/1999 | Berry |
| 5,978,972 A | 11/1999 | Stewart et al. |
| 6,301,718 B1 | 10/2001 | Rigal |
| 6,796,947 B2 | 9/2004 | Watt et al. |
| 6,826,509 B2 | 11/2004 | Crisco et al. |
| 6,931,671 B2 | 8/2005 | Skiba |
| 7,276,458 B2 | 10/2007 | Wen |
| 7,380,938 B2 | 6/2008 | Chmielewski et al. |
| 7,386,401 B2 | 6/2008 | Vock et al. |
| 7,401,920 B1 | 7/2008 | Kranz et al. |
| 7,448,751 B2 | 11/2008 | Kiderman et al. |
| 7,500,752 B2 | 3/2009 | Nashner |
| 7,509,835 B2 | 3/2009 | Beck |
| 7,526,389 B2 | 4/2009 | Greenwald et al. |
| 7,651,224 B2 | 1/2010 | Wood et al. |
| 7,682,024 B2 | 3/2010 | Plant et al. |
| 7,727,162 B2 | 6/2010 | Peterka |
| 7,731,360 B2 | 6/2010 | MacDougall et al. |
| 7,753,523 B2 | 7/2010 | Kiderman et al. |
| 7,849,524 B1 | 12/2010 | Williamson et al. |
| 7,866,818 B2 | 1/2011 | Schroeder et al. |
| 7,931,370 B2 | 4/2011 | Bartomeu |
| 7,988,287 B1 | 8/2011 | Butler et al. |
| 8,232,881 B2 | 7/2012 | Hertz |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 8,578,520 B2 | 11/2013 | Haldin |
| 8,696,126 B2 | 4/2014 | Yoo et al. |
| 8,764,193 B2 | 7/2014 | Kiderman et al. |
| 9,370,302 B2 | 6/2016 | Krueger |
| 9,788,714 B2 | 10/2017 | Krueger |
| 2002/0118339 A1 | 8/2002 | Lowe |
| 2006/0059606 A1 | 3/2006 | Ferrara |
| 2006/0098087 A1 | 5/2006 | Brandt et al. |
| 2006/0206175 A1 | 9/2006 | Tournier et al. |
| 2006/0270945 A1 | 11/2006 | Ghajar |
| 2008/0022441 A1 | 1/2008 | Oranchak et al. |
| 2009/0021695 A1 | 1/2009 | Scarpino |
| 2010/0036289 A1 | 2/2010 | White et al. |
| 2010/0092049 A1 | 4/2010 | Schroeder et al. |
| 2010/0101005 A1 | 4/2010 | Cripton et al. |
| 2010/0198104 A1 | 8/2010 | Schubert et al. |
| 2010/0280372 A1 | 11/2010 | Poolman et al. |
| 2011/0176106 A1 | 7/2011 | Lewkowski |
| 2011/0209272 A1 * | 9/2011 | Drake .............. A42B 3/20 2/411 |
| 2012/0133892 A1 | 5/2012 | Furman et al. |
| 2012/0143526 A1 | 6/2012 | Benzel et al. |
| 2012/0198604 A1 | 8/2012 | Weber et al. |
| 2012/0204327 A1 | 8/2012 | Faden et al. |
| 2012/0297526 A1 | 11/2012 | Leon |
| 2013/0232668 A1 | 9/2013 | Suddaby |
| 2013/0278899 A1 | 10/2013 | Waldorf et al. |
| 2014/0111771 A1 | 4/2014 | Liu |
| 2014/0192326 A1 | 7/2014 | Kiderman et al. |
| 2014/0327880 A1 | 11/2014 | Kiderman et al. |
| 2015/0038803 A1 | 2/2015 | Uhlig et al. |
| 2015/0212576 A1 | 7/2015 | Ambrus et al. |
| 2015/0223683 A1 | 8/2015 | Davidovics et al. |
| 2015/0243099 A1 | 8/2015 | Schowengerdt |
| 2015/0245766 A1 | 9/2015 | Rennaker et al. |
| 2015/0335239 A1 | 11/2015 | Macfougall |
| 2016/0033750 A1 | 2/2016 | Nunnink et al. |
| 2016/0062459 A1 | 3/2016 | Publicover et al. |
| 2016/0081546 A1 | 3/2016 | MacDougall et al. |
| 2016/0085302 A1 | 3/2016 | Publicover et al. |
| 2016/0106315 A1 | 4/2016 | Kempinski |
| 2016/0110920 A1 | 4/2016 | Schowengerdt |
| 2016/0132726 A1 | 5/2016 | Kempinski et al. |
| 2016/0242642 A1 | 8/2016 | Migliaccio et al. |

OTHER PUBLICATIONS

Foster, "New Football Helmet Could Save the Sport", published by Popular Science, https://www.popsci.com/science/article/2013-08/helmet-wars-and-new-helmet-could-protect-us-all, Dec. 18, 2012, all pages.

* cited by examiner

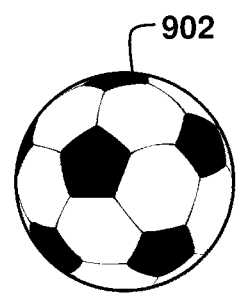
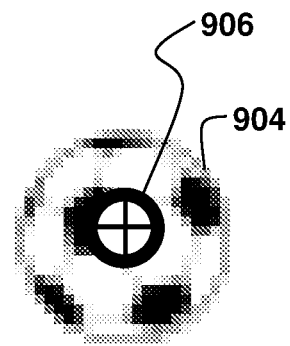
FIG. 7A          FIG. 7B
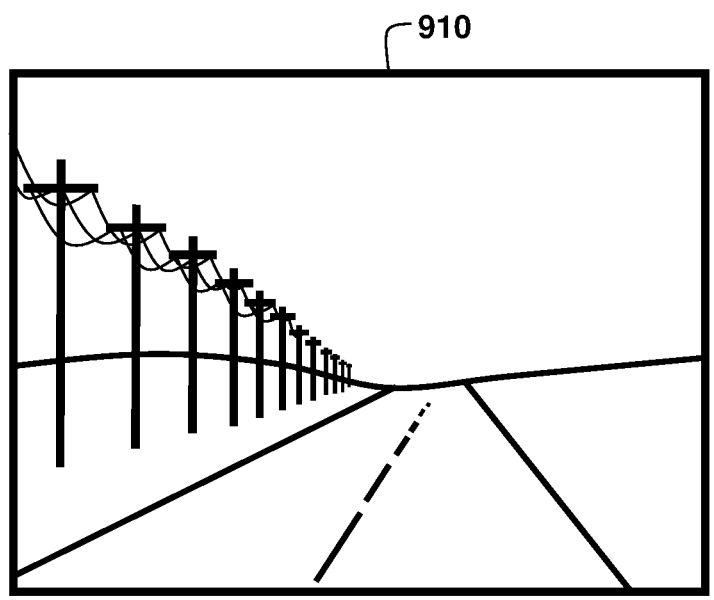
FIG. 8

US 11,389,059 B2

OCULAR-PERFORMANCE-BASED HEAD IMPACT MEASUREMENT USING A FACEGUARD

CROSS REFERENCE TO RELATED APPLICATIONS

This application is a Continuation-in-Part of U.S. patent application Ser. No. 16/351,326 filed 12 Mar. 2019, which is a Continuation-in-Part of U.S. patent application Ser. No. 16/264,242 filed 31 Jan. 2019. U.S. patent application Ser. No. 16/264,242 is a Continuation-in-Part of U.S. patent application Ser. No. 15/713,418 filed 22 Sep. 2017, which is a Continuation-in-Part of U.S. patent application Ser. No. 15/162,300 filed 23 May 2016, which is a Continuation-in-Part of U.S. patent application Ser. No. 14/326,335 filed 8 Jul. 2014. U.S. patent application Ser. No. 16/264,242 is also a Continuation-in-Part of U.S. patent application Ser. No. 13/749,873 filed 25 Jan. 2013. The entire disclosures of all of the aforementioned patents and applications are incorporated by reference herein.

FIELD OF INVENTION

Embodiments of the invention(s) disclosed herein relate to systems and methods that use human ocular performance measurement in combination with a face guard. Human ocular performance can be measured using vestibulo-ocular reflex, ocular saccades, pupillometry, visual pursuit tracking, vergence, eye-lid closure, focused position of the eyes, dynamic visual acuity, kinetic visual acuity, virtual retinal stability, retinal image stability, foveal fixation stability and nystagmus.

BACKGROUND

Concussions are a type of traumatic brain injury (TBI) that is sometimes called a mild traumatic brain injury or a moderate traumatic brain injury and abbreviated as an MTBI. Concussions and the resultant chronic traumatic encephalopathy (CTE) have reached epidemic proportions in the US. The CDC estimates that as many as 3.8 million sports-related concussions occur in the U.S. each year including professional athletes, amateurs of all levels, and children. There are over 250,000 emergency room visits of young people annually for head injuries from sports and recreation activities. Over 50 million Americans participate in team sports and all of them are at some level of risk of experiencing a concussion. Concussions from multiple head blows and the resulting CTE have caused several professional football players to commit suicides. The US National Football League (NFL) and the scientific community recognize that concussions are a major concern for both players and the sport itself. Concussions also occur in college and high school football, in other sports such as ice hockey and cycling, and in military operations.

Concussions happen in the brain's white matter when forces transmitted from a big blow strain nerve cells and their connections, the axons, resulting in changes to the brain such as pruning, synaptic pruning, and myelination. Linear blunt trauma can happen when falling to the ground and hitting the back of the head. The falling motion propels the brain in a straight line downward. Rotational blunt trauma can occur when a player is spun, rolled or turned with the head hitting the object. The base of the skull is rough with many internal protuberances. These ridges can cause trauma to the temporal lobes during rapid deceleration.

There is a predicted intracranial pressure wave after a concussive blow with the positive pressure (coup) to negative pressure (contre-coup) occurring across the brain. A high sheer stress occurs in the central core of the brain (e.g. brainstem). Axonal injury occurs with degeneration/disintegration in discrete regions of the brain. Axon retraction and areas of hemorrhage are noted.

Diffuse axonal injury (DAD occurs from rotational forces. The injury to tissue is greatest in areas where the density difference is greatest. For this reason, almost ⅔ of DAI lesions occur at the gray-white matter junction. Location of injury depends on plane of rotation. The magnitude of injury depends on the distance from the center of rotation, arc of rotation, duration and intensity of the force. There are widespread metabolic changes (reduced N-Acetylaspartate (NAA)/Creatine (Cr), increased Choline (Cho)/Cr, and reduced NAA/Cho ratios). Early and late clinical symptoms, including impairments of memory and attention, headache, and alteration of mental status, are the result of neuronal dysfunction. The mechanical insult initiates a complex cascade of metabolic events. Starting from neurotoxicity, energetic metabolism disturbance caused by the initial mitochondrial dysfunction seems to be the main biochemical explanation for most post-concussive signs and symptoms. Furthermore, concussed cells enter a peculiar state of vulnerability, and if a second concussion is sustained while they are in this state, they may be irreversibly damaged by the occurrence of swelling. This condition of concussion-induced brain vulnerability is the basic pathophysiology of the second impact syndrome.

Prior Art Non-Ocular Concussion Assessment Methods and Systems

Current methods concussion assessment methods and systems are inadequate. The techniques used include: (a) questioning the athlete or person about the incident; (b) a sideline test with brief neurologic exam and follow up with a clinician; and (c) transferring the patient to medical facility to perform an emergency CT or MRI scan of the head.

Following a witnessed or reported traumatic force to the head, athletes are typically evaluated on the sideline or locker room with interrogation regarding relevant symptoms. More common symptoms include headache, dizziness, difficulty with concentration, confusion and visual disturbance or photosensitivity. Many also experience nausea, drowsiness, amnesia, irritability or feeling dazed. However, none of these symptoms either alone or in combination, are specific for concussion, and frequently concussions can be undetectable by symptom screening alone. Such a sideline evaluation is suboptimal. More specific testing is not readily available for most individuals and a delayed evaluation is the norm. For those seen later by clinicians, the neurologic exam is often normal. While CT scans are effective in detecting acute brain trauma such as hematoma or edema, they are limited in detecting concussions and other concussion-related symptoms because concussions affect brain function rather than structure. Thus, functional tools, such as functional MRIs (fMRIs) need to be used.

A fMRI is a concussion diagnostic tool used by medical professionals to measure the difference between the magnetic states of oxygen-rich and oxygen-poor blood through the use of blood-oxygen-level-dependent (BOLD) contrast techniques. These scans may not be readily available at most hospitals and the use is limited.

Further, specific clinical laboratory tests with professional specialists to interpret the data are not immediately available or even accessible to some players. There are presently some tests available for concussion assessment. Both balance and gait can also be affected in the setting of concussion, and numerous sideline assessments are intended to evaluate these sensorimotor functions.

The Standardized Assessment of Concussion (SAC) is a brief cognitive test that specifically evaluates orientation, concentration, and memory. While the test is easy to administer as a sideline screening tool, it suffers from inadequate sensitivity to justify its use as a stand-alone test. Furthermore, as with symptom checklists, determined athletes can manipulate the outcome, either by memorizing certain portions of the evaluation or by intentionally underperforming in the preseason baseline assessment to which subsequent tests will be compared. It lacks validity and reliability of the data obtained.

The Balance Error Scoring System (BESS) is a static balance assessment that requires an individual to perform 3 stances on 2 different surfaces for a total of 6 trials. Each trial is 20 seconds in duration, and the score is equal to the cumulative number of balance errors. While balance itself is a relatively objective measure of sensorimotor function, significant variability in scoring is reflected by poor inter-rater and even intrarater reliability. An individual's score on the BESS can also fluctuate during the course of an athletic season independent of concussion status, and the BESS score can be further confounded by lower-extremity injuries and/or fatigue.

The timed tandem gait test (TGT) is a dynamic assessment of sensorimotor function in which a participant is timed while walking heel-to-toe along a 38-mm-wide piece of tape that is 3 m in length. Each assessment consists of 4 identical trials, and the best time among the 4 trials is recorded as the official score. Timed TGT performance can be affected by exercise and lacks specificity for concussions and reliability.

The Sport Concussion Assessment Tool, 3rd Edition (SCAT-3) consists of a carefully selected series of tests, including a focused physical exam, a 22-symptom checklist, the GCS, and cognitive and sensorimotor assessments. The SCAT-3 benefits from its ability to assess a range of neurological functions, including orientation, cognition, memory, balance, and gait. However, the duration of the test battery is approximately 15-20 minutes, which is not optimal in the setting of time-limited athletic competition. Furthermore, the SCAT-3 is designed to be administered by medical practitioners, which limits its utility in youth and high-school sports, in which medical professionals are not necessarily available for sideline concussion screening. Similar to many of the other concussion screening tools, the SCAT-3 also requires baseline testing for comparison, which carries additional logistical challenges. Finally, SCAT-3 is not 100% sensitive for identifying athletes with concussion and is more of a complementary test rather than the primary stand-alone tool for concussion detection. The checklist's sensitivity has been shown to have a significant degree of variability. A revised SCAT-5 incorporates cognitive and balance testing with 6 pages of forms to complete and takes more than 10 minutes to complete. This test also cannot be used as stand-alone method to diagnose concussion.

The King-Devick Test (KDT) is a rapid mobile application of visual performance measure. It takes about two minutes to complete and compares pre-test results. This is a rapid number-naming task requiring the athlete to read aloud 3 cards of irregularly spaced single-digit numbers as quickly as possible. Scoring is based on both speed and accuracy. This test does not measure eye movements such as vergence or other oculomotor parameters, such as VOR or visual pursuit. This test also cannot measure fine ocular movements such as saccades. At its core, the KDT is an assessment of visual function, but it also assesses the integrity of attention. The KDT requires a baseline assessment for comparison. In the setting of sideline concussion screening, the KDT is ideal in that it takes less than 1-2 minutes to complete but is 80%-86% sensitive for detecting concussion and thus should not be used as a stand-alone test and has testing reliability variability due to large learning effect.

Brain Scope uses commercial smartphone hardware, using an Android operating system and a custom sensor to record and analyze a patient's electroencephalogram (EEG) after head, injury. The test is based on a technique called quantitative electroencephalography, or QEEG. QEEG relies on computerized analysis of a set of changes that are distinctive of a traumatic brain injury. It requires a baseline measurement because without a baseline measurement it can't be known for sure whether someone's EEG signal is in fact abnormal. The difference could be other things besides concussion, like a medication, a previous head injury, or something else entirely. It also requires trained personnel for interpretation and is not completely portable. It has not been well accepted, is more difficult to interpret and is more time consuming.

A blood test, called the Brain Trauma Indicator (BTI), helps determine whether a CT scan is needed in people with suspected concussion. The test measures two brain-specific proteins, ubiquitin C-terminal hydrolase (UCH-L1) and glial fibrillary acidic protein (GFAP), that are rapidly released by the brain into the blood within 12 hours of serious brain injury. Test results can be available within three to four hours (or approximately 16 hours after the serious injury). Low blood levels of these proteins indicate that, if the person has damage, it is likely too small to be seen on a CT scan. Obviously, this cannot be done acutely, but has to be done in a medical facility, which may not be readily available for remote injuries. Failure to provide information immediately, may also fail to prevent second events, as the athlete or military personnel may have returned to play or previous activities.

ImPACT (Immediate Post-Concussion Assessment and Cognitive Testing) is a neurocognitive assessment administered online in a controlled environment. ImPACT has two components: baseline testing and post-injury testing, which are used in conjunction to determine if a patient can safely return to an activity. ImPACT testing is a 25 to 30-minute online test. ImPACT is designed for ages 12-59. Only licensed healthcare providers can administer and interpret post-injury test results and this is not available in most cities. It therefore cannot test the individual acutely and reliability is poor.

Helmet Instrumented Telemetry (HITS), that measures the magnitude and direction of an impact to a helmet is now used in some helmets, but do not appear to be reliable predictor of concussion or concussion severity.

Prior Art Ocular Concussion Assessment Methods

The ability to track objects in the environment is an important feature for humans to interact with their surroundings. In particular, the ability to recognize the presence of an environmental hazard is directly linked to our ability to fix our gaze on a visualized target of interest, recognize the threat, and implement a plan of action. Therefore, the central nervous system (CNS) is imposed with a series of tasks and time constraints that require a harmonic integration of several neural centers located in multiple regions and linked through an efficient transmission of information. There are central nervous system (CNS) impairments in individuals with mTBIs long after the last traumatic episode. Even a mild TBI (mTBI), also known as a concussion, will result in oculomotor abnormalities and can cause visual problems, including, but not limited to dysfunction with visual fixation on a visual element or visual object of interest and vergence. In addition to glare and photophobia, individuals commonly report problems including blurred vision; squinting; double vision/diplopia; difficulty reading; watching television; using computers; loss of visual acuity; color discrimination; brightness detection; contrast sensitivity; visual field defects; visuospatial attention deficits; slower response to visual cues; visual midline shift syndrome, affecting balance and posture; impaired accommodation and convergence; nystagmus; visual pursuit disorders; deficits in the saccadic system; extraocular motility problems resulting in strabismus; reduction in stereopsis; reading problems, including losing one's place, skipping lines, and slow reading speed.

During periods of fixation, our eyes are never perfectly stable but display small involuntary physiological eye movements. These take the form of disconjugate slow drifts) (1-3'/~0.05°, small conjugate microsaccades (5-10'/~0.17°, 1-2 per second) and disconjugate tremors (15"/0.004°; 30-80 Hz) superimposed on the slow drifts. A further class of involuntary physiological eye movement is called saccadic intrusions (SI). They are conjugate, horizontal saccadic movements which tend to be 3-4 times larger than the physiological microsaccades and take the form of an initial fast eye movement away from the desired eye position, followed, after a variable duration, by either a return saccade or a drift. Saccadic intrusions are involuntary, conjugate movements which take the form of an initial fast movement away from the desired eye position and followed after a short duration, by either a return secondary saccade or a drift.

When analyzing eye movement accuracy, abnormal saccadic eye movements while performing smooth pursuit, diminished accuracy of primary saccadic eye movement, and a widespread slower reaction to visual stimuli can all be seen. More commonly the most relevant saccadic parameters measured are peak velocity, latency, and accuracy. Visually guided saccadic tasks showed longer latencies and reduced accuracy irrespective of the severity of TBI. There is also increased eye position error, variability, widespread delays in reaction times and significant adaptations to normal patterns of eye tracking movements. Saccadic intrusions (irregular episodic occurrences of fast eye movements) are classified according to whether or not the intrusive saccades are separated by a brief interval in which the eyes are stationary. Although saccadic reaction times appear delayed in mild TBI, they can be seen to resume to normal levels one to three weeks after injury.

Saccadic intrusions, and saccadic oscillations are fixation instabilities which impair vision, and usually are involuntary and rhythmic. Saccadic oscillations are caused by abnormalities in the saccadic eye movement system. Abnormal saccades move the eyes away from the intended direction of gaze, and corrective saccades carry the eyes back. In saccadic intrusions, such as square-wave jerks and macrosquare-wave jerks, brief pauses occur, or intersaccadic intervals, between the opposing saccades. In ocular flutter and opsoclonus, no intersaccadic intervals occur. Three of four types of SI monophasic square wave intrusions (MSWI), biphasic square wave intrusions (BSWI) and double saccadic pulses (DSP) have been noted to be exclusively saccadic, while the fourth type, the single saccadic pulses (SSP), exhibits a slow secondary component. Following mTBI the impaired ability to generate predictive (or anticipatory saccades) can also be seen. The majority of individuals have vergence system abnormalities (convergence insufficiency), which typically results in oculomotor symptoms related to reading.

Thus, the measurement of ocular performance or eye movement responses can greatly enhance the ability to determine whether a traumatic brain injury has occurred. However, the currently available ocular performance technology is not optimized for concussion evaluation.

The EYE-SYNC System quantifies the predictive timing of dynamic visuo-motor synchronization (DVS) between gaze and target during predictive circular visual tracking. Eye-Sync utilizes a head worn goggles which measures smooth pursuit, while the head remains motionless. The test takes 1 minute, while the user visualizes a dot moving in a circle. Eye trackers measures spatial and timing variability and has 80% test reliability for detecting concussions. However, visual pursuit testing cannot test the vestibular system, which is also intimately related to concussions. It therefore lacks more sophisticated testing, such as seen with vestibular ocular reflex testing. It is also not a stand-alone device, but requires an accessory computer attached.

The Eye-Guide Focus system features an eye-tracking headset and a portable chin mount. Its software runs on an iPad facing the user and the user has to follow a small white circle moving across the screen with their eyes in order to set the baseline of how their eyes normally function. This system lacks complete portability and uses similar technology to Eye-Sync.

Neuro Kinetics I-PAS System is a battery of tests using goggles and measures ocular motor, eye motor and reaction times to test whether certain neural pathways have been altered or are behaving abnormally. I-Pass test subjects wear a pair of goggles linked to a laptop and allows the tester to measure infinitesimally small changes in the subject's eye muscles while the test is taking place. The data generated from the test, coupled with the clinical exam, allows the doctor to make a final diagnosis. (a non-portable device). This testing is performed in a clinical environment, lacks portability and multiple pieces of equipment, with medical personnel, are required to interpret the data obtained.

Oculogica's EyeBOX uses ocular motility to detect cranial nerve function and provides a BOX Score indicative of the presence and severity of brain injury. The EyeBOX requires no pre-test calibration which can omit critical information if the subject being evaluated has indeed suffered a TBI or concussion. This test requires the user to rest their chin and forehead comfortably on the device and watch a video for less than four minutes. This requires laboratory testing and also lacks portability.

The evidence shows that more sophisticated testing is needed which is highly specific for concussion detection, portable and can be used on the field of play, in a military operative environment or in any other environment where a concussion is likely to occur. Specifically, oculomotor parameter measurement as described with this invention using ocular and head sensing elements and transducers have shown high sensitivity and accuracy in identifying athletes who experienced a sport-related concussion. When comparing all these tests, the VOR has the highest percentage for identifying the individual with concussions.

CONCLUDING SUMMARY

It is desired to provide a head impact measurement and mitigation system and/or method that is fundamentally superior to the prior art in determining whether a concussion has occurred and in reducing the chance of one or more concussions that can lead to chronic traumatic encephalopathy.

BRIEF DESCRIPTION OF THE DRAWINGS

The present invention will be better understood on reading the following detailed description of non-limiting embodiments thereof, and on examining the accompanying drawings, in which:

FIG. 7A shows an unaltered visual element;

FIG. 7B shows the visual element of FIG. 7A that has been altered by defocusing the visual element and superimposing a target;

FIG. 8 shows a scene that can be used for optokinetic testing;

Figure 1:
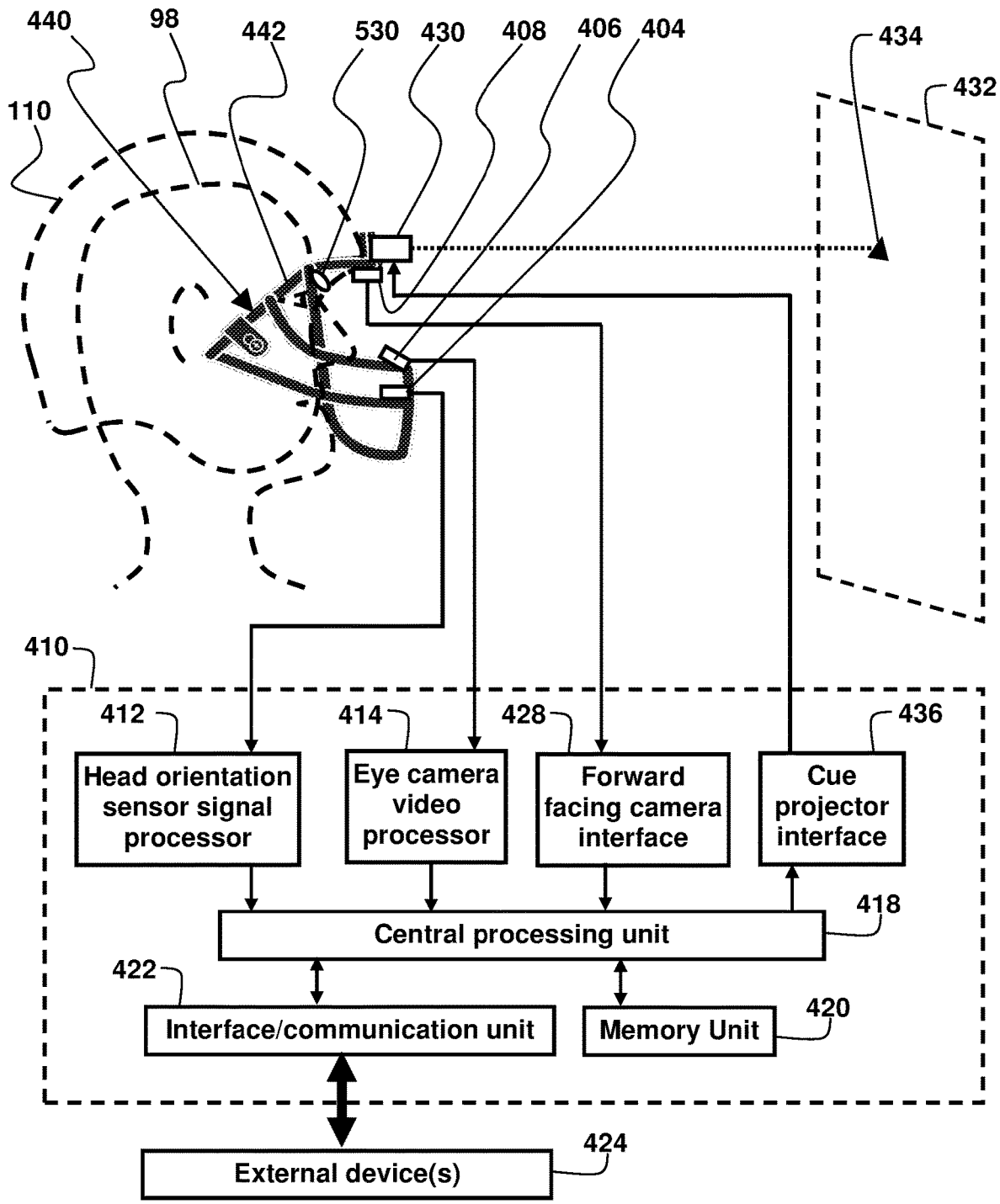
FIG. 1 shows a face guard that comprises an ocular performance measuring system.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

In one embodiment, the present invention comprises head tracking and ocular-based sensors integrated into a face guard. The ocular-based sensors comprise at least one camera that views at least one eye of the faceguard wearer. The camera is configured to measure an eye muscle movement response. The information from this eye camera can be combined with sensors that measure head rotation to determine whether human performance has been degraded by a blow to the head. The vestibular ocular reflex, after an impact, is an example of one eye muscle movement response that could be measured using this embodiment. This vestibular ocular reflex could be used to determine if the wearer has suffered a concussion or mild traumatic brain injury. Other eye muscle movement responses that could be detected can include, but are not limited to pupillometry, ocular saccades, visual pursuit tracking, nystagmus, vergence, convergence, divergence, eye-lid closure, dynamic visual acuity, kinetic visual acuity, retinal image stability, foveal fixation stability, and focused position of the eyes or visual fixation at any given moment.

Eye muscles, also known as extraocular muscles, are located within the orbit but are extrinsic and separate from the eyeball itself. They act to control the movements of the eyeball and the superior eyelid. There are seven extraocular muscles: the levator palpebrae superioris, superior rectus, inferior rectus, medial rectus, lateral rectus, inferior oblique, and superior oblique. Functionally, these seven extraocular muscles can be divided into two groups: (1) the recti and oblique muscles, which are responsible for eye movement; and (2) the levator palpebrae superioris, which is responsible for superior eyelid movement. Three antagonistic pairs of muscles control eye movement: the lateral and medial rectus muscles, the superior and inferior rectus muscles, and the superior and inferior oblique muscles. These muscles are responsible for movement responses of the eye along three different axes: horizontal, either toward the nose (adduction) or away from the nose (abduction); vertical, either elevation or depression; and torsional, movements that bring the top of the eye toward the nose (intorsion) or away from the nose (extorsion). Each extraocular muscle has specific action in order to maintain accurate visual fixation and tracking in response to a stimulus. For example, the lateral rectus, when contracting, responds by abducting the eyeball, the medical rectus muscle contraction response is seen with adduction of the eyeball. Within the eyeball are intra-ocular muscles, the ciliary muscles (which changes the shape and power of the lens) and the (radially oriented) dilator pupillae and (circular) sphincter pupillae muscles, both which regulate the pupillary size.

An eye muscle movement response can be either voluntary or involuntary in response to attempting to acquire accurate visual fixation on a stable or moving visual element (s) of interest or protect the eye. Eye tracking does not directly measure the actual muscle activity, it measures the visible movement response of the eyeball or features of the eye with voluntary or involuntary stimulus. Eye tracking can measure the eye muscle movement responses of the eye and/or eyelid by using visible features or visible reflections of the eye, such as from the pupil, iris, cornea, sclera or from the junctions or boundaries of these regions. The principal types of movement include voluntary motion (both vertical and horizontal), tracking (both voluntary and involuntary) and convergence. Additionally, there are pupillary reactions and movements to control the lens. Although the eyes can be moved voluntarily, most eye movements are through reflexes. Specific extraocular and intraocular muscles of the eye respond to visual, touch, auditory or head positional stimuli in order to maintain fixation on stationary or moving visual element(s) or protect the eye. An example of an eye muscle movement response is the vestibular ocular response. The vestibulo-ocular reflex (VOR) produces eye muscle movement in response to changes in head position, while the eyes remain fixed on a visual target.

Definitions

The definitions that follow apply to the terminology used in describing the content and embodiments in this disclosure and the related claims.

Alert filters are algorithmic computational tools that take in sensor data, compare that data against a set of rules and thresholds, and output a result that is typically in the form of a binary outcome. The rules and thresholds represent the sensitivity and reporting levels desired for the use case. A representative sample of this type of filter is a Random Forest Ensemble. The result can be robust in the data it contains but should lead to a true/false response to each rule or threshold.

An artificial intelligence system is a computer system that attempts to implement aspects of human-level intelligence, in which a machine can learn and form judgements to improve a recognition rate for information as it is used. Artificial intelligence technologies include a machine learning (deep learning) technology that uses an algorithm that classifies/learns the characteristics of input data by itself and an elemental technology that simulates functions such as recognition, judgment, like the human brain by utilizing a machine learning algorithm. The elemental technology may include any one of the following: a linguistic comprehension technique for recognizing human languages/characters, a visual comprehension technique for recognizing objects as in human vision, a reasoning/predicting technique for judging and logically reasoning and predicting information, a knowledge expression technique for processing human experience information as knowledge data, and an operation control technique for controlling autonomous driving of the vehicle or the motion of a robot. A machine learning classifier is a machine learning tool. A machine learning classifier can be an algorithmic computer vision tool that takes an input image data frame (a picture for example), processes the pixel-level information against a target, and outputs a result. Such a classifier can attempt to identify a pattern within the pixels and compare that pattern to a target pattern set. Classifiers can be of a machine learning type (representatives of this group include convolutional neural networks or general adversarial networks) or of a static type (representatives of this group include Haar cascades and Local Binary Patterns), but typically require some form of training for optimization. In another embodiment of this faceguard technology, measurement of eye muscle movement responses, such as with the VOR in a reaction to head movement changes, can be designed with an eye sensor configured for use with a machine learning classifier or computer vision learning classifier, which can identify a pattern in response to an input image frame from the video camera; and compare the pattern to a target pattern set.

Biometrics are defined as physiological measurements and consist of the outputs of sensors that measure the activity of a human body in response to things that are experienced through our senses or imagined. This can be direct measurement of the central nervous system (e.g., the brain) or organs that are connected to the peripheral nervous system (e.g., the pupils of the eyes, sweat glands in our skin). The goal of biometrics generally is to measure bodily responses that are more direct indicators of emotional states. There are many possible biometrics, including DNA, odor, gait, height, handwriting, speech, and vision. Vision-based biometrics can use image sensors and algorithms derived from machine vision. Applications for biometrics include controlling access to a building (physical access), authenticating a user to allow access to some resource (for example, accessing a secured Web site), and identifying a person from among others.

Blinks are the involuntary act of shutting and opening the eyelids, elicited when the cornea is stimulated by touch, impending movement toward the eye, bright light, loud sounds, or other peripheral stimuli. The purpose of these involuntary responses are to protect the eyes from potentially harmful stimuli. They are known to reflect changes in attention and thus they are likely to reflect an individual's cognitive effort. In particular, fewer blinks have been associated with increased attention. For example, a study shows that surgeons had a lower number of blinks when performing surgery as compared to when they were engaged in casual conversations. In addition to the number of blinks, the duration of blinks can also indicate cognitive effort. For example, shorter blink durations were associated with increased visual workload during a traffic simulation task. Similarly, comparing blink data during a hard (math problem solving) and easy task (listening to relaxing music), people exhibited shorter blink durations during the hard task. When the eyes are closed during a blink, there is no incoming visual information to process.

A concussion is defined as an immediate and transient loss of consciousness accompanied by a brief period of amnesia after a blow to the head.

A convolutional neural network (CNN) is defined as an artificial intelligence/machine learning algorithm which can take in an input image, assign importance (learnable weights and biases) to various aspects/objects in the image and be able to differentiate one from the other. The architecture of a CNN is analogous to that of the connectivity pattern of neurons in the human brain and was inspired by the organization of the visual cortex. Individual neurons respond to stimuli only in a restricted region of the visual field known as the receptive field. A collection of such fields overlap to cover the entire visual area.

The corneal reflex is defined as a blinking of both eyes in response to tactile stimulation of the cornea.

An eye correcting algorithm (ECA) is an algorithmic computer vision tool. It builds upon a classifier by attempting to account for movement between the camera itself and the eye being observed. This movement is typically referred to as slippage and the ECA takes the input data frame (the same picture as the classifier), processes the information to determine appropriate offsets, and supplies the offset parameters as its output.

The dynamic visual acuity (DVA) can be used interchangeably with kinetic visual acuity (KVA) as they both have the same meaning. In this document, DVA will be used to assess impairments in a person's ability to perceive objects accurately while actively moving the head, or the ability to track a moving object. It is an eye stabilization measurement while the head is in motion. In normal individuals, losses in visual acuity are minimized during head movements by the vestibulo-ocular system that maintains the direction of gaze on an external target by driving the eyes in the opposite direction of the head movement. When the vestibulo-ocular system is impaired, visual acuity degrades during head movements. The DVA is an impairment test that quantifies the impact of the vestibulo-ocular system pathology on a user's ability to maintain visual acuity while moving. Information provided by the DVA is complementary to and not a substitute for physiological tests of the VOR system. The DVA quantifies the combined influences of the underlying vestibulo-ocular pathology and the person's adaptive response to pathology. DVA testing is sometimes obtained for those persons suspected of having an inner ear abnormality. Abnormalities usually correlate with oscillopsia (a visual disturbance in which objects in the visual field appear to oscillate or jump while walking or moving). Currently with DVA testing, worsening of visual acuity by at least three lines on a visual acuity chart (e.g., Snellen chart or Rosenbaum card) during head turning from side to side at 1 Hz or more is reported as being abnormal. In normal individuals, losses in visual acuity are minimized during head movements by the vestibulo-ocular system that maintains the direction of gaze on an external target by driving the eyes in the opposite direction of the head movement When the vestibular system is impaired, visual acuity degrades during head movements. Individuals with such ocular performance deficits can improve their dynamic acuity by performing rapid "catch-up" saccadic eye movements and/or with predictive saccades.

Dynamic visual stability (DVS) and retinal image stability (RIS) can be used interchangeably. In this document, DVS will be used to describe the ability to visualize objects accurately, with foveal fixation, while actively moving the head. When the eye moves over the visual scene, the image of the world moves about on the retina, yet the world or image observed is perceive as being stable. DVS enables a person to prevent perceptual blurring when the body moves actively. The goal of oculomotor compensation is not retinal image stabilization, but rather controlled retinal image motion adjusted to be optimal for visual processing over the full range of natural motions of the body or with head movement. Although we perceive a stable visual world, the visual input to the retina is never stationary. Eye movements continually displace the retinal projection of the scene, even when we attempt to maintain steady fixation. The human eye has the highest visual acuity in a small circular region of the retina called fovea, having the highest density of cone photoreceptors. For this reason, the eyes are moved to direct the visual targets to the center of the fovea (behavior called scan path of vision). The act of looking can roughly be divided into two main events: fixation and gaze shift. A fixation is the maintenance of the gaze in a spot, while gaze shifts correspond to eye movements. Our visual system actively perceives the world by pointing the fovea, the area of the retina where resolution is best, towards a single part of the scene at a time. Using fixations and saccadic eye movements to sample the environment is an old strategy, in evolutionary terms, but this strategy requires an elaborate system of visual processing to create the rich perceptual experience. One of the most basic feats of the visual system is to correctly discern whether movement on the retina is owing to real motion in the world or rather to self-movement (displacement of our eyes, head or body in space). The retinal image is never particularly stable. This instability is owing to the frequent occurrence of tremors, drifts, microsaccades, blinks and small movements of the head. The perceptual cancellation of ocular drift appears to primarily occur through retinal mechanisms, rather than extra-retinal mechanisms. Attention also plays a role in visual stability, most probably by limiting the number of items that are fully processed and remembered.

Eye tracking means the process of measuring where a subject is looking, also known as our point of gaze. In one embodiment, eye tracking can be performed using a light source, such as near-infrared light, directed towards the center of the eyes (pupil), causing detectable reflections in both the pupil and the cornea (the outer-most optical element of the eye). These resulting reflections, the vector between the cornea and the pupil, can be tracked by an infrared camera. This is the optical tracking of corneal reflections, known as pupil center corneal reflection. These measurements are carried out by an eye tracker, a sensor or sensing unit that records the position of the eyes and the movements they make.

Fixation is defined as a collection of relatively stable gaze points that are near in both spatial and temporal proximity. During fixation, the eyes hold steady on an object, and thus fixation reflects attention to a stimulus. A number of studies have associated fixation-related metrics to cognitive effort and the number of fixations has been shown to strongly correlate with task performance. Because task performance is also correlated with effort expenditure, this result suggests a link between fixation frequency and cognitive effort. In a preferred embodiment, the faceguard technology as described herein can measure fixation metrics, including but not limited to point of fixation or gaze point, duration of fixation, fixation count and intervals between fixations, which can be used to detect and monitor concussions, TBIs, cognition, cognitive deficits, alertness and fatigue.

Focused position of the eyes can be defined as the position or orientation of the eyes to provide a clear image of a visual element or visual object/target of interest on the fovea.

Foveal Fixation Stability (FFS) refers to the ability to maintain an image on the fovea, which is crucial for the visual extraction of spatial detail. If the target image moves 1° from foveal center, or if random movement of the image on the fovea exceeds 2°/sec, visual acuity degrades substantially. Either of these conditions may occur if deficiencies in oculomotor control compromise the ability to maintain target alignment within these limits. Many aspects of oculomotor function do change with age. For example, smooth pursuit movements slow with age, and the range of voluntary eye movements becomes restricted, especially for upward gaze. Dynamic visual acuity (DVA), FFS, and the vestibulo-ocular reflex (VOR) decline with age.

The term gaze is synonymous with fixation. Gaze serves as a reliable indicator of attention and can reflect cognitive effort. Additionally, other major eye movement behaviors such as fixations, saccades, blinks, and pupillary responses can provide distinct information about cognitive effort in response to task demand.

Global shutter is defined as an imaging sensor that is capable of simultaneously scanning the entire area of an image. This is contrasted with a rolling shutter where the image area is scanned sequentially, typically from the top to bottom. Some consumer and industrial machine vision and 3D sensing need a global shutter to avoid motion blur and applications which can be incorporated in this technology include facial authentication and eye tracking.

Kalman filtering (also known as Linear Quadratic Estimation (LQE)) is an algorithm that uses a series of measurements observed over time, containing statistical noise and other inaccuracies, and produces estimates of unknown variables that tend to be more accurate than those based on a single measurement alone, by estimating a joint probability distribution over the variables for each timeframe.

Machine learning is defined as the science of getting computers to learn and act like humans in order to improve their learning over time in an autonomous fashion by feeding them data and information in the form of observations and real-world interactions. Machine Learning fundamentally is the practice of using algorithms to parse data, learn from it, and then make a determination or prediction about something in the world. This entails getting computers to act without being explicitly programmed and is based on algorithms that can learn from data without relying on rules-based programming. Embodiments entail the development of computer models for learning processes that provide solutions to the problem of knowledge acquisition and enhance the performance of developed systems or as described by the adoption of computational methods for improving machine performance by detecting and describing consistencies and patterns in training data. As an example, event detection can be challenging in eye movement data analysis. However, a fully automated classification of raw gaze samples as belonging to fixations, saccades, or other oculomotor events can be achieved using a machine-learning approach. Any already manually or algorithmically detected events can be used to train a classifier to produce similar classification of other data without the need for a user to set parameters. Machine-learning techniques can lead to superior detection compared to current state-of-the-art event detection algorithms and can reach the performance of manual coding. There are numerous algorithms designed to solve a specific problem, such as smooth pursuit detection, noise resilience, separating the slow and fast phase in nystagmus, detecting microsaccades, online event detection, or removing saccades from smooth pursuit data. Most of these algorithms work well within the assumptions they make of the data. Examples of common assumptions are that the input must be high-quality data, or data recorded at high sampling frequencies, and there is no smooth pursuit in it. All algorithms come with overt settings that users must experiment with to achieve satisfactory event detection in their data set, or covert settings that users have no access to. When the sampling frequency is too low, or too high, or the precision of the data is poor, or there is data loss, many of these algorithms fail. Other techniques, such as eye-movement event detectors that uses machine learning are available. Machine learning can choose feature combinations and select appropriate thresholds. In another embodiment of this system using video or image cameras, machine learning can be used in conjunction with computer vision to determine ocular parameters, including but not limited to VOR, pursuit tracking and pupillometry. In another embodiment of the faceguard technology discussed herein, the sensor data acquired can be configured to be fused through a machine learning algorithm (i.e. alternatively known as a filter) to account for dynamic noise inherent in the sensors and fused sensor data from eye and head movement can more accurately measure and predict information transmitted to the interface/communication unit where it can communicate to an external device.

The near accommodative triad or near/accommodative response is a three-component reflex that assists in the redirection of gaze from a distant to a nearby object. It consists of a pupillary accommodation reflex, lens accommodation reflex, and convergence reflex.

Nystagmus is an abnormal involuntary or uncontrollable eye movement characterized by jumping (or back and forth) movement of the eyes, which results in reduced or limited vision. It is often called "dancing eyes". Nystagmus can occur in three directions: (1) side-to-side movements (horizontal nystagmus), (2) up and down movements (vertical nystagmus), or (3) rotation of the eyes as seen when observing the front of the face (rotary or torsional nystagmus).

Ocular parameters are measurable factors that define and determine the components, actions, processes, behavior and functional ability of the eye, eyeball and eyelid. Included in ocular parameters are measurements and/or evaluations regarding the ocular reflexes, ocular saccades, pupillometry, pursuit tracking during visual pursuit, vergence, eye closure, focused position of the eyes, dynamic visual acuity, kinetic visual acuity, retinal image stability, foveal fixation stability, and nystagmus. Reflexes included in the measured ocular parameters include the vestibular ocular reflex, pupillary light reflex, pupillary dark reflex, near accommodative triad, corneal reflex, palpebral oculogyric reflex (Bell's reflex) and the optokinetic reflex. Measuring movements of eye includes the extraocular muscles (which move/rotate the eye), the levator (which raises the eyelid), the ciliary muscles (which helps to focus by changing the lens shape) and the pupillary muscle (which dilates or constricts the pupil). The use of measuring eye muscle movement responses, with eye tracking, has been shown to have significant value in detecting, measuring and monitoring or managing human health conditions, including but not limited to: concussions, traumatic brain injury, vision impairment, neurologic disorders or the neurologic status, cognition, alertness, fatigue and the situational awareness of humans. Additionally, these eye muscle movement responses can provide methods for detecting, measuring, monitoring and managing physiologic impairments due to alcohol and drugs because of their effect on the brain, brainstem, inner ear vestibular system and oculomotor responses. Eye tracking sensors can measure horizontal eye movement, vertical eye movement, or rotation of a human eyeball. All these measurements entail eye muscle movement responses. Commonly, horizontal, vertical, and torsional eye positions are expressed as rotation vectors and eye muscle movements are described as rotations about three principal axes. Horizontal rotation occurs about the vertical Z-axis, vertical rotation about the horizontal X-axis, and torsion about the line of sight or Y-axis. The amount of rotation about each of the three principal axes that is needed to describe a certain direction of gaze and torsional orientation of the eye depends upon the order of sequential rotations (e.g. horizontal, followed by vertical and then torsional). Some oculomotor tasks, such as retinal image stabilization, utilize all three degrees of freedom whereas other tasks, such as voluntary gaze shifts, only require two degrees of freedom, (i.e. gaze direction and eccentricity from primary position). Binocular alignment of retinal images with corresponding retinal points places additional constraints on the oculomotor system. Because the two eyes view the world from slightly different vantage points, the retinal image locations of points subtended by near objects differ slightly in the two eyes. This disparity can be described with three degrees of freedom (horizontal, vertical, and torsional components) that are analogous to the angular rotations of the eye. The eye rotates not only about horizontal and vertical axes but about its line of sight with the top of the eye moving either temporally (extorsion) or nasally (intorsion). Good alignment is a multi-stage process. Neural connectivity between motor and premotor areas serving horizontal, vertical and torsional eye movement serves as a substrate for coordinated movement for the eyeball.

Ocular reflexes are involuntary responses that are usually associated with protective or regulatory functions They require a receptor, afferent neuron, efferent neuron, and effector to achieve the desired protective or functional effect.

Optokinetic nystagmus: The optokinetic reflex, or optokinetic nystagmus, consists of two components that serve to stabilize images on the retina: a slow pursuit phase and a fast "reflex" or "refixation" phase. The reflex is most often tested with an optokinetic drum or projected visual image with alternating stripes of varying spatial frequencies.

Palpebral oculogyric reflex (or Bell's reflex) is an upward and lateral deviation of the eyes during eyelid closure against resistance, and it is particularly prominent in patients with lower motor neuron facial paralysis and lagophthalmos (i.e. incomplete eyelid closure).

The pupillary light reflex is an autonomic reflex that constricts the pupil in response to light, thereby adjusting the amount of light that reaches the retina. Pupillary constriction occurs via innervation of the iris sphincter muscle, which is controlled by the parasympathetic system.

The pupillary dark reflex is an autonomic reflex that dilates the pupil in response to dark. It can also occur due to a generalized sympathetic response to physical stimuli and can be enhanced by psychosensory stimuli, such as by a sudden noise or by pinching the back of the neck, or a passive return of the pupil to its relaxed state.

Pupillometry refers to an objective way of measuring pupil size, and more specifically, the diameter of the pupil. Often pupil parameters are measured including: maximum, minimum and final pupil diameter, latency, amplitude and peak and average constriction and dilation velocities under numerous stimulus conditions including: dim pulse, dim step, bright pulse, bright step, bright red step and bright blue step. It has been observed that concussions and mild traumatic brain injury adversely affects the pupillary light reflex suggesting an impairment of the autonomic nervous system. Quantitative pupillary dynamics can also serve as an objective mild traumatic brain injury biomarker and these pupillary measurements can be reliably replicated. Quantitative pupillometry can be a measure of concussion analysis and associated with intracranial pressure. Changes in pupil size, which are controlled by the involuntary nervous system, can serve as a reliable proxy of mental effort. For example, when people are asked to memorize numbers, retain them in memory, or perform multiplication, the size of their pupil seems to correlate with the difficulty of the task. Similarly, variation in pupil size can also carry information about cognitive effort. For example, the level of difficulty measured as the number of steps required to complete a task has been shown to impact pupil dilation variation. Increased cognitive load measured as implicit and explicit time limit also has a significant impact on pupil dilation variation. Eye tracking studies provide ample evidence that certain eye movement behaviors (i.e., fixations, saccades, blinks, and pupillary responses) have the potential to reveal information about cognitive effort. There are a number of machine learning studies that have successfully used eye movement data to predict a variety of different behaviors. Saccades and blinks are associated with cognitive effort, but also show that the metrics related to saccades and blinks were among most effective variables for detecting task demand. While fixation serves as a reliable and direct indicator of attention and thus information processing, more effective in classifying task demand appears to be the saccade and blink eye movement behaviors, which take place between, and not during, fixations. Eye movement data carries distinct information about task demand. In some studies, pupillary responses were more effective than other eye moment behaviors in detecting task demand. In particular, saccade-to-fixation pupil dilation and pupil variation ratios proved to be most valuable in detecting task demand. In another embodiment, the faceguard technology discussed herein can measure eye movement behaviors, including but not limited to fixations with and without head movement, saccades, eyeblinks and pupillary responses to detect and monitor the neurologic status, concussion, cognition, alertness and fatigue.

A saccade is a rapid movement of an eye between visual fixation points. Saccades are quick, simultaneous movements of both eyes in the same direction. They range in amplitude from the small movements made while reading, for example, to the much larger movements made while gazing around a room. We cannot consciously control the speed of movement during each saccade; the eyes move as fast as they can. One reason for the saccadic movement of the human eye is that the central part of the retina (known as the fovea) plays a critical role in resolving objects. By moving the eye so that small parts of a scene can be sensed with greater resolution, body resources can be used more efficiently. Saccadic eye movements are said to be ballistic because the saccade generating system cannot respond to subsequent changes in the position of the target during the course of the eye movement. If the target moves again during this time, the saccade will miss the target, and a second saccade must be made to correct the error. While visual information is not processed during saccadic eye movements, they still can provide information about viewing behavior. According to the theory of visual hierarchy a stimulus is inspected by scanning it through a sequence of visual entry points. Each entry point acts like an anchor, which allows the user to scan for information around it. According to this perspective, longer duration of saccadic eye movements could indicate increased cognitive effort in finding a suitable entry point into a visual display. The saccade that occurs at the end of a head turn with someone who has an abnormal VOR is usually a very clear saccade, and it is referred to as an overt saccade. An overt saccade is indicative of abnormal semicircular canal function on the side to which the head was rotated. For example, an overt saccade after a leftwards head rotation means the left semicircular canal has a deficit. Covert saccades are small corrective saccades that occur during the head movement of a person with abnormal inner ear function. Covert saccades reduce the need for overt saccades that occur at the end of the head movement and are more difficult to identify than overt saccades. Covert saccades are very fast. This makes them almost impossible to detect by the naked eye, and therefore sensitive eye tracking measurements are required to detect covert saccades. There is a rapid deceleration phase as the direction of sight lands on the new target location. Following a very short delay, large saccades are frequently accompanied by at least one smaller corrective saccade to further approach a target location. Corrective saccades can occur even if the target has been made to disappear, further supporting the projected, ballistic nature of saccadic movements. However, corrective saccades are more frequent if the target remains visible.

Saccade accuracy, amplitude, latency and velocity can be measured with oculomotor eye movements, most commonly with saccades, vergence, smooth pursuit, and vestibulo-ocular movements. Saccades can be elicited voluntarily, but occur reflexively whenever the eyes are open, even when fixated on a target. They serve as a mechanism for fixation, rapid eye movement, and the fast phase of optokinetic nystagmus. The rapid eye movements that occur during an important phase of sleep are also saccades. After the onset of a target appearance for a saccade, it takes about 200 milliseconds for eye movement to begin. During this delay, the position of the target with respect to the fovea is computed (that is, how far the eye has to move), and the difference between the initial and intended position is converted into a motor command that activates the extraocular muscles to move the eyes the correct distance in the appropriate direction. The latency, amplitude, accuracy and velocity of each respective corrective saccade and latency totals and accuracy can be calculated.

Saccade accuracy refers to the eye's ability to quickly move and accurately shift from one target fixation to another. Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude refers to the size of the eye movement response, usually measured in degrees or minutes of arc. The amplitude determines the saccade accuracy. This is sometimes denoted using "gain". It is also described as the angular distance the eye travels during the movement. For amplitudes up to 15 degrees or 20 degrees, the velocity of a saccade linearly depends on the amplitude (the so-called saccadic main sequence). Saccade duration depends on saccade amplitude. In saccades larger than 60 degrees, the peak velocity remains constant at the maximum velocity attainable by the eye. In addition to the kind of saccades described above, the human eye is in a constant state of vibration, oscillating back and forth at a rate of about 60 Hz.

Saccade velocity is the speed measurement during the eye movement. High peak velocities and the main sequence relationship can also be used to distinguish micro-saccades from other eye movements, such as ocular tremor, ocular drift and smooth pursuit.

Saccade latency is the time taken from the appearance of a target to the beginning of an eye movement in response to that target. Disorders of latency (timing) can be seen with saccades, VOR and visual pursuit.

Saccadic Inhibition. Studies of eye movements in continuous tasks, such as reading, have shown that a task-irrelevant visual transient (for example a flash of a portion of the computer display) can interfere with the production of scanning saccades. There is an absence or near-absence of saccades initiated around 80-120 ms following the transient. This inhibitory effect (termed saccadic inhibition (SI)) is also observed in simple saccade experiments using small visual targets and it has been suggested that SI may be like or underlie a remote distractor effect.

Sensor Fusion is an algorithm that combines sensory data or data derived from disparate sources such that the resulting information has less uncertainty than would be possible when these sources were used individually. The term 'uncertainty reduction' in this case can mean more accurate, more complete, or more dependable, or refers to the result of an emerging view, such as stereoscopic vision (calculation of depth information by combining two-dimensional images from two cameras at slightly different viewpoints). The sensors can be of the same type (such as cameras for a stereoscopic image) or of differing types (such as combining accelerometer and gyroscopic data in a Kalman Filter). They can also be complementary (independent sensors measuring different properties combined to give a more complete view), competitive (independent sensors measuring the same property for fault tolerance or redundancy), or cooperative (using multiple sensor measures to derive information not available to any single sensor). In an embodiment of the faceguard described herein, the head tracking sensor and eye sensor can be configured to use such a sensor fusion algorithm to provide more accurate information regarding measurement of eye fixation with head movement. Alternatively, different eye sensors measuring eye features at different points can be configured for sensor fusion to obtain more accurate data regarding the eye muscle movement responses.

Situational awareness (SA) is defined as being aware of one's surroundings, comprehending the present situation, the context, meaning, the possible progression of events and being able to predict outcomes. It is a cognitive process that involves perceiving and comprehending critical elements of information during a certain task. It is simply 'having an idea of what's going on around you. It is a key human skill that, when properly applied, is associated with reducing errors of human performance activities. Eye-tracking sensors, which measure ocular movements (e.g. eye and eyelid) can be used to provide an objective and qualitative measure of the initial perception component of SA. There is evidence that eye tracking can improve learning and aid feedback of user activity.

Slippage is defined as movement of the faceguard relative to the wearer's head. Slippage typically causes faceguard movement that is out of phase with the wearer's head. The slippage offset is an algorithm that accounts for slippage and computes an appropriate value that can be used to synchronize sensor data. In another embodiment, the faceguard is configured for measuring and correcting slippage offsets. The measurement and correction of slippage offsets is carried out by one or more sensors selected from the group of: the existing multi-axis inertial measurement unit (IMU), the existing imaging sensor, an additional IMU, and a wider field of view image sensor.

Smooth pursuit movements are slow tracking movements of the eyes designed to keep a moving stimulus on the fovea. Such movements are under voluntary control in the sense that the observer can choose whether or not to track a moving stimulus.

Vergence is the simultaneous movement of both eyes in opposite directions to rapidly obtain or maintain single binocular vision or ocular fusion, or singleness, of the object of interest. It is often referred to as convergence or divergence of the eyes, to focus on objects that are closer or further away from the individual. In order to maintain binocular vision, the eyes must rotate around a vertical axis so that the projection of the image is in the center of the retina in both eyes. Vergence measurements can easily be performed. Normally, changing the focus of the eyes to look at an object at a different distance will automatically cause vergence and accommodation, known as the accommodation-convergence reflex. Convergence is the simultaneous inward movement of both eyes toward each other, usually to maintain single binocular vision when viewing an object. Vergence tracking occurs in the horizontal, vertical, and/or cyclorotary dimensions. Vergence requires that the occipital lobes be intact, and the pathway involves the rostral midbrain reticular formation (adjacent to the oculomotor nuclei) where there are neurons that are active during vergence activities. It comprises a complex and finely tuned interactive oculomotor response to a range of sensory and perceptual stimuli. There is an important interaction between the vergence system and vestibular (inner ear balance) system. To keep the eyes focused on a visual element or object of interest, while the head is moving, the vestibular system senses head rotation and linear acceleration, and activates the eyes to counterrotate to keep gaze constant even though the head is moving. As an example, this is what enables us to see a tennis ball while moving our head. The problem becomes more difficult at near vision, because the eyes are not located at the center of rotation of the head, but rather are about 10 cm anterior to the axis of rotation. Therefore, when a person is focused on a near target (such as 10 cm away), the amount of eye movement needed to keep the target fixated is much greater than the amount needed to view a similar object 100 cm away. This additional eye movement is supplied by the otoliths (linear acceleration sensing element) that produce eye movement that are roughly inversely proportional to the distance of the target from the center of the eye. Persons with disorders of their otoliths, might reasonably have a selective problem with stabilizing their vision while the head is moving, at near vision. Vergence can be also be adversely affected by other factors including aging, visual abnormalities, concussion and traumatic brain injury (TBI).

Vergence eye movements are used to track objects that move in depth in one's binocular visual field to attain and maintain a fused and single percept. When we shift our gaze from a far object to a near object, our eyes converge, the lenses of our eyes modify their focus (accommodate), and our pupils often constrict. These three combined responses are termed the near triad. Convergence is the simultaneous inward movement of both eyes toward each other, usually in an effort to maintain single binocular vision when viewing an object. This is the only eye movement that is not conjugate, but instead adducts the eye. Divergence is the simultaneous outward movement of both eyes away from each other, usually in an effort to maintain single binocular vision when viewing an object. It is also a type of vergence eye movement. The mechanism and control of vergence eye movements involves complex neurological processes that may be compromised in individuals with traumatic brain injury, thus frequently resulting in a wide range of vergence dysfunctions and related near-work symptoms, such as oculomotor-based reading problems. It has been determined that 90 percent of individuals having mTBI have oculomotor dysfunction encompassing vergence, accommodation, version, strabismus, and cranial nerve palsy and report vision-based symptoms. Following mTBI, a vergence system abnormality is often the most common dysfunction. Vergence movements align the fovea of each eye with targets located at different distances from the observer. Unlike other types of eye movements in which the two eyes move in the same direction (conjugate eye movements), vergence movements are disconjugate (or disjunctive). They involve either a convergence or a divergence of the lines of sight of each eye to see an object that is nearer or farther away. Convergence is one of the three reflexive visual responses elicited by interest in a near object. Other components of the so-called near reflex triad are accommodation of the lens, which brings an object into focus, and pupillary constriction, which increases the depth of field and sharpens the image on the retina.

Visual pursuit means the movement of the eyes in response to visual signals. Smooth pursuit eye movements allow the eyes to closely follow a moving object. It is one of two ways that humans and other visual animals can voluntarily shift gaze, the other being saccadic eye movements. Pursuit differs from the VOR, which only occurs during movements of the head and serves to stabilize gaze on a stationary object. Most people are unable to initiate pursuit without a moving visual signal. The pursuit of targets moving with velocities of greater than 30°/s tend to require catch-up saccades. Most humans and primates tend to be better at horizontal than vertical smooth pursuit, as defined by their ability to pursue smoothly without making catch-up saccades. Most humans are also better at downward than upward pursuit. Pursuit is modified by ongoing visual feedback. Smooth pursuit is traditionally tested by having the person follow an object moved across their full range of horizontal and vertical eye movements.

Visual pursuit tracking can be defined as measuring a person's eye movement ability to match a visual element or visual target of interest movement. Visual pursuit eye movements utilize some of the vestibulo-ocular reflex pathways and require a visual input to the occipital cortex to permit locking of the eyes onto a visual element, visual object or target of interest. Pursuit movements are described to be voluntary, smooth, continuous, conjugate eye movements with velocity and trajectory determined by the moving visual target. By tracking the movement of the visual target, the eyes maintain a focused image of the target on the fovea. A visual stimulus (the moving visual target) is required to initiate this eye movement. Pursuit gain, which is the ratio of eye velocity to target velocity, is affected by target velocity, acceleration and frequency. Visual pursuit tracking may be related to factors that are difficult to quantify, such as the degree of alertness present in persons, visual acuity or the visibility of the pursuit target. Visual pursuit tracking can be decayed with alcohol, centrally acting medications such as anticonvulsants, minor tranquilizers, preparations used for sleep. It is also clear that visual pursuit performance declines with age and can be adversely affected by vestibular dysfunction, central nervous system disorders and trauma, such as concussions and traumatic brain injury (TBI).

Visual pursuit accuracy is defined by the ability of the eyes to closely follow a moving object. The pursuit of targets moving with velocities of greater than 30°/s tends to require catch-up saccades. Smooth pursuit accuracy represents how closely the percentage of time the smooth pursuit velocity value remains within the target velocity value.

Visual pursuit movements are much slower tracking movements of the eyes designed to keep the moving stimulus on the fovea. Such movements are under voluntary control in the sense that the observer can choose whether to track a moving stimulus. Although it may appear that our eyes are not moving when we fixate an object, in fact they are in continual small-scale motion, showing irregular drift and tremor, interspersed by miniature saccadic movements (less than 0.5 degrees). These fixational eye movements are essential to prevent our visual percept from fading. Pursuit consists of two phases—initiation and maintenance. Measures of initiation parameters can reveal information about the visual motion processing that is necessary for pursuit.

Visual pursuit acceleration—this is the rate of change of the eye velocity. The first approximately 20 milliseconds of pursuit tends to be the same regardless of target parameters. However, for the next 80 milliseconds or so, target speed and position have a large effect on acceleration.

Visual pursuit velocity—After pursuit initiation, speed of the eye movement (velocity) usually rises to a peak and then either declines slightly or oscillates around the target velocity. This peak velocity can be used to derive a value for gain (peak velocity/target velocity). It is usually near the velocity of the target. Instead of using peak velocity, it is also sometimes of interest to use measures of velocity at times relative to either target appearance or pursuit initiation. Eye velocity up to 100 milliseconds after target appearance can be used as a measure of prediction or anticipation. Velocity measured 100 milliseconds after pursuit begins reveals something about the ability of pursuit system in the absence of visual feedback.

Visual pursuit latency is defined by the time from target appearance to the beginning of pursuit. The difficulty is defining when pursuit begins. Usually it is measured from traces of eye velocity. It is often calculated by finding the intersection between two regression functions one fitted to velocity about the time of target appearance, and the second fitted over the initial part of the pursuit response.

Vestibulo-ocular movements are defined as movements that stabilize the eyes relative to the external world, thus compensating for head movements. These reflex responses prevent visual images from "slipping" on the surface of the retina as head position varies. The action of vestibulo-ocular movements can be appreciated by fixating an object and moving the head from side to side; the eyes automatically compensate for the head movement by moving the same distance but in the opposite direction, thus keeping the image of the object at more or less the same place on the retina. The vestibular system detects brief, transient changes in head position and produces rapid corrective eye movements. Sensory information from the semicircular canals directs the eyes to move in a direction opposite to the head movement. While the vestibular system operates effectively to counteract rapid movements of the head, it is relatively insensitive to slow movements or to persistent rotation of the head. For example, if the vestibulo-ocular reflex is tested with continuous rotation and without visual cues about the movement of the image (i.e., with eyes closed or in the dark), the compensatory eye movements cease after only about 30 seconds of rotation. However, if the same test is performed with visual cues, eye movements persist. The compensatory eye movements in this case are due to the activation of the smooth pursuit system, which relies not on vestibular information but on visual cues indicating motion of the visual field.

The vestibulo-ocular reflex is defined as a reflex, initiated by head movement which activates the vestibular system of the inner ear and results in eye movement. This reflex functions to stabilize images on the retinas (when gaze is held steady on a visual target) during head movement by producing eye movements in the direction opposite to head movement, thus preserving the image on the center of the visual field. The vestibulo-ocular reflex (VOR) entails eye movements in the opposite direction of head movement, in order to maintain steady gaze and prevent retinal image slip. Motion signals from the utricle, saccule, and/or semicircular canals in the inner ear travel through the utricular, saccular, and/or ampullary nerves to areas in the vestibular nucleus, which sends output to cranial nerve III, IV, and VI nuclei to innervate the corresponding extraocular muscles. Horizontal VOR involves coordination of the abducens and oculomotor nuclei via the medial longitudinal fasciculus. An abnormal VOR will involve catch-up saccades while the patient rotates his or her head, and it can indicate bilateral, complete, or severe (>90%) loss of vestibular function. VOR can be assessed in several ways. During the Doll's eye maneuver, the individual continuously fixates on an object while the examiner moves his or her head from side to side, and the examiner watches the individual's eyes for catch-up saccades. VOR can also be assessed by providing a visually displayed target upon which an individual is focused up and multiple eye and head movement measurements are taken as the individual's head is rotated. Comparisons are made between the head and eye measurements. In normal circumstances, as the head rotates to the right 30 degrees corresponding eye movements occur in the opposite direction 30 degrees to maintain eye fixation on the target. One can expect approximately a 10 msec difference between head movement and eye movement. A delay of eye movement response greater than 20-30 msec would indicate a VOR abnormality. Caloric stimulation can also be used to examine the VOR. Irrigation of the external auditory meatus with ice water causes convection currents of the vestibular endolymph that displace the cupula in the semicircular canal, resulting in a fast component of eye movement toward the opposite ear.

Basic Science: Concussion and Traumatic Brain Injury (TBI)

Broadly speaking, a concussion, the most common type of traumatic brain injury, results from impact or impulsive forces to the head, neck or face and typically affects the central nervous system and the peripheral vestibular system. Most concussions meet criteria for mild traumatic brain injury. Mild traumatic brain injury (mTBI) has been defined as loss of consciousness less than 30 minutes and less than 24 hours and no skull fracture. A moderate TBI has a loss of consciousness greater than 30 minutes and less than 24 hours, with or without skull fracture. Severe TBI is characterized by loss of consciousness greater than 24 hours, with contusion, hematoma or skull fracture.

Due to the variability and subtlety of symptoms, concussions may go unrecognized or be ignored, especially with the pressure placed on athletes to return to competition. There is public consensus that undiagnosed, and therefore untreated, concussions represent a significant long-term health risk to players.

Closed head injury can cause several different types of brain injury including coup, contre-coup, acceleration-deceleration trauma, rotational trauma and molecular commotion. Acceleration-deceleration trauma causes discrete lesions which affect only certain areas of the brain. Both rotational trauma and molecular commotion cause diffuse damage that impairs many aspects of brain function. Acceleration-deceleration trauma occurs when the head is accelerated and then stopped suddenly, as with players colliding, which can cause discrete, focal lesions to two areas of the brain. The brain will suffer contusions at the point of direct impact and at the site directly opposite the point of impact, due to the oscillation movement of the brain within the skull (e.g. coup or site of contact and contrecoup or opposite site of contact respectively). Trauma results from the oscillation (movement) of the brain against bony projections on the inside of the skull. Brain injuries may also occur as a result of acceleration-deceleration trauma unaccompanied by impact. The prefrontal areas and the anterior portion of the temporal lobes are the parts of the brain most often affected by acceleration-deceleration trauma. Thus, if the brain is repeatedly propelled against the front part of the skull, there is likely to be major injuries. Rotational trauma occurs when impact causes the brain to move within the cranium at a different velocity than the skull. This results in a shearing of axons within the upper spinal cord, brainstem and midbrain. Because this type of injury damages neural connections rather than gray matter, it can affect a wide array of cerebral functions and should therefore be considered a type of diffuse injury. Molecular commotion is a disruption in the molecular structure of the brain which may cause permanent changes in both white and gray matter. This type of diffuse brain injury may occur in the absence of discrete lesions.

The major effects of trauma on the brain can be divided into two categories: primary and secondary (or late) effects. The primary effects are those that are caused directly by the head trauma and include concussion, contusion, and laceration of the central nervous system.

Concussion is a reversible state of diffuse cerebral dysfunction associated with a transient alteration in consciousness. Most often there is a brief period of loss of consciousness. However, athletes may be only severely stunned or dazed. Typically, there is loss of memory for recent events (retrograde amnesia), and this may extend for some seconds or minutes following the injury and, rarely, with more severe impact, for days or more. A variable period of inability to learn new material (anterograde amnesia) typically follows recovery of consciousness and may be dense enough to leave the individual with no memory of early post injury occurrences. Rarely, some players are unable to remember ongoing occurrences. The retrograde amnesia is presumed to be caused by a mechanical distortion of neurons, probably in the temporal lobes, which consolidate the memory trace. The anterograde amnesia is presumed to be the result of distortion of the mesial temporal-limbic circuits known to be necessary for learning.

The underlying pathophysiology of concussion appears to be a shearing effect. Rapid displacement of the head, in either acceleration or deceleration injury, causes a swirling of the cerebrum within the cranium, and shearing forces play most markedly at the junctions between brain tissues of different density and location. Rotational injuries may be particularly damaging, since the brainstem torques while there is a lot of inertia against the rotation of the cerebral cortex. This results in torsion of the nerve fibers in the core of the brain (i.e., the reticular activating system). Another major zone of diffuse axonal injury is the interface between gray and white matter. It is here and in the core of the rostral brainstem that microscopic evidence of ruptured axons can be found pathologically. It is not surprising that the athlete's resistance to future concussion tends to decline with repeated concussions or that repeated concussion may lead to dementia.

Contusions of the brain are bruises usually associated with more severe trauma than necessary for concussion. They are most prominent at the summits of gyri, the cerebral poles (particularly the frontal poles and the anterior temporal lobe), and portions of the brainstem. All these regions lie close to the bony and dural surfaces of the cranial cavity. They may directly underlie the site of the violent blow to the cranium or may be opposite the site of impact (contrecoup). The contusions can usually be seen acutely on CT or MRI scans.

Laceration of the brain usually follows cranial trauma severe enough to cause fracture of the skull and penetrating injury to the brain by skull fragments or foreign objects. However, fracture of the skull need not be associated with laceration or contusion or major concussion. On the other hand, laceration may on occasion occur with severe shearing forces unassociated with fracture. Usually some form of hemorrhage (intracerebral, subdural, epidural) is associated with laceration.

The secondary effects of cranial trauma that may further compromise brain function are edema, hypoxia, hemorrhage, infection and epilepsy. Edema may be the result of diffuse shearing of capillary, glial, and neuronal membranes or may be secondary to local contusion or laceration. Edema can generate local pressure that can compromise both arterial and venous cerebral blood flow, causing ischemia and more edema. This may precipitate a vicious cycle sometimes impossible to reverse. The mass effect of edema, focal or diffuse, can cause rostrocaudal brainstem deterioration (possibly with herniation), a major cause of delayed death from head trauma. Increased intracranial pressure (ICP), mostly due to edema but added to by any intracranial bleeding, is a major cause of secondary injury. High pressure decreases the perfusion pressure in brain blood vessels (since the perfusion pressure is the mean arterial pressure minus the intracranial pressure). If this is too low, there will be further damage to neural tissue due to ischemia, which will result in further edema and an even greater increase in pressure.

Intracranial hemorrhage, arterial or venous, intra- or extracerebral, is a frequent sequela of cranial trauma and may be great enough to cause rostrocaudal deterioration of neural function and death if not recognized and attended to immediately. Rostrocaudal deterioration, if rapid, may itself cause hemorrhage by downward stretching and tearing of the paramedian penetrating arteries of the midbrain and pons. Subdural and epidural hematomas both can be treated via surgical intervention, which can be curative if undertaken prior to irreversible brain damage. Both epidural and subdural hematoma are extracerebral. For this reason, and because they are soft masses, there tends to be relatively little effect on the underlying and compressed cerebral hemispheres. However, due to distortion of the brain itself, secondary rostrocaudal distortion of the brainstem is the process that usually gives rise to the major clinical signs: depression of consciousness (reticular formation), hemiparesis (cerebral peduncles), eye signs (third and sixth nerves), and respiratory pattern abnormalities.

Herniation, the process of squeezing brain tissue from one intracranial compartment into another, is often the terminal occurrence since this produces permanent damage in the region of herniation.

Epidural hematomas are most often arterial. They are usually the result of transection of the middle meningeal artery by a skull fracture that passes through the middle meningeal groove. It must be emphasized, however, that fracture is not necessary since the skull has elasticity that may permit the violent blow to rupture the artery which is pinned between the dura matter and the skull. Because of the location of the middle meningeal artery, the clots typically lie over the lateral hemisphere (temporal and/or parietal lobes). Since the epidural hematoma is under arterial pressure, it typically continues to grow unless evacuated. However, because the dura is adhered to the inside of the skull, and since the clot is between these layers, the growth of the clot is over hours. The typical middle meningeal artery epidural hematoma is associated with a syndrome that appears within hours of the injury.

Classically, trauma is associated with a concussive loss of consciousness. The athlete may awaken from this to achieve a good level of consciousness (lucid interval) only to lose consciousness again from brainstem distortion caused by the clot growth. If the bleeding is very severe there is no lucid interval. The individual does not have time to awaken from the concussion before compressive brainstem deterioration begins. Surgical evacuation is critical. Less often, epidural collections may be the results of tears in the venous sinuses or leakage from the diploic veins. These hemorrhages may occur over any portion of the hemispheres or in the posterior fossa and are much slower.

A subarachnoid hemorrhage (SAH) involves bleeding into the space between the surface of the brain (the pia mater) and the arachnoid, (e.g. between two of three coverings of the brain). Strengthening rod-like fibers known as fibrous trabeculae cross through the subarachnoid space to connect the arachnoid membrane to the pia mater, and cerebrospinal fluid fills the cavity to flow around the brain. The subarachnoid space also contains the blood vessels which supply the brain and spinal cord with blood and oxygen. This cavity helps to cushion the brain to protect it from injury and continues down the spinal column along with the arachnoid membrane. The hemorrhage is presumed to arise from angular forces that cause shearing of vessels as acceleration/deceleration movement of the brain occurs with linear/tangential/rotational injuries. The bridging veins tend to shear where they enter the dura after passing through the thin subdural space between the dura and arachnoid. Symptoms associated with traumatic subarachnoid hemorrhage may or may not resemble those associated with spontaneous hemorrhage, as trauma can involve multiple injuries with overlapping symptoms. Because the blood is under very low pressure (being from veins) the hematoma tends to collect slowly, causing signs and symptoms that develop over days to months. Head trauma that can be so minor that it is not remembered may result in a subdural hematoma under these circumstances. Acute subdural hematomas are seen less frequently. They are usually associated with head trauma severe enough to cause skull fracture and cerebral contusion or laceration. Epidural hematoma and intracerebral hematoma are frequently associated. The mortality is extremely high, and the residual dysfunction of survivors is severe.

Arterial dissection may affect the carotid or vertebral arteries. This is usually associated with a tear in the intimal lining of the artery and an accumulation of blood in the media. Stroke may result from blockage of the artery or its branches or from artery-to-artery emboli arising from the site of vessel damage. The weakened artery may also rupture (often into the subarachnoid space) with potentially catastrophic results.

Pathologic Findings in the Brain with Trauma

Impact forces may cause linear, rotational, or angular movements of the brain, and more commonly a combination of these movements. In rotational movement, the head turns around its center of gravity, and in angular movement it turns on an axis not through its center of gravity. The amount of rotational force is thought to be the major component in concussion and its severity. As the angular acceleration increases, the risk of mild traumatic brain injury increases respectively.

The parts of the brain most affected by rotational forces are the midbrain and diencephalon. It is thought that the forces from the injury disrupt the normal cellular activities in the reticular activating system located in these areas, and that this disruption produces the loss of consciousness often seen in concussion. Other areas of the brain that may be affected include the upper part of the brainstem, the fornix, the corpus callosum, the temporal lobe, and the frontal lobe. Severe centrifugal forces exert tremendous shearing pressures on the brainstem and upper spinal cord. A form of neurodegeneration reported in professional football players is "Chronic Traumatic Encephalopathy" (CTE). In addition to football players, CTE has been reported in other athletes involved in violent blows to the head, in traumatic military activities and in a few non-athletes with a history of TBI.

The syndrome of CTE begins insidiously, usually many years after the individuals have stopped playing sports or their other activities, with inattention, mood and behavior disturbances, confusion, and memory loss, and progresses inexorably over many years to a stage of full-blown dementia and parkinsonism. The brain, in CTE, shows atrophy, dilatation of the lateral and third ventricles, and thinning of the corpus callosum. Microscopic examination reveals hyperphosphorylated tau (p-tau) deposition in neurons, astrocytes, and cell processes around small vessels. These changes are patchy and affect the deeper parts of cerebral sulci. Other neurodegenerative pathologies, including beta amyloid deposition in the form of diffuse or neuritic plaques, amyloid angiopathy, TDP-43-inclusions may co-exist with p-tau deposition. Tau deposition is the key cellular change in CTE. The cause of CTE is thought to be TBI, especially repeated cerebral concussions and sub-concussive trauma. In the acute phase, concussion, especially following side-to-side hits to the head, causes diffuse axonal injury (DAI) and triggers the release of tau and beta amyloid in the brain. This, along with cerebral hypoxia, excitotoxicity and inflammatory mediators, set in motion a progressive destructive cascade that causes neurodegeneration many years later.

Diffuse axonal injury (DAI) is a special traumatic lesion, which occurs following blows to the unsupported head. During such injuries, the cerebrum goes into a back and forth gliding motion, pivoting around the brainstem. The brainstem, together with the cerebellum, is held firmly fixed by the tentorium, and the falx prevents side-to-side motion. Axons are stretched but do not snap from this injury. Their sudden deformation causes changes in the axonal cytoskeleton (compaction of neurofilaments, fracture of microtubules) that lead to an arrest of the fast axoplasmic flow. Components of this flow, including mitochondria and other organelles, accumulate proximal to the lesion and cause axonal swellings (spheroids). Some axons with mild lesions probably recover but many eventually rupture. It takes several hours from trauma to axonal rupture. Influx of calcium through the stretched axolemma probably initiates the process that leads to the formation of spheroids. Mitochondrial dysfunction and neuroinflammation contribute to the local tissue injury. Ruptured axons undergo Wallerian degeneration leading to loss of neurological function. Loss of axons may lead to dying back of neurons. Thus, DAI is a multifaceted process that evolves over time. The swellings are located at nodes of Ranvier where the axolemma is more liable to deform because there is no myelin. Brain damage is most severe along midline structures (corpus callosum, brainstem) where the shear forces are greatest, and at the cortex-white matter junction because of the change in the consistency of brain tissue. Cerebral concussion is thought to be a mild form of DAI without permanent pathology. The loss of consciousness in concussion is probably due to a functional disturbance of the reticular activating substance of the brainstem. This is part of the central nervous system that is subjected to the highest twisting force during sagittal rotation of the hemispheres.

In one embodiment, the faceguard is configured to protect the face and cranial structures from the sequalae mentioned above and the system is configured to be a portable system for measuring, monitoring and managing the human health conditions resulting from concussions/traumatic brain injuries, including but not limited to such as changes in the neurologic status, behavior and deficits in cognition, alertness, fatigue, and vision.

Faceguard as an Ocular Performance-Based Measurement Device

Referring now to the figures that describe the faceguard as a device which can be used for ocular performance measurements, FIG. 1 shows the head orientation sensor 404, is, FIG. 1 shows the head orientation sensor 404, is rigidly attached to the centered ocular performance measuring faceguard 440. In at least one embodiment, the head orientation sensor 404, senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The head orientation sensor 404, can be constructed from one or more elements or it can be monolithic. The head orientation sensor 404, can use one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system (MEMS) integrated circuit.

Placement of the user facing eye sensor on the faceguard elements is critical, depending on the ocular parameter being measured. In one embodiment, the eye sensor or imaging sensor can be attached to the faceguard, vertically in line with the pupil and horizontally below the level of the infraorbital rim, to provide an unobstructed view when the user is looking straight ahead. In this instance, accurate measurement requires the sensor(s) to be located at an angle below the inferior margin of the upper eyelid, where there is an unencumbered view of the eyeball characteristics. Measurements above the inferior margin of the upper eyelid would be adversely affected by the upper eyelid and eyelashes. The sensor can also be in another location which allows for valid measurement of rotation of the human eyeball movement and vision or eyelid muscle movement and the test selected for measurement. As another example, eyelid muscle movement responses, can be measured by sensors located above the inferior margin of the upper eyelid. A combination of eye sensors, attached to the faceguard, can be configured to measure the movement characteristics of the extraocular eye muscle movement responses as well as intraocular eye muscle movement responses. The responses measured can detect not only evidence of a concussion and traumatic brain injury, but also characteristics of alertness, fatigue, cognition and attention.

Eye sensors can also obtain biometric information.

Further referring to FIG. 1, the user facing eye sensor 406, is more specifically an eye tracking digital video camera that is pointed at the eyes of the person. The eye sensor 406, can be responsive to any eye position, including vertical movement of the eyes (which represents pitch), rotation of the eyes (which represents roll), and horizontal movement of eyes (which represents yaw). It can also be responsive to eyelid position and eyelid movement. There can be one eye sensor camera 406 that monitors only one eye, one eye sensor camera 406 with a wide angle that can monitor both eyes or two cameras with one to monitor each eye. There can also be multiple cameras, to monitor different areas of each eye (e.g. eye response sensors tracking pupil features and corneal reflection surfaces). The eye sensor video camera 406, can be positioned anywhere around the eye, and can utilize visible or invisible light. In one embodiment, the system shown at 440 further comprises an illumination source 530 to help illuminate the eyes of the person. This illumination source 530 could project infrared light, near infrared light, or visible light in the direction of the person's eyes to help improve the sensitivity of the eye sensor 406 and make it less sensitive of other light sources, which may produce noise and/or glint.

FIG. 1 illustrates one example of a faceguard-based ocular performance measuring system 440. In this embodiment, the faceguard frame is shown at 442. The faceguard frame 442 could comprise a plurality of rigid structural members with at least one aperture for facilitating human vision through the faceguard. The faceguard frame 442, could comprise materials such as metal, carbon fiber, plastics, glass fiber, or any combination of these materials or others capable of being understood by anyone skilled in the art. The faceguard frame 442, could comprise eye sensing elements and/or transducers for detecting and measuring eye movements and a head orientation sensing element/transducer and circuitry to the electronic elements such as:

the head orientation sensor shown at 404, connected to the orientation sensor signal processor 412;

the eye-tracking digital video camera 406, connected to the eye camera video processor 414; and the central processing unit 418, memory unit 420, and interface/communication unit 422 for communicating with an external device 424.

The faceguard-based system 440, of FIG. 1 could have other sensors that interface with the electronic module 410. As an example, the faceguard-based system 440, of FIG. 1 might have a forward-facing camera 408, that communicates with a forward-facing camera interface 428, in the electronic module 410. The forward-facing camera 408, can be responsive to the eye sensors to measure the ocular performance. In this case, the central processing unit 418, or the external device 424, could combine the information from the head orientation sensors 404, the eye-tracking digital video camera 406, and the forward-facing camera 408, to determine one of the ocular performance parameters described herein.

Further referring to FIG. 1, the faceguard-based system 440, could also have a forward-pointing visual cue projector, shown at 430. This visual cue projector 430, could comprise a light source, and that light source could comprise a light emitting diode (LED) or a laser. The light source can project a cue 434 (visual object or visual element) onto a surface 432. The surface 432 could be any available surface, examples of which might be an area of open or cleared ground nearby, or a subdued solid wall surrounding the field, positioned approximately 3 meters or 10 feet from the user. The user's ability to maintain his/her gaze on this projected cue 434 (visual object or visual element) on the surface 432 can be used for calibration or testing of the ocular parameter being measured. For example, the projected visual cue 434 could remain stationary when the user's head moves. The system could also be configured so that the visual cue 434 moves on the surface 432 and the user's ability to follow this movement is measured. The visual cue projector 430 could be controlled through a cue projector interface, shown at 436, that is part of the electronic module 410. The visual cue projector 430 could be responsive to the central processing unit 418.

In humans, the horizontal semicircular canal and the utricle both lie in a plane that is slightly tilted anterodorsally (30 degrees) relative to the nasal-occipital plane. When a person walks or runs, the head is normally declined (pitched downward) by approximately 30 degrees, so that the line of sight is directed a few meters in front of the feet. This orientation causes the plane of the horizontal canal and utricle to be parallel with the earth and perpendicular to gravity. When the head is tilted downward 30 degrees and doing horizontal testing, the lateral semicircular canals are maximally stimulated. Hence looking downward several meters ahead at a surface is desired for testing. Therefore, it is desirable to have the cue projector 430 configured to project the visual cue 434, several meters in front of the user, at an angle approximately 30 degrees downward anterodorsally.

In another embodiment sensors can be attached to the faceguard for measuring the characteristics of an impact. These sensors can be located in preferred positions most likely to detect linear and tangential impacts, relative to the rotational center of the wearer's head. As an example, sensors used to measure linear impacts can be placed in the frontal area and tangential impacts can be placed in the lateral or temporal location.

Embodiments of the present invention could be implemented with eye trackers (also described herein as eye sensors), shown for example at 406 in FIG. 1, which are not video cameras. Examples of non-video camera eye trackers can include electromyography trackers and electromagnetic trackers. In another embodiment, the eye sensor, 406, is an image sensor capturing single images or frames from the sensor greater than 90 frames per second.

The faceguard-based system 440, of FIG. 1 could have other sensors that interface with the electronic module 410. The faceguard-based system 440, could have an attached display and display interface. However, a display might be difficult for the person to use when active and therefore could be removable and used only when testing is performed. In an alternative embodiment, the faceguard system 440 of FIG. 1 could comprise a detachable drop-down display (not shown) in addition to the head orientation sensor 404, and an eye tracking video camera, 414. The drop-down display unit could be attached to the faceguard to provide visible images for ocular performance testing as described herein. In another embodiment, the detachable drop-down display (not shown) could perform multiple functions including: (a) providing the visual elements required for measuring the ocular parameters; (b) a head orientation sensor; and (c) an eye tracking video camera, all located within the drop-down display unit. This drop-down display unit could be a smart phone. This drop-down display unit would have its own power source and could be configured for being responsive to other sensors, such as the forward-facing camera and/or impact sensors.

Figure 2:
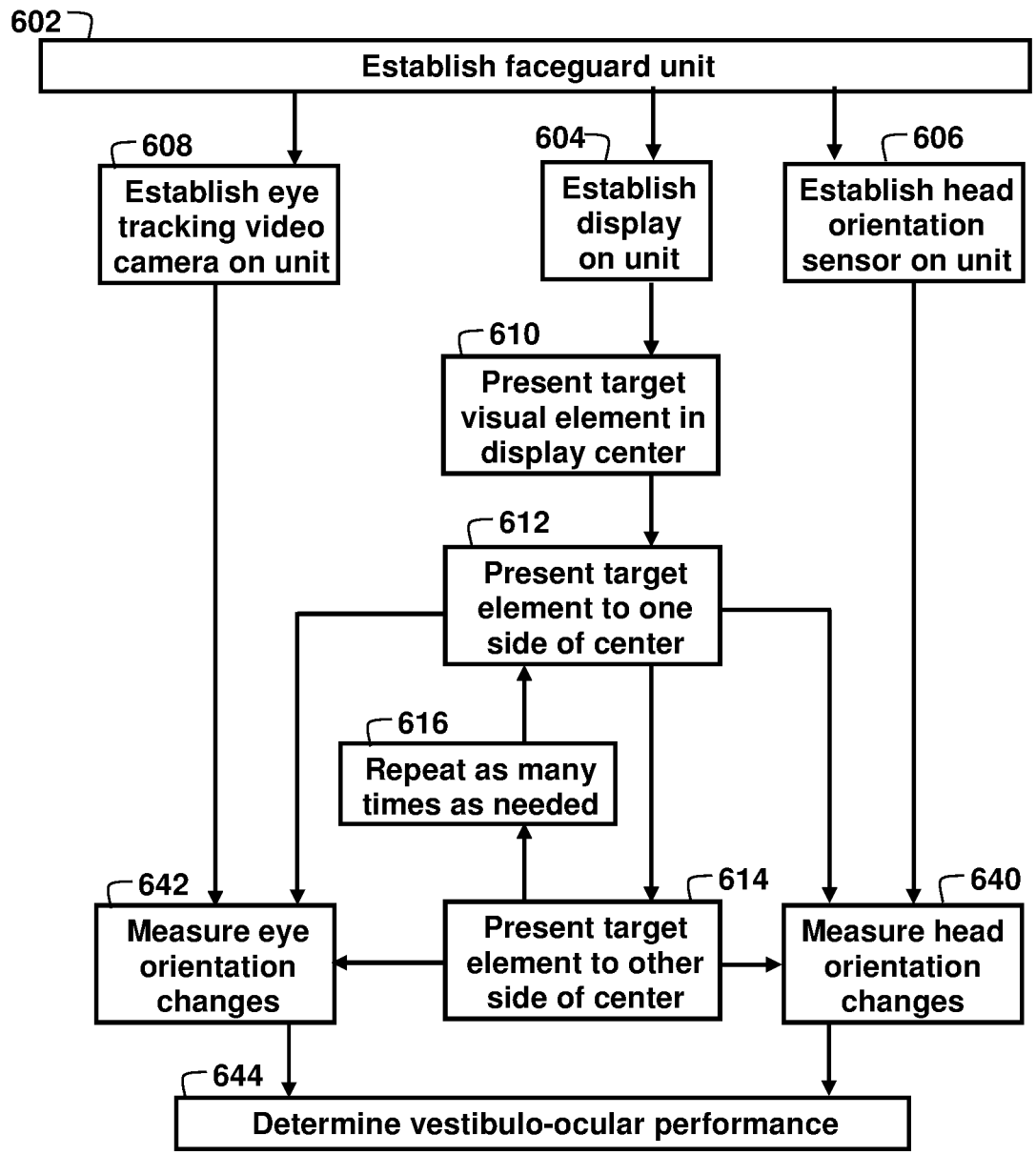
FIG. 2 shows an ocular performance calibration test method.

FIG. 2 shows an example of a vestibulo-ocular performance calibration test that can be implemented using a head-worn, or helmet affixed, faceguard unit. This test comprises the following configuration and steps:

Establishing a faceguard unit 602 that comprises a forward-facing visual cue projector (such as 430 in FIG. 1), a head orientation sensor 606, and an eye tracking video camera 608 and a visual cue (434 in FIG. 1), from the visual cue projector 430, in the background or a visual element in the natural scene on the surface (432 in FIG. 1), which the user can focus upon.

Head: In this test, the subject is asked to keep his/her head motionless or the head is constrained to keep it motionless. The head orientation sensor 606, is used to verify that the head is stationary.

Eyes: The subject is asked to track a visual cue 434, in the foreground or natural scene, by moving his/her eyes. The eye sensor (typically a video camera) measures the subject's eye movement 642, as visual elements are displayed.

Cue on Surface: The background area on the surface 432 behind the projected visual cue 434, is subdued, plain, solid, and/or non-distracting. In this test, the background can be similar to the background that has been used in prior art VOR testing in which the subject is asked to look at a plain background while a bright white circular dot (the cue 434) projected on surface 432. In another embodiment of this test, cue 434 could be visually enhanced for better image or target eye fixation. The cue 434 can then behave in the following way:
1. The cue 434 is initially projected to be viewed centrally 610.
2. It is then projected to be viewed off center on a first side (left or right) from the center of the user's gaze, as shown at 612. This is typically about 20-25 degrees off center.
3. It is then projected to be viewed off center on an opposite (or second) side of the user's gaze, as shown at 614. This is also typically about 20-25 degrees off center.
4. This process of projecting the cue 434 on one side and then on the opposite side is repeated as many times as needed, as shown at 616.
5. This test can be conducted in the vertical, as well as the horizontal direction.

Processor: The processor in the faceguard system then compares eye movement to timing and appearance/disappearance and location of the cue 434 to determine vestibulo-ocular performance 644. Performance could be measured as accuracy, gain, phase, symmetry, velocity, saccades, and/or visual acuity.

Figure 3:
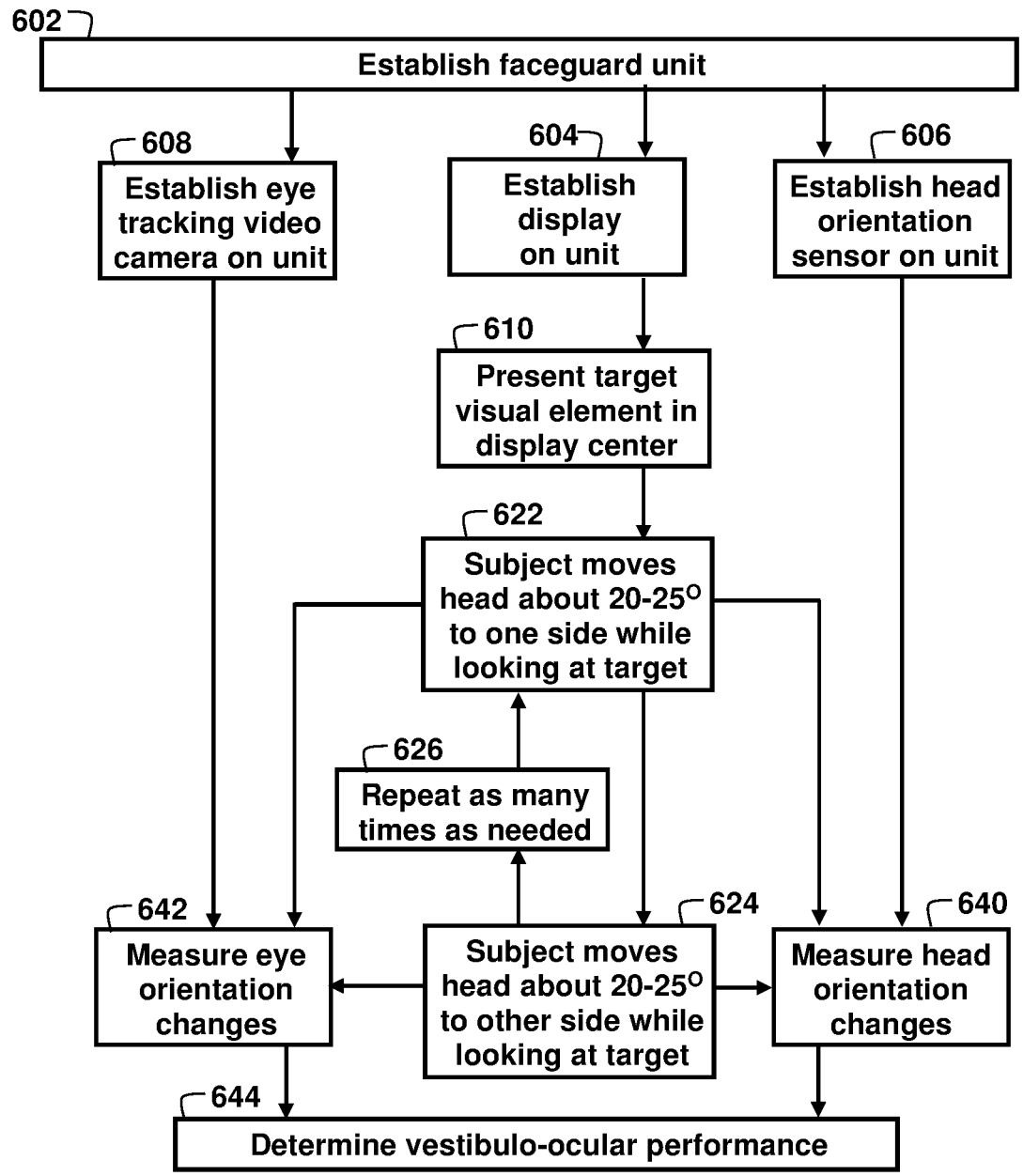
FIG. 3 shows a static active ocular performance test method.

FIG. 3 shows an example of static active vestibulo-ocular performance testing that can be implemented in a faceguard unit. This test comprises the following configuration and steps:

Establishing a faceguard unit 602 that comprises forward-facing visual cue projector (such as 430 in FIG. 1), a head orientation sensor 606, and an eye tracking video camera 608.

Display: In this test, the cue (434 in FIG. 1) is static—neither the surface (432 in FIG. 1) nor the cue 434 moves or changes in any way. The surface 432 comprises a subdued background and the cue 434 is a projected centered white circular dot, similar to what was described with reference to the test shown in FIG. 2.

Head: In this test, the subject is asked to actively move his/her head each time he/she is given a prompt. The head should typically move about 20-25 degrees off center about a vertical axis (i.e. left or right). The head orientation sensor measures changes in head pitch, roll, and/or yaw 640.

Eyes: The subject is instructed to keep his/her eyes focused on the target visual element as the head moves. The eye sensor (typically a video camera) measures eye movement 642, relative to head movement 640.

Prompts are provided to tell the subject when to move the head. These prompts can be audio prompts. The prompts could be haptic (i.e. vibration on the side of the person's head). The prompts could be visual (i.e. change of color or intensity of the visual target element of interest). The prompts are typically timed randomly so the subject doesn't try to anticipate the timing.

The test sequence is as follows:
1. The subject is instructed to move the head about 20-25 degrees in one direction when a first prompt is given, and to hold the head in this new position 622.
2. The subject is instructed to move the head back about 20-25 degrees when the second prompt is given 624.
3. The subject is instructed to move the head in the first direction a second time when the third prompt is given.
4. The process is repeated as many times as needed 626.
5. This test can be conducted in the vertical, as well as the horizontal direction.

Processor: The processor in the faceguard system then compares head and eye movement to timing and location and/or appearance/disappearance of cues 434, and the location of these visual elements to determine vestibulo-ocular performance 644. Performance could be measured as accuracy, gain, phase, symmetry, velocity, saccades, and/or dynamic visual acuity.

Figure 4:
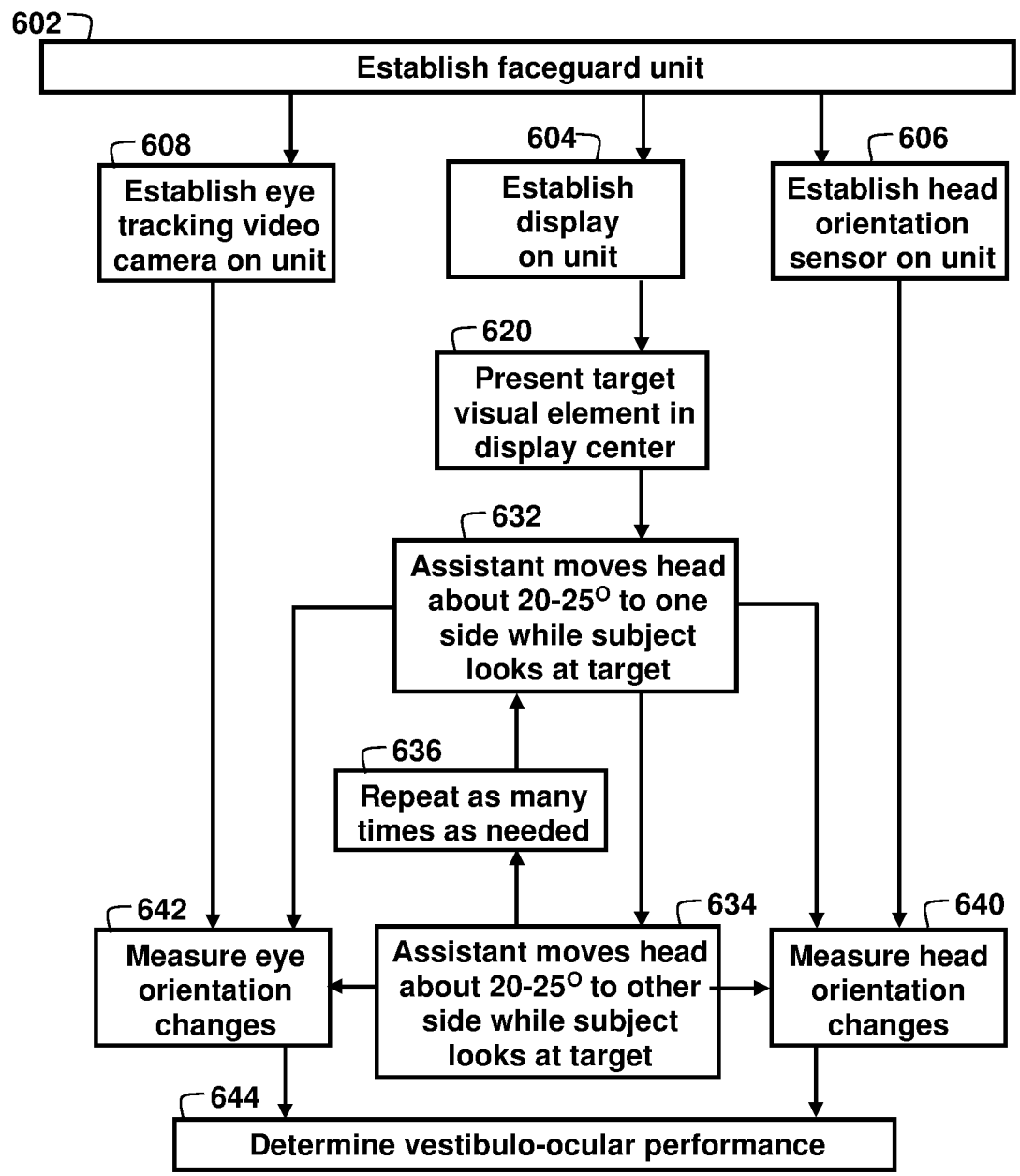
FIG. 4 shows a static passive ocular performance test method.

FIG. 4 shows a static passive vestibulo-ocular performance test that can be implemented with a faceguard unit. This test comprises the following configuration and steps:

Establishing a faceguard unit 602 that that comprises forward-facing visual cue projector (such as 430 in FIG. 1), a head orientation sensor 606, and an eye tracking video camera 608.

Display: In this test, the cue (434 in FIG. 1) seen is the same as for the test described with reference to FIG. 2 and FIG. 3, with a target visual element presented in the center 610.

Head: In this test, the assistant holds the subject's head and moves it about 20-25 degrees each time 632. The head orientation sensor measures changes in head pitch, roll, and/or yaw 640.

Eyes: The subject is instructed to keep his/her eyes focused on the cue 434 as the head moves. The eye sensor (typically a video camera) measures eye movement 642 relative to head movement 640.

The test sequence is as follows:
1. The assistant moves the subject's head about 20-25 degrees in one direction and then holds it in this new position 632.
2. The assistant then moves the head back in the opposite direction, 20-25 degrees and holds it 634.
3. The assistant moves the head in the first direction a second time.
4. The process is repeated as many times as needed 636.
5. This test can be conducted in the vertical, as well as the horizontal direction.

Processor: The processor in the faceguard system then compares head movement and eye movement to determine vestibulo-ocular performance 644. Performance could be measured as accuracy, gain, phase, symmetry, velocity, saccades, and/or dynamic visual acuity.

There can be many additional embodiments of the ocular performance tests described with reference to FIG. 2, FIG. 3, and FIG. 4. Some of these embodiments can include combinations of the variations listed here:
a. The cue (434 in FIG. 1) can be any other shape, size, or coloring or have any other features capable of being understood by anyone skilled in the art. Examples of these variations in the target visual element could include:
   A different shape (such as a shape comprising a cross hair);
   Different contrast, either more or less;
   Different intensity;
   Different size;
   Different focus, either more in-focus or out of focus;
   Having one or more features in the visual element that move relative to the rest of the visual element;
   Different depths;
   The appearance of a natural object (such as a baseball, a basketball, or a bird); and/or;
   Any combination of any of the above.
b. The test shown in FIG. 3 and/or FIG. 4 could be run with the cue (434 in FIG. 1) not being stationary. This would make the overall test more similar to a natural environment in which the head, the eyes, and the visual world are all moving relative to one another and relative to a stationary reference frame at all times. The cue 434 could:
   Move with the head movement;
   Move contrary to the head movement;
   Move perpendicular to head movement; and/or
   Move in any random pattern not associated with head movement
c. The surface (432 in FIG. 1) (traditionally subdued, plain, solid, and/or non-distracting), visualized through the face guard, projected by the cue projector (430 in FIG. 1) or seen through a display mounted to the faceguard unit, could be presented any surface 432 understood by anyone skilled in the art. Examples of variations of the surface 432 can include embodiments in which the background is more natural and similar to actual scene and/or any of the variations in the following list:
   The surface 432 can be completely static;
   The presentation of the cue 434 on the surface 432 can have moving and/or flashing elements;
   The presentation of the cue 434 on the surface 432 can be enhanced with auditory distractions consistent with the imagery being displayed;
   The presentation of the cue 434 on the surface 432 can be in or out of focus;
   The presentation of the cue 434 on the surface 432 can be low intensity/contrast or high intensity/contrast relative to the target of interest;
d. The face guard system can be responsive to a human generated input signal including an auditory human input signal or a haptic human input signal. The faceguard can be configured to have an alerting signal for the user to turn the head or begin the testing. This signal can occur randomly and therefore resemble the static passive testing described previously, without the need for an assistant.

Visual acuity, visual fixation ability, DVA (dynamic visual acuity), KVS (kinetic visual acuity), FFS (foveal fixation stability), and/or RIS (retinal image stability) can be tested using a system and method similar to the vestibulo-ocular performance (VOP) test shown in FIG. 3 and/or FIG. 4. The following are the main steps of a DVA, FVS, FFS or RIS test performed in this way using a faceguard:

Step 1. Perform a routine vision test by presenting a Snellen chart, or something similar, using the display of the faceguard unit. This is needed to establish a baseline visual acuity in a static environment. This static test does not necessarily need to be done with a Snellen chart (the standard chart used by optometrists and ophthalmologists), it could also be done by asking the subject to identify characters of various sizes, positions, and/or locations.

Step 2. The subject is presented a cue (434 in FIG. 1), such as a number or letter, in the visual field center in a manner similar to step 610 of FIG. 3, but in the case of a DVA or FVS test, the target visual element also comprises a character that the subject must identify.

Step 3. The presentation of the cue 434 in the center of view on the surface 432 changes at random times while the subject is performing the steps described at 622, 624, and 626 in FIGS. 3 and/or 632, 634 and 636 in FIG. 4.

Step 4. The subject speaks out the character observed each time it changes.

A faceguard system can also be used for positional testing. The subject could be asked to turn the head left, right, lie supine, while supine head turns right, head turns left, then turn the body (roll) right and turn the body (roll) left. During each positional change, the eyes are tracked using the faceguard system to look for abnormal eye movements. If a visual cue (such as 434 in FIG. 1) was visible during this testing, the nystagmus would be suppressed. Visual elements in this instance should not have defining characteristics that might enable eye fixation.

A subject can be tested for BPPV using the method shown in FIG. 4 with the assistant moving the head in a specific pattern that allows the individual semicircular canals to be tested. Note that this means the head is not moved the 20 degrees side-to-side, but is instead moved based on standard protocol for the specific semicircular canal being tested.

Figure 5A:
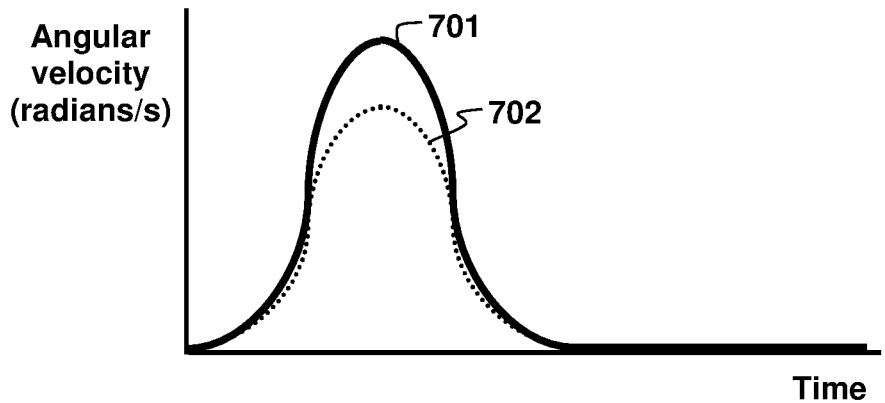
FIG. 5A shows a vestibulo-ocular gain measurement.
Figure 5B:
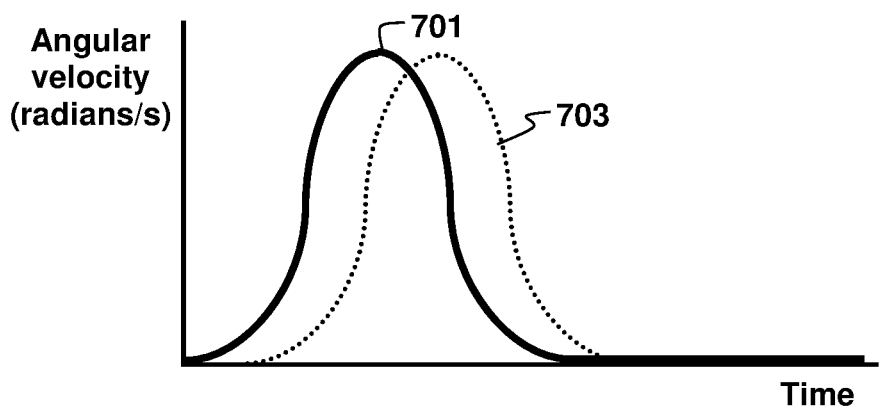
FIG. 5B shows a vestibulo-ocular phase measurement.
Figure 5C:
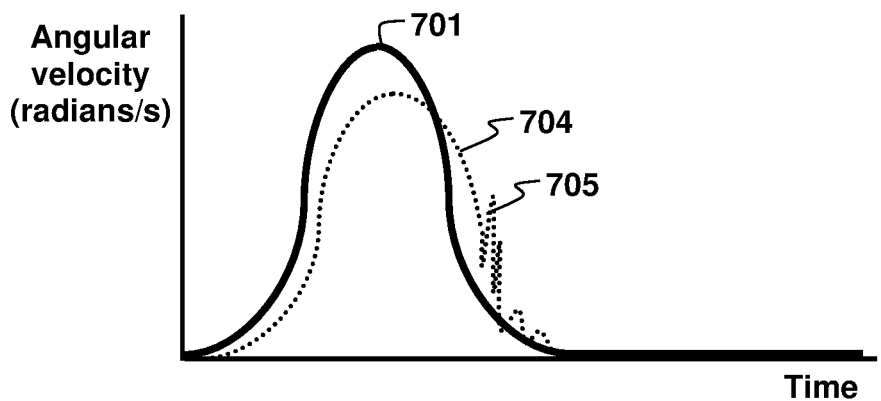
FIG. 5C shows ocular saccades.

FIG. 5A, FIG. 5B, and FIG. 5C provide graphs of time versus angular velocity that show how ocular response to a vestibular input can be measured. In these figures, the input is a rotation of the head, which is shown as the solid line at 701. This head rotation information would typically be measured using the head orientation sensor 404, that has been shown in FIG. 1. The output is the eye response to the head rotation, which is shown as the dotted line at 702, 703, and 704, and would typically be measured using the eye sensor, which is typically an eye tracking digital video camera 406, such as that shown in FIG. 1. The actual eye response is in the direction opposite of the head rotation, 701, but it has been plotted in the same direction to make it easier to compare the input and output of a person's vestibulo-ocular system. In FIG. 5A, the velocity of the eyes is slower than that of the head, which results in a gain of less than 1.0 (i.e. a loss of amplitude 702). In FIG. 5B there is a delay between the rotation of the head and the rotation of the eyes, which results in a phase lag, 703. In FIG. 5C, the eye rotation also lags the head rotation as shown at 704, but is caught up by saccades 705, near the end of the rotation.

Figure 6A:
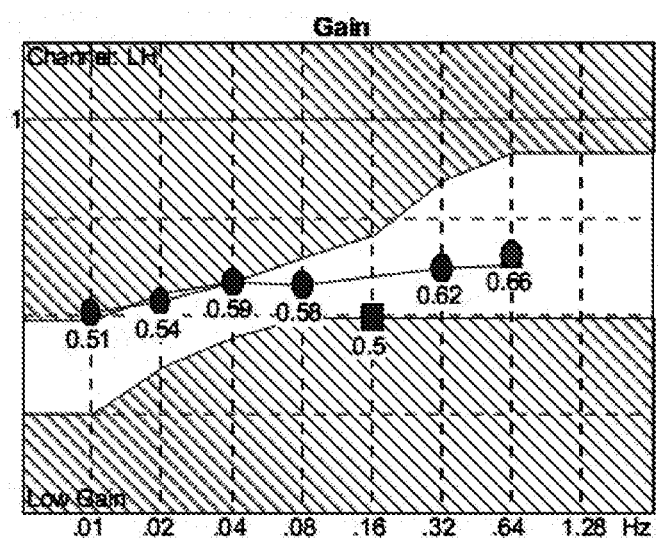
FIG. 6A illustrates an example of the left eye gain of a healthy person's vestibulo-ocular response to motion between 0.1 Hertz and 1.28 Hertz.
Figure 6B:
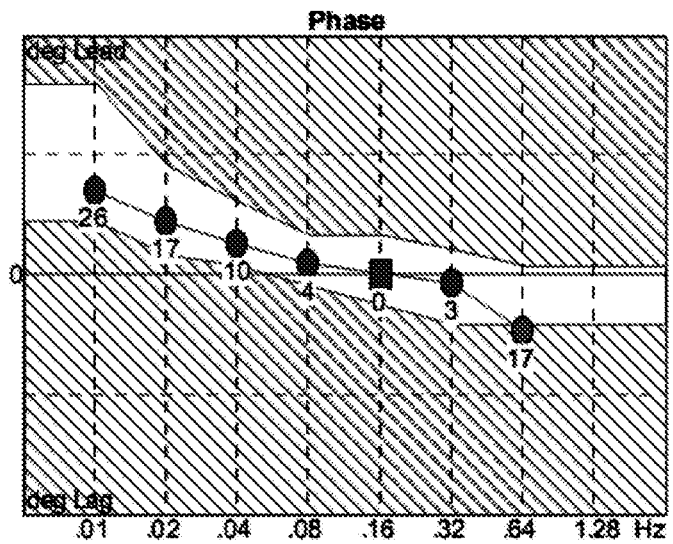
FIG. 6B illustrates an example of the phase lead and lag for a health healthy person's vestibulo-ocular response to motion between 0.1 Hertz and 1.28 Hertz.
Figure 6C:
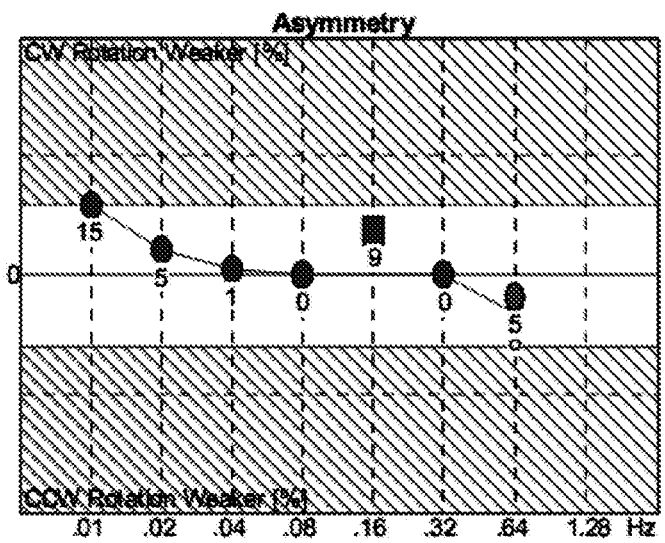
FIG. 6C illustrates an example of the asymmetry readings between counterclockwise and clockwise horizontal rotation of a healthy person's vestibulo-ocular response to motion between 0.1 Hertz and 1.28 Hertz.

The measures shown in FIG. 5A, FIG. 5B, and FIG. 5C, can be plotted at different frequencies and compared between the left eye and the right eye to create the plots shown in FIG. 6A, FIG. 6B, and FIG. 6C, which illustrate some typical eye responses to oscillation of a healthy person's head (e.g. vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 6A shows the gain at these frequencies, FIG. 6B shows the phase lead and lag at these frequencies, and FIG. 6C shows the relative symmetry (or asymmetry) between clockwise and counterclockwise oscillations. It should be noted that 0.1 Hertz to 1.28 Hertz is typical for the range of frequencies being used by prior art VOR testing systems. The embodiments described in this disclosure can include any frequency in the range of 0.01 Hertz (1 cycle every 100 seconds) to 15 Hertz (approximately 15 cycles every second).

FIG. 7A, FIG. 7B, FIG. 8, FIG. 9, FIG. 10, and FIG. 11 relate to targets or visual elements that could be visualized or projected to facilitate measurement and/or improve ocular performance parameters such as vestibulo-ocular reflex function, visual pursuit, vergence, DVA, or other ocular parameters discussed herein. These targets or visual elements can be designed to enhance the eye fixation on the displayed image when the head is motionless and the visual element is in motion. These targets or visual elements could also be designed for when the head is in motion and the visual element is motionless or when both the head and the visual element are in motion. In embodiments of the invention, the visualized or projected targets or visual elements can be static in a position or location or the displayed targets or visual elements can be dynamically changing in position, depending on the specific test being performed or rehabilitation method being used. The targets or visual elements, upon which the eyes are attempting to focus, can be of a variety of colors, sizes, shapes, and forms. They can change in color, size, shape, and form. They can contrast with other items being displayed to be more or less dominant in order to provide visual weight to enable fixation. These targets or visual elements can use specific colors with more saturation and can change in scale and proportion, all in an effort to draw the fovea toward a specific point of fixation on the target or visual element. Generally, it is important to have some small point of focus on the visual element to lessen the microsaccades and enhance the fixation ability. These same targets or visual elements can be used for any oculomotor or ocular performance testing including VOR re-training when a VOR abnormality exists.

The ideas expressed in the previous paragraph can best be explained by looking at some examples. FIG. 7A shows an example of a target or visual element in the form of a soccer ball 902. This soccer ball could be part of an existing scene viewed through a faceguard, or it could be an image projected from a light source attached to the faceguard, or projected on a display, attached to a faceguard. The soccer ball could be spinning, which might make the pattern on the ball distracting. FIG. 7B shows the visual element (soccer ball) of FIG. 7A that has been altered by defocusing the ball 904 and superimposing a target in the form of a crosshair 906, that is more precise for the eyes to focus on. It would be more accurate fixation for the eyes to focus on the center of the cross-hair element shown in FIG. 7B than the element shown in FIG. 7A due to the shape, size, contrast, and suppression of the pattern on the ball. Although this example has been done using a black and white image, color and color contrast can be more effective. For example, the visual element seen through the faceguard or with an attached faceguard display, could be a red colored ball. Within the center of the red ball, a yellow circle can be present with a small black dot located in the center. This strongly contrasted central focal point could help the eye focus on a specific point and lessen the "eye scanning" while undergoing any ocular performance measurement such as VOR testing or VOR re-training. In another example, the element being viewed can be in the shape of a familiar object, such as a basketball, football, helmet or object used in one's occupation. It can also have a centered focal point, created by high contrast and high color saturation compared to the surrounding background to maintain the foveal fixation duration attractiveness and lessen microsaccades.

FIG. 8 shows a scene that can be used for optokinetic testing. In traditional optokinetic testing, a person's head is motionless while seated inside a moving drum with alternating black and white vertical lines or alternatively, a hand-held drum, with alternating black and white vertical lines, is placed in front of the person. The drum is slowly rotated. The alternating lines induce nystagmus and cause visually induced motion sickness. The movement of the eyes is measured as the drum rotates left and then right. Measurements can be at different drum speeds. This same test can be performed using a faceguard by creating a visual image that includes elements that work just like the vertical lines in the drum. Examples of natural scenes that are similar to the drum with lines can include examples such as being seated in a car and watching a train go by or driving and watching the telephone poles move by, such as the scene 910 shown in FIG. 8. Similarly, flying objects can be visualized as moving across the visual field or along another plane of motion beside the person. These visual elements can also change in size, color or other dimensions, as the person gets closer to the object or further from the visual element. Motion can occur in any direction or depth relative to the person, as the eye movement is being assessed and measured.

Figure 9:
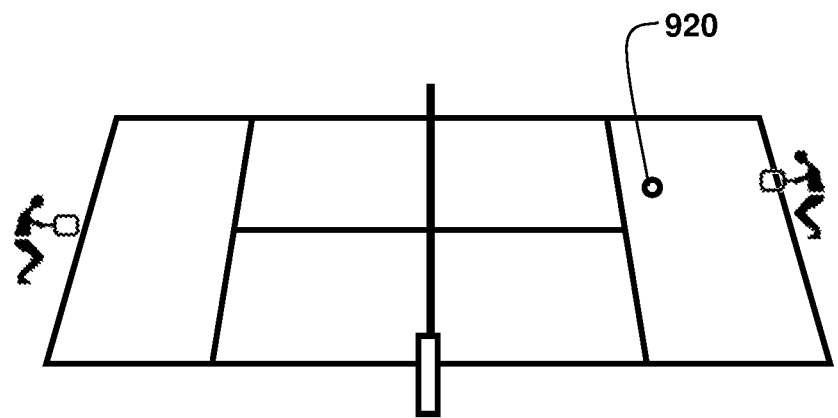
FIG. 9 shows a scene that can be used for testing eye-tracking performance.
Figure 10:
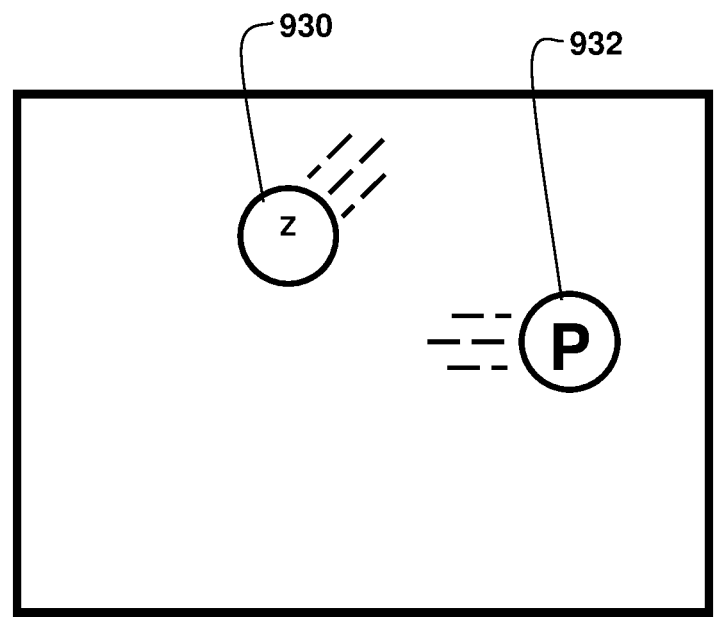
FIG. 10 shows a scene that can be used for dynamic visual acuity testing.
Figure 11:
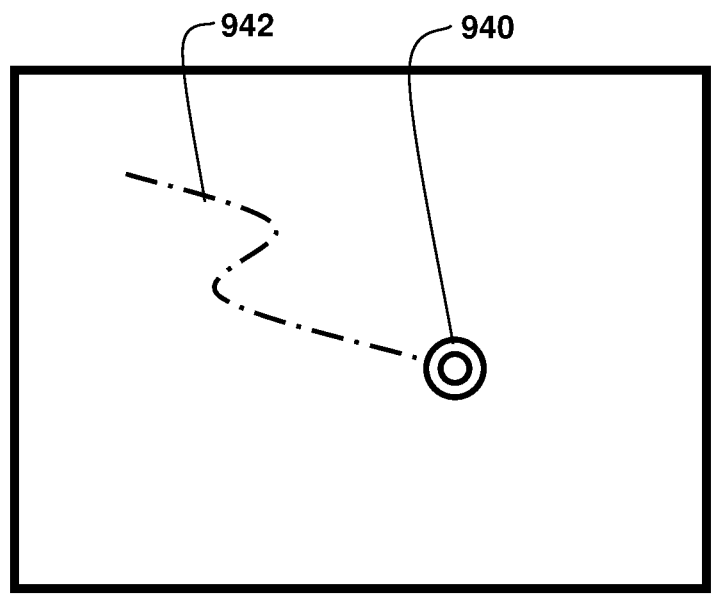
FIG. 11 shows a scene that can be used for scan path tracking.

FIG. 9, FIG. 10, and FIG. 11 illustrate other visual scenes, which can be seen through the faceguard, or projected from a light source attached to the faceguard, or used with a display attached to a faceguard. These visual scenes can be used for ocular performance testing such as VOR, DVA, visual pursuit, and/or fixation ability testing. These scenes can include a test environment comprising natural background features combined with a visual element or target whose shape, color, size, motion, depth, or other attributes have been selected or added to facilitate testing of vestibulo-ocular performance. FIG. 9 shows an example of a scene which illustrates what this type of ocular performance testing, such as with visual pursuit, DVA and/or VOR might look like. In the example shown in FIG. 9, the static scene can be a tennis court and the moving target is the tennis ball 920. The visual element (e.g. tennis ball) can remain motionless in the center, surrounded by a static court with 2 players on each side. The individual being tested would rotate his/her head in the horizontal and vertical plane while focusing on the visual element. Alternatively, as the person focuses on the static visual element in front of the player on one side of the court, it can suddenly become dimmed and re-appear on the other side of the court. The individual being tested is required to rotate the head each time the visual element reappears. This action can occur in a back and forth manner until the measurement is complete. For more complex testing, the surrounding courtside scene can be filled with fans who are in motion. As another example, if the VOR is being tested on a basketball player, the dynamic background features may be a basketball court surrounded by fans, who are yelling and moving and the visual element (e.g. basketball) may suddenly appear in the hands of a player on one side, then dimmed or removed, and then alternatively appear in the hands of another player on the other side, requiring the individual being tested to move the head in a horizontal manner. DVA measurement can also be performed with dynamic changes of the target or visual element of interest, requiring the person to identify characteristics of the element while it is in motion and the person is in motion and comparing this to the SVA prior to the onset of the DVA test. FIG. 10 shows letters that could be superimposed onto the moving element (such as the tennis ball in FIG. 9) to test DVA. The target visual element 920 in FIGS. 9, 930 and 932 in FIG. 10, or 940 in FIG. 11 could move in different trajectories, in different depths, the letters could be of different sizes, and the ball could move at different speeds and accelerations to provide a meaningful test as shown by comparing visual element 930 with visual element 932. The targets can be static or rapidly moving is a specific plane or scan path for (such as watching a tennis ball move across the court or with tracking tests that have a rotating target visual element) depending on the ocular parameter being tested.

DVA testing could be performed with lettered optotypes and as the head rotates back and forth, the letters can rotate in position. Alternatively, numbers can be used as well as other familiar images of objects. The images can also be native or natural to the background environment. As the head rotates back and forth, the target or visual element is more difficult to visualize. If there is a VOR abnormality, for example the eyes will not be able to focus on the target or visual element of interest and will subsequently have less fixation and more errors in identifying a visual element. Measurement can also be performed with the visual element stationary and the head in motion or both the visual element and head in motion, which would be more realistic with everyday experiences. Static visual testing (SVT) can be performed to obtain a normal visual test. The visual acuity can be obtained, while the head and the visual element, or optotype being seen through the faceguard or from a projected light 604, or with the use of an attached display, are both motionless. Similar to a standard eye exam, a faceguard system as described herein can measure a person's static visual acuity (SVA), a component of DVA testing, by asking a person to identify a multitude of images or optotypes (letters, symbols, characters, figures of different sizes, shapes, orientation).

Visual pursuit testing can be performed with similar targets or visual elements of interest as have been described previously. Smooth pursuit testing has traditionally been performed with the head motionless and the eyes following a moving light or finger moving across a visual field. FIG. 11 shows a scene that can be used for scan path tracking. An enhanced target visual element 940, can travel across the visual scene along a specific path 942, while the measured eye movement follows the visual element. The path of these visual images or elements can assume any pattern, such as a zigzag, a saw toothed, or a square wave, or have a scan path that is snake-like, curved, circular, sinusoidal or rotational to provide a realistic and natural method of assessment of visual pursuit.

Figure 12:
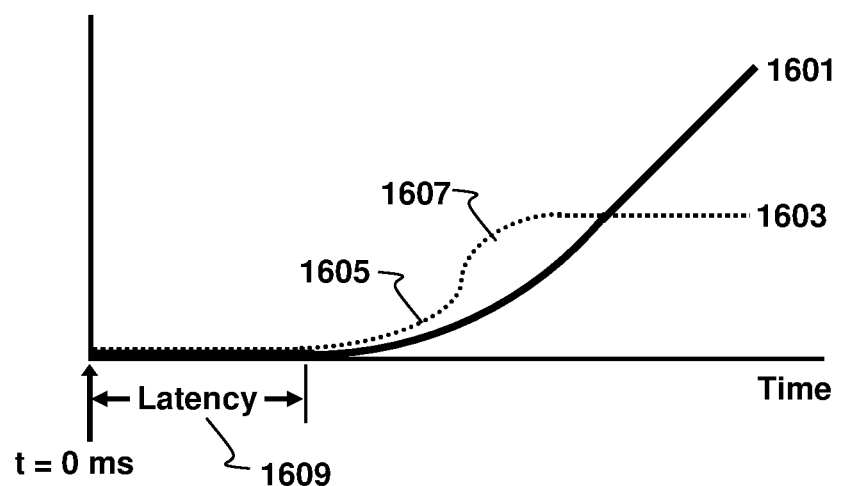
FIG. 12 shows the relationship between target movement, eye position, eye velocity, and eye acceleration for smooth pursuit.

FIG. 12 shows the relationship between target movement, eye position 1601, eye velocity 1603, and eye acceleration for smooth pursuit. The time when the target is moved is identified as t=0 ms. The eye position 1601, and eye velocity 1603, can then be tracked as a function of time. Latency, 1609, is the delay from the time the target moves to the time the eye starts to move. Then the eye velocity 1603, will first accelerate 1605, and decelerate 1607, until the eye velocity 1603, matches the target velocity.

Figure 13A:
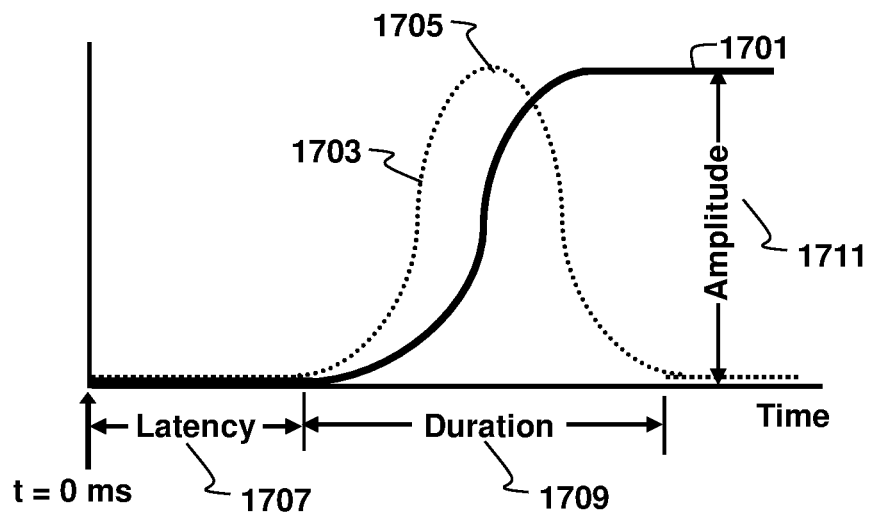
FIG. 13A shows the relationship between target movement, eye position, and eye velocity for a saccade.
Figure 13B:
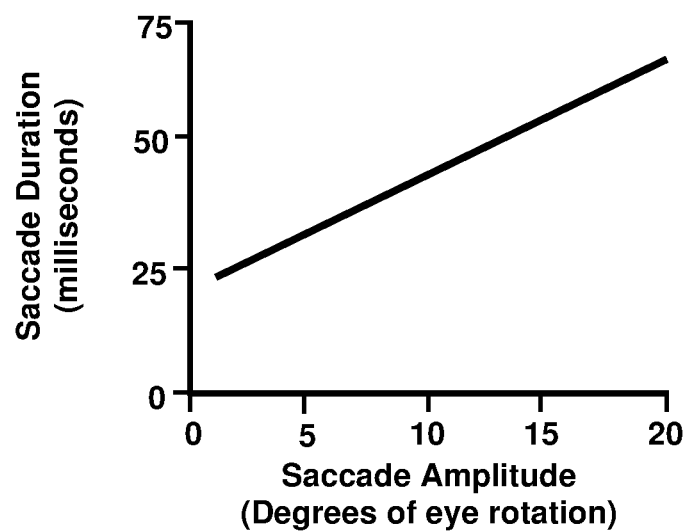
FIG. 13B shows the typical relationship between saccade amplitude and saccade duration.

FIG. 13A shows the relationship between target movement, eye position 1701, and eye velocity 1703, for a saccade. The time when the target is moved is identified as t=0 ms. The eye position 1701, and eye velocity 1703, can then be tracked as a function of time. Latency, 1707, is the delay from the time the target moves to the time the onset of a saccade. As shown, the saccade eye velocity, 1703, increases, reaches a peak velocity 1705, and then returns to zero. The length of time from the start to the end of this velocity curve is called the saccade duration 1709. The saccade eye position 1701, changes during this duration 1709, to reach a new position that differs from the initial eye position by a distance that can be defined as a saccade amplitude 1711. FIG. 13B shows the typical relationship between saccade amplitude and saccade duration.

Note that any of the testing described for any of these embodiments can be done with static targets or visual elements being viewed, or with dynamic targets or elements. The images or elements viewed may be familiar objects, such as balls, or objects more familiar to one's occupation or preferred activities. The visual target or visual elements may be displayed in a manner that is native or natural to the background.

Figure 14:
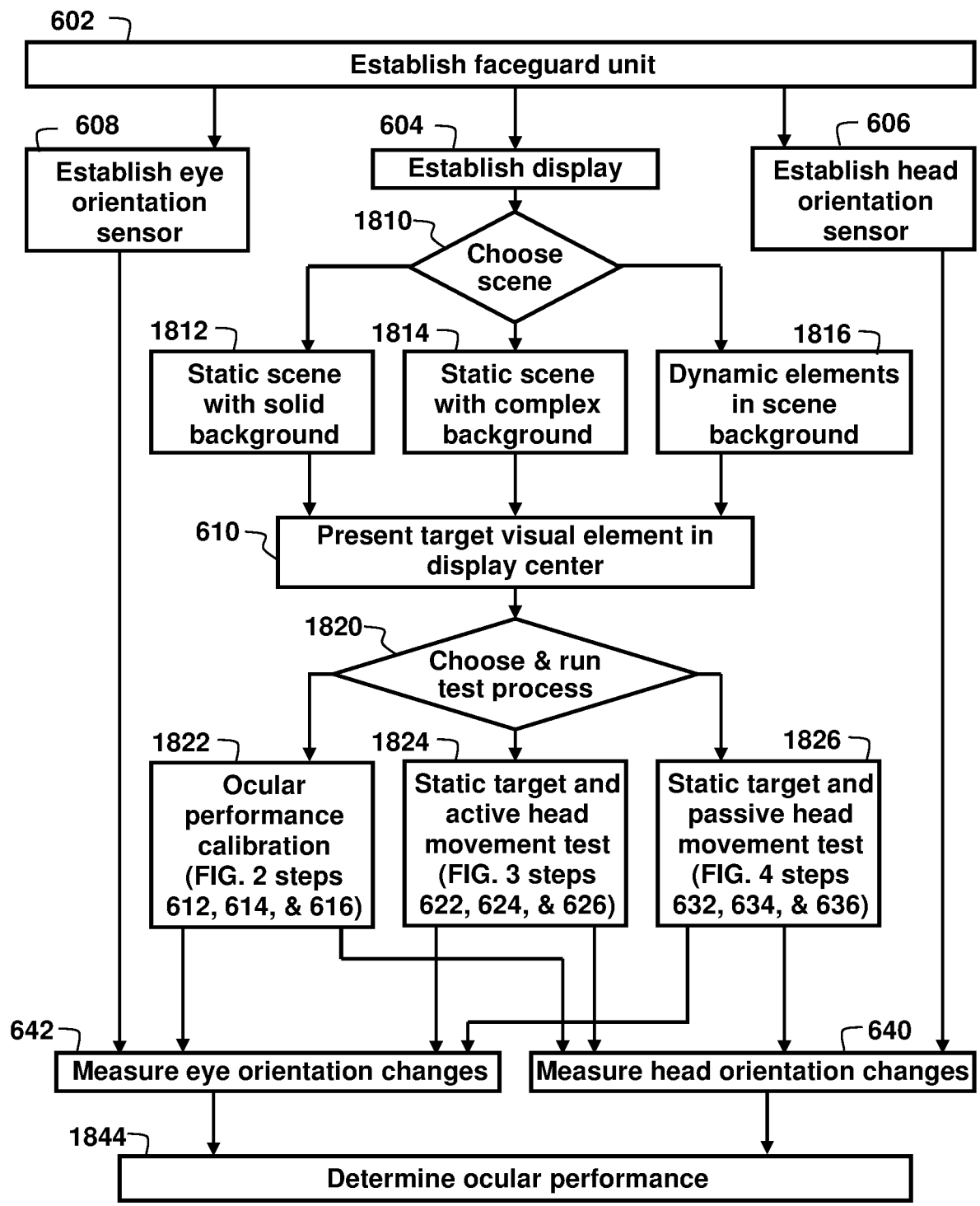
FIG. 14 shows a generalized method for ocular testing using a faceguard unit.

FIG. 14 provides a more generalized embodiment of the system and method that was presented in FIG. 2, FIG. 3, and FIG. 4. Referring to FIG. 14, the faceguard unit that was shown at 602, in FIG. 2, FIG. 3, and FIG. 4, is also shown in FIG. 14. The eye tracking video camera on the unit that was shown at 608, the display 604 (which could be the visual cue, 434, of FIG. 1 on the surface 432 of FIG. 1, or it could be a flip-down display as described previously), and the head orientation sensor 606, in FIG. 2, FIG. 3, and FIG. 4 is also shown in FIG. 14. As shown in FIG. 14, the process can further include the step of choosing a scene 1810, and the choices of scenes can comprise a static scene with a solid background 1812, a static scene with a complex background 1814, and/or scene with dynamic (i.e. moving) elements in the background 1816. The process shown in FIG. 14 includes the step of visualizing or projecting a target visual element in the center of the scene or 610 and 620, just like the processes shown in FIG. 2 (steps 612, 614, and 616), FIG. 3 (steps 622, 624, 626), and FIG. 4 (steps 632, 634 and 636).

Further referring to FIG. 14, the method can comprise the step of choosing which ocular test to run on a subject as shown at 1820, and the choices can include ocular performance calibration 1822, static target and active head movement testing 1824, and/or static target and passive head movement testing 1826. Each of these three test processes (1822, 1824, and 1826) involves measuring eye orientation changes 642 and head orientation changes 640, just like the processes shown in FIG. 12, FIG. 13, and FIG. 14. These ocular performance parameters can include any of the following parameters that have been discussed in other parts of this disclosure, including but not limited to:

(a) vestibulo-ocular reflex;
(b) pupillometry;
(c) saccades (overt and covert);
(d) visual pursuit tracking;
(e) vergence (convergence and divergence)
(f) eyelid closure;
(g) dynamic visual acuity;
(h) dynamic visual stability;
(i) retinal image stability;
(j) foveal fixation stability;
(k) focused position of the eyes;
(l) visual fixation of the eyes at any given moment and
(m) nystagmus In an alternate embodiment to the configuration shown in step 1824 in FIG. 14, the visual target of interest can be dynamic and the head movement can also be dynamically moving in the same or opposite direction as the visual target movement. The process is repeated as many times as needed. This test can be conducted in the vertical, horizontal or any other direction.

Regarding the forward-facing camera, shown at 408 in FIG. 1, it should be noted that this scene camera or forward-facing camera 408 can be configured to record an image of what the user is seeing. Knowing where the subject is looking allows estimating the point-of-regard and overlapping it onto each video frame. In the embodiments discussed herein, the forward-facing camera 408, can be configured to determine, measure and log where the eyes of an individual, such as an athlete or military person, are looking during their play, occupational or military activities. This can be used to measure the duration of time an individual is visually focused on an object or target of interest. For example, this can measure if an athlete or military person can see an opponent or parts of an opponent (such as the hand or helmet) more quickly in time than others and how long the individual maintains focus on the visual object during the play or activity. This can be correlated with the eye tracking video camera 406, for measurement of accuracy and reaction times. Individuals with highly focused ability on the object of interest can more accurately anticipate and more precisely predict the movements of their opponents. This data can be used in training and/or the selection process of individuals prior to performing the activities needed.

Further referring to FIG. 1, the forward-facing camera 408, can be configured to adjust its field of view, focal length, or to zoom in or out in response to an eye sensor. The electronic module 410, using the central processing unit 418, could control the forward-facing camera 408. This control of the forward-facing camera 408, could be through wired or wireless electronic signals. The forward-facing camera 408, could transmit video information to the electronic module 410, and this video information could analog or digital information and could be transmitted through a wired or a wireless connection. The information collected and/or recorded by the forward-facing camera 408, can be responsive to the eye sensors 406, to measure ocular performance parameters. For VOR measurement, head rotation information would be measured using the head orientation sensor 404. The information collected and/or recorded by the forward-facing camera 408, could also be used, in conjunction with other information collected by the faceguard system, for capturing visual images of the user's surroundings, and determine the intended focal point of the use. As discussed previously, this determined intended focal point can be measured and correlated with the fixation accuracy of the eye tracking sensors. The user can also perform a predetermined action with the his/her eye(s) by focusing on a specific image or orienting the eye in a specific manner as an input control. Data collected can be uploaded and transmitted to a remote or external device.

In an embodiment the forward-facing camera can be configured for recording video images at a minimum of 24 frames per second. In another embodiment, the faceguard can be configured to have an attached visual cue projector, 430 in FIG. 1. This visual cue projector 430 can project a visual image or visual element, 434 in FIG. 1, in front of the user's visual field. The forward-visual cue projector 430 can be configured to project a stable image, for the user to focus upon, while the head is in motion and it can be configured to provide a moving image when the head is motionless. This visual cue projector 430 can be used for calibration purposes or projection of visual elements for testing the ocular parameters discussed herein and for visual rehabilitation following concussions/TBIs and the resulting cognitive deficits.

Embodiments of the faceguard invention(s) disclosed herein can be configured with a forward-facing camera to determine the point of fixation or gaze and can be integrated with an eye sensor configured for sensor fusion to enhance accuracy of gaze determination. The forward-facing camera can be configured for measuring and correcting slippage offsets as defined previously. This is done by coordinating the eye tracking camera and the head orientation sensor to calculate any slippage offsets and accurately determine point of visual fixation or the visual element(s) of eye fixation at a specific time and for a specific duration. To determine if the gaze position signal is affected by slippage during recordings, a validation at the end of recordings, and during testing can be done. To avoid further slippage-sensitive eye-tracking setups, all components (sensors and circuitry) should be evaluated, such as movement of the eye tracker or for VOR measurement, movement of the head orientation sensor. In these embodiments of the faceguard, sensors are configured for head orientation and eye muscle movement response measurements including but not limited to vestibulo-ocular reflex, pupillometry, saccades, vergence, dynamic visual acuity, eye-lid closure, focused position of the eyes, kinetic visual acuity, virtual retinal stability, retinal image stability, foveal fixation stability and nystagmus.

Embodiments of the faceguard invention can incorporate other impact mitigation elements and sensing elements/transducers for detecting any abnormal physiological or biochemical properties of the user.

In the embodiments disclosed herein, the forward-facing camera can be responsive to the eye sensors to measure the ocular performance described. It can visualize "world" objects in motion and then correlate these visual objects seen by the user with user eye movements. Measuring the visual object, the user is focusing upon, can be used to determine a prediction component of the user eye motion based on the visual target motion (e.g. Motion Tracking with Predictive Index Factor).

Sensors

Embodiments of the invention(s) disclosed herein utilize sensors. These sensors can also be referred to as sensing elements/transducers and/or transducers. In embodiments disclosed herein, these sensors can be used to detect and measure specific physical phenomena such as ocular performance and head orientation. There can also be sensors that measure physiologic, biochemical, and biometric values. The faceguard can incorporate sensors or sensing elements/transducers. The sensing elements/transducers could be attached or positioned to measure various properties of the faceguard. Sensing elements can deploy a response to input information. One example would be a pneumatic element (e.g. pneumatic/inflation bag, cushion or pad) from the faceguard, which can alter or change its characteristics prior to imminent impact. The sensing elements, sensors, or transducers can exhibit artificial intelligence in response to imminent blow information detected and the measured threshold values to determine the abnormal value necessary to elicit a response. These sensing elements/transducers on the faceguard can be self-altering, self-adjusting and can change the shape or characteristics of the faceguard elements before and after an impact to resume the pre-impact state. The sensing elements, sensors, or transducers can also allow observers to remotely check the status any of the sensing elements/transducers described and can change the parameters of the sensing element/transducer measurement or sensitivity if needed. Sensing elements/transducers on the faceguard can record information of how many times an impact has occurred to the faceguard and the force of the impact to the faceguard. Artificially intelligent sensing elements/transducers can also change a faceguard material characteristic shape and resistance, depending on the impending impact detected.

In another embodiment, the faceguard can be comprised of an impact sensor and an alarm, whereby the alarm is responsive to the impact sensor when an impact threshold has been reached. Whenever a critical impact has occurred the alarm will provide a signal indicating a need for evaluation of the affected athlete. This impact threshold can be a value to alert the user and others that testing of the user is required to determine if there is evidence of a concussion/TBI. The determined value may differ, based on age of the player, sex, ethnicity, location of the impact and other factors. For many athletes, impacts resulting in a linear head acceleration of 70 to 75 g may be sufficient to result in concussion. Therefore, the measured impact threshold for the sensor to elicit an alerting signal may be set at 75 g. Specific sensor location or placement can also be configured on the faceguard in one or more locations to detect both linear and rotational or tangential impacts. For example, in one embodiment an impact sensor responsive to linear impacts could be located in the center of the faceguard. An impact sensor responsive to rotational or tangential impacts could be located on the side of the faceguard structure. The accuracy of injury prediction improves with the addition of rotational and linear acceleration variables and the pre-set thresholds may be adjusted for different threshold. These sensors can be adjusted remotely. For example, impacts resulting in a rotational acceleration in excess of 5582 rad/s$^2$ can be associated with 1.9% chance of injury for impacts above this level. When resultant linear acceleration in excess of 96 g is included in the decision-making process, the possibility of a concussion increases to 6.9%.

These sensing elements/transducers can be pressure sensitive, ultrasonic, mechanic, electrical, electromagnetic, responsive to haptic, graphene, PVDF (polyvinylidene fluoride sensing, fluid-based sensing elements/transducers, microelectromechanical systems (MEMS)-based on accelerometers, silicon-based solid-state accelerometers, binary sensing elements of plastic housing and working fluids to detect instantaneous acceleration (impact).

In another embodiment, the abnormally measured physical, physiological and/or biochemical parameters can be wirelessly transmitted and displayed to an observer and/or provide a local, adjacent or remote response, alert or warning. This response to an abnormal value can be in the form of an optically perceptible response, such as photofluorescence, or can be a haptic, vibratory, or acoustical, either to the user and/or the device of the observer. For example, the faceguard or specific portion of the faceguard can change colors, emit a light, display or generate another signal response when an abnormal pre-determined impact threshold to the faceguard is reached, when abnormal oculomotor findings are measured and/or when an abnormal physiological or biochemical pre-determined value is measured.

In another embodiment sensing elements/transducers located on the faceguard can detect where the eyes are looking and focused, which can be correlated with a forward-facing camera and can log the data statistics on eye movements and point of fixation of the eyes at any given time. These sensing elements/transducers can be configured to measure human ocular performance of eye muscle movement responses including the vestibulo-ocular reflex, saccades, visual pursuit tracking, pupillometry, vergence, convergence, divergence, eye-lid closure, dynamic visual acuity, kinetic visual acuity, retinal image stability, foveal fixation stability, focused position of the eyes or visual fixation at any given moment and nystagmus. Sensor data acquired from the faceguard can be transmitted to a remote device such as smart watch, smart phone or tablet, Droid-type hand-held device or other electronic device.

In another embodiment, a sensor(s) attached to the faceguard can be configured for generating an alarm (output) signal in response to information received from the group of eye movement information, eye muscle movement response information and/or head movement information. For example, if an abnormal VOR is measured an alert signal can be generated. Similarly, if abnormal saccades, vergence or pupillometry parameters are detected, an alert signal can be generated. These alarm signals would be in response to any abnormally measured value from the eye sensor information for movements of rotation of a human eyeball, pupil size, eyelid movement and vision. The alarm or alert signal can be haptic, auditory, visual or it can be a wireless message to a remote electronic device.

In the embodiments discussed herein, the forward-facing camera, visual cue projector eye and head tracking sensors and components of the electronic circuit can be activated or controlled haptically, auditorily, remotely, wirelessly, with gestures or movement of the eyes, head, hands or manually with a power switch on the faceguard. Alternatively, the system can have a local/sideline mode (e.g. where the device remains on for testing while the player is off the field) and a field mode (e.g. where the device is listening for pre-define triggers alerts, at which time it will be turned on for measurement of ocular parameters).

Eye Tracking

To measure some specific eye responses (such as VOR, saccades, vergence or other ocular performance measures), both eye tracking and head tracking measurements are required. Eye tracking is the process of measuring either the point of gaze (where one is looking) or the motion of an eye relative to the head position. An eye tracker is a device for measuring eye positions and eye movement. Eye tracking and/or measurement can be done in many ways, examples of which include using a face guard as discussed herein, with eye sensors and a head orientation sensor and having the user look at a projected image in a natural environment;

The eye tracking and/or measurement can also be done:
  (a) in a non-contact fashion with the use of a light source (invisible light, such as with the use of an infra-red camera or light, or visible light); and
  (b) by using a video camera or other imaging sensor system designed to visually capture and record the eye movement activity.

If one or more video cameras are to be used for eye tracking, it is desirable to have a sampling rate at least 60 frames per second (60 Hz) and preferably at least 90-120 Hz. Many video-based eye trackers have sample rate of at least 30, 60, 120, 250, 350 or even 1000/1250 Hz. In embodiments of the present invention, eye tracking can use a sampling rate minimally of 60 Hz, but more typically at 120 Hz-350 Hz. These higher sampling rates may be needed in order to capture fixation of eye movements or correctly measure other saccade dynamics or capture the detail of the very rapid eye movement during reading, or during neurological evaluations, such as with concussions.

In embodiments of the invention, a light source can be used to illuminate the eye(s) and aid in eye tracking and/or measurement. The light source can be directed toward the eye or eyes and a camera tracks the reflection of the light source and visible ocular features such as the pupil features and/or cornea surface reflection(s). The information can then be analyzed to extract eye rotation and ultimately the direction of gaze from changes in reflections. Additional information such as blink frequency and changes in pupil diameter can also be detected by the eye sensor. The aggregated data can be stored and written to a file that is compatible with eye-tracking analysis software. Graphics can be generated to visualize such findings. Beyond the analysis of visual attention, stored eye data can be examined to measure the cognitive state, fatigue, alertness or other information.

As noted previously, a video camera or image sensor can be attached anywhere on or in the framework elements of the faceguard. The camera control unit can be activated by such options as: an auditory human input signal, a haptic human input signal, a digital auditory input signal, a digital haptic input signal, a manual input signal, human eye muscle movement or a human gesture. The control unit can also be timer actuated or triggered by an eye blink for a defined period of time.

The eye tracking and/or measuring system may include hardware such as an infrared camera and at least one infrared light source, a video tracking system and recorder or data logging unit. The infrared camera may be utilized by the eye tracking system to capture images of an eye of the wearer. The video images obtained by the infrared camera regarding the position of the eye of the wearer may help determine where the wearer may be looking within a field of view of the head mounted display used in the system. The infrared camera may include a visible light camera with sensing capabilities in the infrared wavelengths. Infrared light or radiation is a longer-wavelength radiation than visible light. It exists just outside of the spectrum of visible light. Heat, or thermal energy, is a common source of infrared light. An infrared camera is a device specially designed to detect and display the sources of this kind of light. A thermal infrared camera converts the heat detected into electrical signals, which are then projected in an image. Many types of night vision cameras are based on infrared light. A human body will always emit heat, and infrared cameras will detect this radiation.

The infrared light source can include one or more infrared light-emitting diodes or infrared laser diodes that may illuminate a viewing location, i.e. an eye of the wearer. Thus, one or both eyes of a wearer of the system may be illuminated by the infrared light source. The infrared light source may be positioned along an optical axis common to the infrared camera, and/or the infrared light source may be positioned elsewhere. The infrared light source may illuminate the viewing location continuously or may be turned on at discrete times.

In embodiments of the invention, a display device, such as a smart phone, can be mounted onto the faceguard and the optical system of the device can include components configured to provide images to an eye of the wearer. The components may include an attached display pane, a display light source which can display a visual element or scene capable of being stable or in motion and the image sensors and head tracking sensors attached to the faceguard can measure the ocular parameters discussed by observing the visual element or scene displayed. These components may be optically and/or electrically coupled or wirelessly connected to one another and may be configured to provide viewable images to the user's eye. One or two optical systems may be provided in the system.

Eye sensors which track different locations on the surface of one or both eyes or using multiple illumination sources and/or multiple cameras to generate and observe glint/reflections from multiple directions can be used to improve the accuracy of gaze tracking. One or more of the illumination sources can be comprised of infrared, near infrared or visible light, such as a micro-LED or micro-OLED projector. Eye sensors can be used to obtain anatomic structures and features of the eye, movements of the eye and eyelids, responses and reflexes of the eyes and eyelids. Eye tracking data can also be collected using a multi-camera eye gaze tracker, which is based on one-camera gaze estimation algorithm. Using an algorithm, the 3D eyeball position can be estimated by the two corneal surface reflections (or glints) of the IR lights. Each camera can estimate the gaze independently and can allow large head movement. The system can be accurate to less than 1 degree.

In an embodiment, the human ocular performance measuring system is comprised of eye sensors, attached to the faceguard unit, and configured to measure eye muscle movement responses using different techniques of eye sensor measurement including, but not limited to use of one or multiple cameras, or simultaneous use of different types of cameras for eye tracking. Alternatively, eye sensors can track of one or more different locations simultaneously on the surface of one or both eyes (e.g. cornea, pupil, limbus, sclera) or image features from the retina. In another embodiment, the eye sensor(s) measure more than one corneal reflection or other eye feature using one or more different types of illumination sources simultaneously. The different types of illumination sources can also alternate or combine the type of illumination, depending on the light needed. Positioning of the camera, or camera location which records the eye features is crucial and depends on light conditions and in another embodiment, the position of the eye cameras can change.

Eye sensor or image sensor data collection can be based on ambient/natural light, infrared, near infrared or non-traditional methods such as ultrasonic or by pulsed laser light. The software used to capture the data is often selected on the basis of the final image result needed or desired when viewing images in motion. One approach is the use of a global shutter which captures an entire frame all at once. Image sensors with a global shutter allow all of the pixels to accumulate a charge with the exposure starting and ending at the same time. At the end of the exposure time, the charge is read out simultaneously. In turn, the image has no motion blur on moving objects. A rolling shutter is much different and unlike a global shutter where the sensor is exposed all at once, a rolling shutter is exposed in a progressive motion. Image sensors with a rolling shutter do not expose all the pixels at the same time. Alternatively, they expose the pixels by row with each row having a different start and end time frame. The top row of the pixel array is the first to expose, reading out the pixel data followed by the 2nd, 3rd & 4th row and so on. Each of the rows, at the beginning and end point, have a delay as the sensor is fully read out. The result of this on moving objects is a skewed image.

In another embodiment, eye sensors, attached to the faceguard unit can be located in different positions to acquire different focal points of the eyeball, to achieve more accuracy with eye tracking. Eye sensors can also be configured to merge eye movement responses from different image sensors for more accurate measurement. For example, an eye sensor tracking the bright pupil can be merged with the same sensor, or another eye sensor, attached to different location on the faceguard, which is tracking the dark pupil response. In another example, an eye sensor tracking the dark pupil can be merged with the same or different sensor which is tracking the limbus. The merged data can provide more information regarding gaze and eye muscle movement responses. Eye sensors can have multiple functions which enable different measurement or features of the eyeball.

Eye tracking using binocular horizontal and vertical eye position estimates can be derived from the relative positions of multiple corneal reflections and the center of the pupil. By using two eye landmarks (corneal surface reflections and pupil center) whose relative position are invariant under translation, the angular position of the eye independently of lateral motion of the video system relative to the head is able to be estimated. The eye sensors used to measure different eye landmarks can be mounted on a faceguard in another embodiment.

In embodiments of the invention, the light source can be infrared, near infrared, and/or visible light, such as LED, can be directed toward one or both eyes and one eye could have one light source which is different than the light source directed toward the other eye. The camera can be used to track the reflection of the light source and visible ocular features such as the pupil features, cornea reflection features, iris registration features, limbus features or retinal data imaging. The collected data from the eye tracking system can be used to measure the muscle movement responses of the eyes or eyelids or rotation of the eyeball, acceleration/velocity of the eye movement, duration of the eyelid closure, rate of the eyelid closure and the direction of gaze. Additional information such as blink frequency and changes in pupil diameter can also be detected by the eye tracker. Aggregated eye tracker data can be written to a file for later analysis. Stored eye tracker data can be used to analyze the visual path across an interface such as a computer screen. In this case, each eye data observation is translated into a set of pixel coordinates. From there, the presence or absence of collected eye data points in different screen areas can be examined. This type of analysis is used to determine which features are seen, when a particular feature captures attention, how quickly the eye moves, what content is overlooked and virtually any other gaze-related data. Eye position is extracted from video images and graphics are often generated to visualize such findings. When using a video-based eye tracker, the camera can be focused on one or both eyes and used to record eye movement as a viewer looks at some type of stimulus.

The video camera or image sensor can be attached to the faceguard and positioned anywhere around the eye (e.g. under, above, or to the sides) or directly positioned in front of the eye, and directly in the visual field, depending on which eye movement characteristic is being measured. In an embodiment, at least one eye sensor is positioned below the inferior margin of the upper eyelid, in order to measure the characteristics of the eyeball. It is below the upper eyelid in order to more easily visualize the pupil, cornea, iris or other features of the eye used for eye tracking. In this position, the upper eyelid and eyelashes would not obstruct the eye muscle measurements related to the rotation of a human eyeball or vision and the visual measurements. It allows for unencumbered measures of the ocular parameters. Eye sensors above the inferior margin of the eyelid can measure eyelid movement, specifically eyelid muscle motion, movement above the levator muscle and behavioral feature characteristics.

When using an eye-tracking camera, two general types of eye tracking techniques can be used: Bright Pupil and Dark Pupil. The dark and bright pupil tracking techniques are based on the iris-pupil boundary detection. Light sources in the near IR spectrum are often used for these two approaches. The difference between these eye-tracking techniques is based on the location of the illumination source with respect to the optics. In the bright pupil approach, the infrared source is placed near the optical axis, while in dark pupil it is placed farther away from this axis. Therefore, in the bright pupil approach, the video camera records the infrared beam reflected by the subject's retina, making the pupil brighter than the iris, while in the dark pupil approach, the reflected infrared beam is not recorded by the camera and the pupil becomes darker than the iris. For the bright pupil approach, the infrared illumination is coaxial with the optical path and the eye acts as a retro-reflector as the light reflects off the retina creating a bright pupil effect similar to red eye. If the illumination source is offset from the optical path, as described for the dark pupil approach, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring. In the preferred embodiment, the system is configured to measure an eye parameter selected from the group of bright and dark pupil measurements. These tracking techniques can be use simultaneously or depending on the ambient light levels the techniques can alternate or alternatively, one eye may be tracked with one technique and the other eye can be tracked by the other technique.

Embodiments of the eye tracking system can track on the cornea or further in the eye, based on using light reflected by the eye. Whether using an external source or ambient light, some of the techniques for tracking the eye include not only pupil tracking, but also limbus tracking, Purkinje image tracking, corneal and pupil reflection relationship, corneal reflection and eye image using an artificial neural network.

Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still, or the apparatus must be fixed to the user's head. Due to the occasional covering of the top and bottom of the limbus by the eyelids, it is more helpful for precise horizontal tracking only.

Regarding pupil tracking, this technique is similar to limbus tracking. The difference is that in pupil tracking the smaller boundary between the pupil and the iris is used instead of the boundary between the white sclera and the dark iris. The advantages of this technique over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult. As noted previously, there are different illumination methods that can be used with pupil center corneal reflection eye tracking. Bright pupil eye tracking is achieved when an illuminator is placed close to the optical axis of the imaging device and dark pupil eye tracking occurs when an illuminator is placed away from the optical axis causing the pupil to appear darker than the iris.

Video-based eye trackers typically use the corneal reflection (the first Purkinje image) and the center of the pupil as features to track over time. A more sensitive type of eye tracker, the Dual-Purkinje eye tracker uses reflections from the front of the cornea (first Purkinje image) and the back of the lens (fourth Purkinje image) as features to track. A still more sensitive method of tracking is to image features from inside the eye, such as the retinal blood vessels, and follow these features as the eye rotates. Different factors can affect the pupil detection during eye tracking and eye trackers using multiple methods, such as dual-Purkinje or both bright and dark pupil methods can be more accurate in calculating the gaze position.

Other methods to track the eye are based on the visible images of a bright source that can be seen reflected from the structure of the eye. These images are called Purkinje images. The dark pupil/bright pupil techniques which were previously discussed can be used in combination with one of these methods, called the corneal reflection method. One type of video-based eye tracker tracks the reflection of the light on the outer surface of the cornea (first Purkinje image or often referred as glint) and the center of the pupil as features to track over time. The reflection appears as a very bright spot on the eye surface thus, it can be detected easily. Under some assumptions, the glint position depends only on head movement, thus the gaze can be estimated by the relative position between the glint and the pupil center. A more sensitive type of eye tracker, the dual-Purkinje eye tracker, uses reflections from the front of the cornea (first Purkinje image) and the back of the lens (fourth Purkinje image) as features to track. Dual Purkinje method is based on tracking both the first and the fourth Purkinje images. The fourth Purkinje image is formed by the light reflected from the rear surface of the crystalline lens and refracted by both cornea and lens itself. These two Purkinje images move together for pure translational movement but, once the eye undergoes rotation, their distance changes, giving a measure of the angular orientation of the eye. When light (such as infrared) shines into the user's eye, several reflections occur on the boundaries of the lens and cornea and is sensed by a video camera or eye sensor. These reflections or Purkinje images can then be measured and analyzed to extract eye rotation data from changes in reflections. In a preferred embodiment, the system is configured to measure an eye parameter selected from bright pupil/dark pupil measurements in combination with Purkinje measurements, including dual Purkinje and/or first Purkinje image measurements. In another embodiment, the system is configured to measure an eye parameter selected from Purkinje measurements, including dual Purkinje and/or first Purkinje image measurements.

Regarding pupil and pupil reflection relationship tracking, eye trackers can combine a camera with an infra-red light source that illuminates the eye with bursts of invisible infra-red light. Some of this infra-red light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infra-red light, which is picked up by the camera. By analyzing the reflections, it is then possible to determine where the eye is pointing. The technique is able to cope with blinking, head movements, dim light, glasses and contact lenses.

Regarding the use of artificial neural networks (ANNs) for computation, this is of the more recently developed techniques. The raw material for eye-gaze tracking is still a digitized video image of the user, but this technique is based on a more wide-angled image of the user, so that the entire head is in the field of view of the camera. A stationary light is placed in front of the user, and the system starts by finding the right eye of the user by searching the video image for the reflection of this light—the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil-based calculations can be augmented with a calculation based on the position of the glint in the eye socket. The advantage of ANN-based techniques is that due to the wide angle of the base image, user head mobility is increased.

Eye movement information from the eye tracker can be typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus are processed during an eye tracking session.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. Heat maps determine where an individual concentrated their gaze and how long they gazed at a given point. Saccade pathways trace the eye's movement between areas of focus. The movement is not unlike watching a hummingbird move between flowers—there are periods of attention and then rapid movement.

Another capability of the eye tracking technology is eye movement analysis, which can provide valuable insight into user's overt visual behavior and attention. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades (overt and covert), and smooth pursuits. Fixations are a result of one's desire to maintain gaze on a specific, stationary object. Smooth pursuits are similar except for the object of interest is in motion. Saccades represent a voluntary shift of focus from one fixation point to another.

Saccades can be detected and measured by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is often more widely used because it is more suitable for real-time applications.

Beyond the analysis of visual attention, eye data can be examined to measure fatigue, the cognitive state and workload of a person. Some techniques have been validated in multiple contexts as a reliable indicator of mental effort. Driving a car, reading a magazine, surfing the internet, searching the aisles of a grocery store, playing a video game, watching a movie or looking at pictures on your mobile device are such applications of eye tracking. With very few exceptions, anything with a visual component can be eye tracked.

In embodiments of the present invention, saccades can be tested by positioning two widely spaced targets in front of the person and asking the person to look back and forth between the targets. The technology used in faceguard can be used to calculate corrective saccades. This system for the person is configured to collect eye images of the person in excess of 60 Hz and configured to resolve eye movements smaller than at least 3 degrees of motion. Eye movement data can include at least one fixation target presented to the subject in a defined position and configured to yield a voluntary saccadic eye response from at least one eye of the person. The latency, amplitude, accuracy and velocity of each respective corrective saccade and latency totals and accuracy is calculated. This platform can calculate, and display secondary, and higher, corrective saccades. Calculating corrective saccade measurements from the eye data can include:

(a) the total number of corrective saccades associated with the subject's eye movement to each fixation;
(b) first corrective saccade latency;
(c) first corrective saccade amplitude;
(d) first corrective saccade accuracy;
(e) first corrective saccade velocity;
(f) ratio of first corrective saccade amplitude to main saccade amplitude associated with the subject's eye movement to each fixation target; and
(g) ratio of total of corrective saccade amplitudes to main saccade amplitude associated with the subject's eye movement to each fixation target presented to the subject.

The corrective saccade measurements can include measurements for a first corrective saccade and at least a second corrective saccade. The corrective saccade measurements for each corrective saccade can include the latency, amplitude, accuracy and velocity of each respective corrective saccade. During the initiation of a saccade, a high frame rate may be required for complete assessment.

Dynamic visual acuity (DVA), and retinal image stability (RIS), and foveal visual stability (FVS) testing can be used to determine the condition of a person's vestibulo-ocular reflex function. A DVA assessment can also include identifying a series of images or optotypes but with the addition of a head movement along an axis at a minimum rotational rate, engaging the vestibular system. The visualized images may also be dynamically moving in any direction, and can be random in position, appearance and presentation. Specifically, the image or visual element to be identified can be seen coming from any direction, randomly or with a specified pattern of motion, and may have different shapes, features, colors, sizes, orientation, patterns, or identifying characteristics, in a specific plane of axis or in variable plane, which the person must identify while the head in motion or rotating. The person can then provide feedback regarding what they see via an on-screen gesture, keyboard, smart device (e.g. defined as an electronic device, generally connected to other devices or networks via different wireless protocols such as Bluetooth, NFC, Wi-Fi, 3G/4G/5G cellular, etc., that can operate to some extent interactively and autonomously), eye or other physical response or by voice response. The comparison of the smallest image, visual image or optotypes correctly identified or the comparison of the correct numbers of images, visual elements or optotypes in both the DVA and SVA tests can determine if the person has a defect in his or her vestibulo-ocular reflex functions.

Faceguard embodiments of the present invention can have the advantage of measuring smooth pursuit (e.g. pursuit tracking during visual pursuit) in any plane, at various frequencies and in a variety of scan paths. As an example, eye tracking and visual or smooth pursuit can be done by visually observing a moving image traditionally in a horizontal or vertical plane or alternatively in a saw-tooth, sinusoidal, square-wave, snake-like, torsional, looped or other non-fixed plane of motion, which is more natural to what the normal person experiences in everyday life. Convergence movements can be evaluated by having the person fixate on an object as it is moved slowly towards a point right between the person's eyes. Vergence is an oculomotor function, described as disconjugate movement of the eyes to track images varying in depth over the binocular visual field and is commonly affected following concussions and mTBI. Embodiments of the present invention can measure this by presenting a visual object to the subject and detecting and measuring the position of the eyes and pupil area parameter. The visual object can move linearly or in sinusoid or another scan path toward and away from the subject at 0.1-2 Hz. The responses from both eyes are analyzed and compared to determine the coordination. In addition, the eyes can be observed and measured at rest to see if there are any abnormalities such as spontaneous nystagmus, disconjugate gaze (eyes not both fixated on the same point) or skew deviation (eyes move upward (hypertropia), but in opposite directions, all resulting in diplopia (double vision).

In embodiments of the present invention, pupillometry tests can easily be observed with the technology within the elements or attached to the faceguard elements. Pupil measurements can be calculated independently for each eye when visualizing an image stimulus and the responses can be compared. Pupil measurements can include: pupil diameter with visual stimulus and after stimulus, average pupil constriction velocity, average constriction latency, average pupil dilation velocity, maximum pupil constriction and dilation velocity, pupil constriction acceleration, and pupil dilation acceleration. The faceguard technology can allow the pupil to be measured on each side with variation of the levels of light. Both eye movement and peripheral vision testing can be measured. Eye movement testing can also be called extra-ocular muscle function or response as it represents testing or examination of the function of the eye muscles. These tests observe the movement of the eyes in six specific directions. Peripheral vision testing is also called visual field testing. Testing the visual fields consists of confrontation field testing, in which each eye is tested separately to assess the extent of the peripheral field. Target detail within the peripheral field-of-view can be altered without attracting attention. In a process known as "change blindness," it is also difficult to discern visual changes (that attract attention) if the changes are introduced slowly or at times when an observer is not looking.

In embodiments of the present invention, the eye or image sensor technology in the faceguard can be configured to:
 (a) collect eye images in excess of 90 Hz;
 (b) resolve eye movements smaller than at least 3 degrees of motion;
 (c) measure eye muscle movement responses, when a stimulus is presented to only one eye of the subject or both eyes;
 (d) yield a pupil movement response from at least one eye of the person;
 (e) measure pupils in each eye independently for the person's left and right eyes; and
 (f) compare pupillometry measurements for the left and right eyes.

Another embodiment involves dynamic control of the frame rate (i.e., number of images acquired per unit of time) of the one or more cameras that view regions of one or both eyes. Camera frame rate is a major determinant of the ability to determine and measure rates and directions of movement (i.e., velocities) of objects within images of an eye. The muscles within the eye are capable of movements that are most rapid of all muscle movements within the human body. Thus, increased camera frame rate can be critical in some cases to more accurately and robustly measure dynamic movements of an eye and/or its components. Modern cameras are capable of operating over a wide range of frame rates. Instantaneous frame rates can also be adjusted (i.e., governed by so-called "clock" circuitry) as frequently as on an image-by-image basis. Closely aligned with camera frame rate is the acquisition time required to collect each image. The maximum time a camera can take to acquire an image is the inverse of the frame rate (i.e., the total time of a frame=1/frame rate). However, modern-day digital cameras also have the ability to limit the time over which they detect photons during the image acquisition process. Limiting the time to acquire photons is known in the art as "electronic shuttering." Shuttering light (including infrared) collection times to very brief intervals (typically in the order of microseconds to milliseconds) "freezes" images, allowing a clearer view of moving objects since object edges are spread over fewer pixels. On the other hand, longer acquisition times allow the detection of more photons during each image, increasing the amplitude (i.e., intensity within each pixel) of camera images and generally increasing signal-to-noise ratios. Although micro-movements can be useful to infer some aspects of a user's status, they can interfere with directional and distance measurements of smooth pursuit and voluntary saccades. Higher frame rates allow algorithmic approaches to compensate for micro-movements by removing oscillations/movements at such frequencies or other mathematical approaches such as averaging results. Brief acquisition times can also be used to reduce image blur associated with micro-movements. The key to accurately determining initial saccadic direction and speed is the acquisition of camera images at high frame rates (typically hundreds of frames per second). Several techniques are available to acquire a rapid sequence of images immediately following a saccadic launch: 1) Once a saccadic launch is detected when sampling at a lower frame rate, the camera is immediately switched to a higher frame rate. 2) Camera circuitry (only) can be constantly run at a high frame rate, storing images within a circular buffer. Not all images are transferred out of the camera buffer and processed during normal operations. When a saccade is detected, rapidly sampled images that had been stored in the camera buffer can be retrieved for processing. 3) Frame rate can be adjusted based on the "context" of eye signal control. High frame rates can be maintained throughout these sequences.

Embodiments of the invention can use miniature video cameras. The image of the eye can be tracked and allow the person's horizontal, vertical, and/or torsional (rotary) vestibulo-ocular responses or other muscle movement responses to be measured. A moving visual target or visual element can provide a method for tracking, for optokinetic (OPK) testing, for saccade detection and measurement, for gaze fixation testing, for DVA measurement and for VOR testing. In the Active Head Rotation (AHR) horizontal test, the subject moves their head left and right randomly to the auditory signal and visual presentation. The speed of the signals increases through 1 Hz up to a maximum of at least 5-6 Hz. The person will attempt to keep moving the head back and forth at the speed of the cueing provided. For AHR Vertical, this test is conducted in the same manner as the horizontal test above, except that the head motion is up and down rather than left and right In further embodiments, the faceguard can include at least one, and typically two, digital, video or image sensor camera(s) trained on the person's eyes and which the camera can have auto-tracking. Each camera can be connected to and/or powered by a computer, such as through a "firewire" type connection. The computer may be a laptop portable computer or other digital device. The digital or other cameras may allow for digital centering of the person's pupil at least in one direction through concentrating on the region of interest, and can be in multiple directions. The use of digital centering eliminates the need for a mechanical adjustment mechanism in the given direction.

In another embodiment, the eye sensor can be further configured to capture a 3D image of the iris. In another embodiment, the eye sensor can be comprised of an array of transparent light detectors based on graphene. In another embodiment, the system can include an illuminator that is configured to provide illumination in a visible, LED or infrared light spectral band for the eye sensor to capture the 3D image of the iris. In further embodiments, the eye sensor can be a microlens array light field camera (LFC) or plenoptic camera.

In embodiments of the present invention, eye movements, muscle movement responses or reflexes and head movements can be detected and measured in a manner that is novel and unique compared to what has been done traditionally in the clinical laboratory. These faceguard embodiments enable a higher level of testing and measurement for these eye responses, particularly for the VOR, pursuit tracking, vergence, pupillometry and DVA. Embodiments of the present invention also provide unique methods to rehabilitate persons with vestibular system disorders, particularly those with peripheral vestibular disorders and especially those persons with vestibulo-ocular reflex abnormalities and/or abnormalities of ocular parameters discussed herein.

In another embodiment, the images or visual elements projected for the specific ocular parameter tests can be configured to a plurality of depth planes provided to an attached viewer on the faceguard display. The target image or visualized element may be different for each depth plane, which can provide a slightly different presentation of a scene or object. The target or visual element may be adaptively focused by each of the viewer's eyes, to provide depth cues based on the accommodation of the eye required to bring into focus different image features for the scene or visual element located on different depth planes and/or based on observing different image features on different depth planes being out of focus. These depth cues can provide credible perceptions of depth and add complexity to the testing and measurement.

Head Tracking

Head tracking on a faceguard can be performed by using an inertial sensing measurement unit (also called an IMU or 'tracker'). An IMU is an electronic device that measures one or more degrees of freedom (DOF), such as position, velocity, orientation, and/or gravitational force, as was described previously in this disclosure, by using one or more sensors. Sensors used in IMUs can include one or more accelerometers, gyroscopes, and magnetometers. A MEMS (microelectromechanical system) gyroscope, a MEMS accelerometer, and a MEMS magnetometer can be used as complementary and/or redundant sensor to accurately support a full range of motion in a three-dimensional space. Accelerometers work well for measuring five DOF: linear movements in three axes; and absolute tilt about the two axes perpendicular to gravity (i.e. pitch and roll). Accelerometers cannot easily measure rotation about an axis aligned with gravity (i.e. yaw). Magnetometers work well for measuring absolute yaw providing a sixth DOF. Gyroscopes provide a stable way to measure changes for the three rotational DOF (pitch, roll, and yaw). Devices that measure these three displacements and measure each of the three rotations in two different ways are typically called nine DOF IMUs. The input signals from the accelerometer(s), magnetometer(s), and gyroscope(s) in these nine DOF IMUS are often processed using a Kalman or a Madgwick filter located in a sensor pre-processing unit to provide output signals that have been optimized for accuracy, stability, and response rate.

The head tracking inertial system can be mounted in numerous configurations. Examples include: within a faceguard or attached to a faceguard Fourier Analysis A Fourier transform can be used to convert the relationship between an input (such as head motion) and an output (such as eye movement) in the time domain to a relationship in the frequency domain. By doing this, the ocular parameters discussed herein, can be measured for natural motion in a non-clinical environment. As described previously, one of the traditional ways of measuring VOR has been to oscillate a subject's head at a fixed frequency and then to measure how quickly the eyes respond. For this kind of testing, a frequency of 0.5 Hertz would correspond to one cycle every 2 seconds. A cycle corresponds to the combination of one movement to the right and one movement to the left. These movements are typically in the form of a sine wave. The gain at this frequency would be the amount of compensation that the eyes make to the movement of the head. A gain of −1 (also often written as a gain of 1) is perfect because the eyes have rotated exactly the same angle as the head, but in the opposite direction. A gain of −0.75 (often written as 0.75) means that the eyes only compensated for 75% of the head rotation. The phase or phase lag describes how much later the eyes moved than the head. A phase or phase lag of 0 would mean the eyes followed exactly. A phase or phase lag of 45 degrees at a frequency of 0.5 Hertz means that the eyes were delayed by $\frac{1}{8}^{th}$ of 2 seconds (or 250 milliseconds) because 45 degrees corresponds to $\frac{1}{8}$th of a full 360-degree cycle. To determine gain and phase at a variety of frequencies using the traditional approach of oscillating the head in a clinical environment, one would repeat the above test at a variety of frequencies and record the results. This method requires control over each input frequency and measuring the gain and phase of the eye response separately for each frequency, which will not work in a non-clinical setting having natural motion.

A time-varying signal (such as the natural motion of an object in one dimension) can be converted to a series of sine waves. This conversion from a time-varying signal to a series of sine waves is called a Fourier transform. Fourier transforms can be discrete or continuous. A continuous Fourier transform is one in which the time-varying signal is converted to an entire range of frequencies with no gaps between the frequencies. A discrete Fourier transform is one in which the time-varying signal is converted to a specific set of frequencies, such as the series 0.125 Hz, 0.25 Hz, 0.5 Hz, 1.0 Hz, and 2.0 Hz. Discrete Fourier transforms are easier to calculate using digital electronics. By converting the observed natural yaw of the head as a function of time using a Fourier transform, one can generate a graph showing the amplitude of the input signal that the eyes would need to compensate for in order to follow a stationary image or visual element. By converting the sensed horizontal movement of the eyes at this same time using a Fourier transform, one can generate a second graph showing the amplitude of the eye signal that compensates for the head movement. By comparing these two graphs mathematically, it is possible to determine gain at various frequencies directly from the natural head yaw movement. Similar mathematical calculations can be made to determine phase. The same method can be used to determine gain and phase in other dimensions such as pitch of the head versus the sensed vertical movement of the eyes, etc. Discrete Fourier transform calculations of this type can be performed by a microprocessor that receives the time-varying orientation signals from a head orientation sensor and the time-varying signals from an eye orientation sensor using mathematical calculations capable of being understood by anyone skilled in the art.

It should be noted that embodiments of the present invention can be implemented using dynamic analysis tools other than or in addition to Fourier Transform analysis, examples of which can include regression analysis, multi-variable regression, band pass filters, time domain analysis, Bode plots, Nyquist plots, waterfall diagrams, Campbell diagrams, resonance analysis, power spectral density analysis, frequency response function, coherence analysis, correlation analysis, cross power spectrum analysis, impulse response analysis, octave analysis, order analysis, waveform analysis, and/or any other dynamic system analysis tool capable of being understood by those skilled in the art.

Other Potential System Elements

In the preferred embodiment, the faceguard can be configured for eye tracking and measuring, head tracking, a power supply, a micro-processor, a memory, and a user interface. Components of the system can be configured to work in an interconnected fashion with each other and/or with other components coupled to respective systems. For example, the power supply can provide power to all the components of the system. The processor can receive information from the eye camera/image sensor signal processor, the head orientation signal processor, forward facing camera interface and any peripherals.

The system may include or be coupled to peripherals, such as a wireless communication interface, a touchpad, an integrated microphone, a high definition (HD) camera, electronic device and/or a speaker. A wireless communication interface may use 3G, 4G, 5G cellular communications, such as Code-division multiple access (CDMA), Evolution-Data Optimized (EVDO), Global System for Mobile communication (GSM)/General packet radio service (GPRS) communication or other cellular communications, such as Worldwide Interoperability for Microwave Access (WiMAX) or long term evolution (LTE). Alternatively, wireless communication interface may communicate with a wireless local area network (WLAN), for example, using Wi-Fi. In some examples, wireless communication interface may communicate directly with a device, for example, using an infrared link, Bluetooth, near field communication, or ZigBee. In addition, other wireless interface communication can be used with "off-the-grid" networks (such are FireChat) where there is not cellular phone service or internet connection.

The power supply may provide power to various components in the system and may include, for example, a rechargeable lithium-ion battery, solar power, mechanical power or various other power supply materials and types known in the art.

The processor may execute instructions stored in a non-transitory computer readable medium, such as the memory, to control functions of the system. Thus, the processor in combination with instructions stored in the memory may function as a controller of the system. For example, the processor may control the wireless communication interface and various other components of the system. In other examples, the processor may include a plurality of computing devices that may serve to control individual components or subsystems of the system. The processor, in conjunction with the memory unit, may perform analysis of the images obtained by the infrared camera.

In addition, the memory unit may store data that may include a set of calibrated wearer eye pupil positions and a collection of past eye pupil positions. Thus, the memory may function as a database of information related to gaze direction. Calibrated wearer eye pupil positions may include, for instance, information regarding extents or range of an eye pupil movement (right/left and upwards/downwards), and relative position of eyes of the wearer. For example, a relative position of a center and to one side with respect to a gaze direction or a gaze angle of the eye pupil of the wearer may be stored. Also, locations or coordinates of starting and ending points, or waypoints, of a path of a moving object displayed, or of a static path (e.g., semicircle, Z-shape etc.) may be stored on the memory unit.

The system may include the user interface for providing information to the wearer or receiving input from the wearer. The user interface may be associated with displayed images, a touchpad, a keypad, multiple cameras, buttons, a microphone, a haptic device, and/or other peripheral input devices. The processor may control functions of the system based on input received through the user interface. The system and/or testing function controls and input connections can be configured to be within or attached to the faceguard elements and/or in a remote electronic device. The faceguard technology system can be activated or controlled with methods including but not limited to a manual electronic keypad, voice activation, haptic movement, gestures, eyelid movement, ocular orientation, any body movement, visual input and with remote input signals. The computing system could be a distributed computing system. The computing system could comprise cloud computing.

One or more of the described functions or components of the system may be divided up into additional functional or physical components or combined into fewer functional or physical components. For example, the infrared camera may be mounted on the wearer separate from the system. Thus, the system may be part of a portable/wearable computing device in the form of separate devices that can be worn on or carried by the wearer. Separate components that make up the wearable computing device may be communicatively coupled in either a wired or a wireless fashion. In some further examples, additional functional and/or physical components may be added.

The system may be further configured to display images or visual elements to both eyes of the wearer Alternatively, the system may display images or elements to only one eye, either a left eye or a right eye.

The system may include a gyroscope, a global positioning system (GPS), magnetometer, and an accelerometer. The faceguard can be configured to provide information associated with a position and an orientation of the faceguard to the processor. The gyroscope may include a micro-electromechanical system (MEMS) gyroscope or a fiber optic gyroscope as examples. The gyroscope may be configured to provide orientation information to the processor. The GPS unit can include a receiver that obtains clock and other signals from GPS satellites. The GPS unit can be configured to provide real-time location information to the processor. The faceguard can further include an accelerometer configured to provide motion input data to the processor.

Additional Embodiments

In one embodiment, the device or method uses utilizes a faceguard with an eye-tracking and measuring sensor, a head motion sensor and compares the gain and phase of each (e.g. an electronic circuit generates a comparison of the three axes from the head orientation sensing element with eye movement signals from the eye sensor to calculate a gain and phase of the eye movement response to head rotation, in the opposite direction). The eye orientation sensor senses vertical movement and horizontal movement of at least one eye. The faceguard could be configured for a microphone for voice commands, and at least 12 GB of usable storage.

The faceguard can measure the relationship between motion of the head in this environment and vestibular ocular reflex. The data acquired can be uploaded to a remote position from the user for display and interpretation or transmitted wirelessly to a smart phone, wearable display device or other hand-held device, or another computer source. Under normal circumstances, when measuring the VOR and the user is looking at a visual element, the head turns in one direction and the eyes reflexively move in the opposite direction to maintain fixation on the visual element. The eye movement lags behind the head movement by 10 ms or less. Eye movement responses longer than this would be abnormal. The head orientation sensor can sense pitch and yaw of the person's head in a range of frequencies that comprises at least one frequency greater than 0.01 Hertz and less than 15 Hertz. The head orientation sensor can comprise an IMU. The head orientation sensor can comprise one or more accelerometer(s), magnetometer(s), and/or gyroscopes.

In one embodiment, a single camera system is used for the eye tracking. In another embodiment, a multi-camera system can be used and the cameras, attached to the framework elements, can be located in different sight planes or at different distances from the measured area of the eye or in a device attached to the faceguard, such as an iPhone or other electronic device. The camera control unit could be activated by a haptic human input signal, by an auditory human input signal, by a manual input signal, by a pre-set timer, by measured impact thresholds which reach or exceed those pre-set thresholds for concussions, and/or by an external wireless signal. The camera could have a resolution of at least five megapixels and could be capable of recording at 720p or 1080p resolutions. The camera could support Bluetooth and/or Wi-Fi. The camera could be part of, or work with an Android or iOS smartphone. The camera could have at least a 25° field of view. The camera system could also comprise an onboard OMAP (Open Multimedia Applications Platform) processor running the Android or iOS operating system. The entire camera system could be a smartphone mounted or attached to a faceguard, that includes an embedded eye camera sensor with a head motion sensor. Providing direct image overlay over the wearer's main line-of-sight, coupled with the motion sensors and camera, it can enable true augmented reality capability. A smartphone or similar device (such as a tablet computer) could also be used to provide wireless remote control.

In one embodiment, the eye-tracker uses the center of the pupil and infrared and/or near-infrared non-collimated light to create corneal reflections (CR). The vector between the pupil center and the corneal reflections can be used to compute the point of regard on surface or the gaze direction.

In an alternative embodiment of a binocular system, two mirror-image optical systems are mounted on each side of the faceguard frame. The corneal reflections are generated by illumination with two infrared LED's mounted to the faceguard frame. These LED's also serve to illuminate the pupil. The use of infrared (IR) light allows for invisible illumination of the eye. The use of multiple corneal reflections extends the linear range of the system by ensuring that one corneal reflection is always visible on the spherical surface of the cornea even with eccentric gaze. The images of the pupil and corneal reflections are reflected off of an IR mirror positioned in front of the subject's eye and directed to the cameras. This mirror is transparent to visible light and thus does not interfere with normal vision. The video image is sampled by a custom charge-coupled device (CCD) array that allows images to be sampled minimally at 20 Hz. Images from the CCD camera are processed in real time to obtain estimates of the corneal reflection and pupil center locations. Calibration of the eye tracker can be performed using a light source projected in front of the user, such as a laser pointer, or other detailed natural object and calibration procedure looking at multiple objects or points.

Testing of the VOR can also be tested with pitch and roll of the head tilt. Predictive tracking (e.g. algorithm which can predict the next head position and orientation can help computing and updating) can be used to prevent latency issues and lessen motion disturbances while being tested. A bone conducting sensor incorporated in the framework can provide haptic or auditory/acoustic signals to the user for cueing to rotate the head or performing other tasks. This data can then be stored, logged, interpreted and uploaded to a remote location. The eye tracking system can be used with or without a light source.

Trackers can constantly ping the sensors in the IMU to get information from them. The rate at which this happens is expressed as [samples] Hz (per second). The wearer of a head tracker may perform a gesture to indicate an attempt to unlock the head mounted camera display. For example, a gyroscope coupled to the faceguard may detect a head tilt, for example, and indicate that the wearer may be attempting to unlock the head mounted display screen.

In one embodiment the head tracker comprises an IMU, a battery and wireless interface charger, a wireless interfaced micro-controller, and a transceiver. The gyroscope in the IMU can be capable of sampling rates up to 760 Hz, and the transmitter link can have the throughput to transmit that fully under 1 ms latency to the remote station. Full positional updates (fused information from all the sensors) from the IMU can be sent at a rate of at least 500 Hz. The IMU comprises sensors that can sense roll, pitch, and yaw, as well as inertia when the IMU is moved forward/back, left/right, and up/down. The IMU could be a nine DOF IMU.

The mounted head tracker sensor in the head worn/eye worn device can include an IMU of any type cable of being understood by anyone skilled in the art. The mounting of the head tracker can be located anywhere to the faceguard and in any manner to the faceguard.

Another alternative embodiment of the invention is an inertial angular orientation tracking apparatus mounted to the faceguard. Drift sensitive sensors, such as angular rate sensors, produce a signal that is integrated to give a signal that represents angular position. The angular position signal may drift, due to integration of a bias or noise in the output of the rate sensors. To correct this drift, compensating sensors, such as gravimetric tilt sensors and geomagnetic heading sensor(s) can periodically measure the angular position, and this directly measured position signal is used to correct the drift of the integrated position signal. The direct angular position sensors cannot be used alone for dynamic applications because the gravitational sensors are also affected by non-gravitational accelerations, and therefore only accurately reflect angular position when under the influence of no non-gravitational accelerations. Typically, the drift sensitive sensors are angular rate sensors, (these include: rate gyroscopes and vibrating piezoelectric, magneto-hydrodynamic, optical and micro-machined silicon devices) the outputs from which are integrated once. However, other suitable drift sensitive sensors include linear accelerometers used to sense angular rate, gyroscopic angular position sensors and angular accelerometers. Typically, the compensating sensors are inclinometers, accelerometers and compasses.

In another embodiment, the faceguard can be configured to include a position tracker such as an acoustic position tracker, a system that tracks LEDs or IR position, optical sensors or reflective marks, a video machine-vision device, sensors integrated in the faceguard or a radio frequency position locating device.

In an alternative embodiment, the present invention not only measures the discussed ocular parameter, such as the VOR, but also rehabilitates/retrains the user when an abnormality is present, to enhance the VOR and/or visual accuracy with specific visual stimulation and head movements. This rehabilitation can be done for specific vestibulo-ocular pathologic findings. Specifically, when there is an abnormal VOR in the horizontal plane, specific algorithms of eye fixation on a target object, while the head is moving horizontally can be used to rehabilitate the abnormality. When the abnormal VOR is seen in the vertical plane, specific algorithms of eye fixation on a target object, while the head is moving in a vertical manner can be used to rehabilitate the abnormality. As the VOR is enhanced or improved, the DVA or RIS will be enhanced and cognition can be improved.

In one embodiment, the device or method could provide a sound signal and/or visual signal to alert or provide cueing to the user to respond by moving the eye or head for testing of an eye muscle movement response. Remote sensing, using an attached electronic device to the faceguard, such as a smart phone configured for eye and head tracking, can provide a visible target for testing eye movement characteristics in broad daylight are all features that can be incorporated in embodiments of the present technology. The faceguard system could also collect the data, which could then be uploaded to a medical doctor, trainer, coach or other person at a remote location. This remote location could then provide verbal or visual feedback to the user and this feedback could be integrated with other health status information provided to the user.

In one embodiment the device or method disclosed here can also be used to help a person improve his or her VOR and DVS and accuracy used during activities in daily living, routine exercise, and high level athletic/vocational activities. This can be used to help a person improve his or her balance by challenging, exercising, enhancing, and/or retraining the VOR (fixation/re-fixation) used during activities in daily living, routine exercise, and high level athletic/vocational activities and therefore improving the ability to remain fixed on the visual element or scene of interest. Thus, embodiments of the present invention can incorporate head movements in one or a number of planes as part of a systematic program for enhancing the VOR and DVA. Using the faceguard and methods described herein, it is possible for rehabilitation programs to incorporate head movement with stable image identification and image identification movement with the head remaining stable. The data obtained from the devices and methods described herein can be used for wireless communications. The data can be embedded GIS or geographic information system of the eyes or a digital map of where the eyes are located relative to the head movement.

In one embodiment, the device can be calibrated before it is used. When used in the laboratory setting, calibration can be performed by focusing on a distant target, such as a light bar or laser light which is projected to the wall. The image or visual element moves horizontally, vertically and then is center located. Typically, several trials are performed to establish reproducible results. During this test, the person is instructed to rotate the head from side to side horizontally or vertically to an auditory cue at frequencies ranging from 2 to 6 Hz. Eye movements are recorded including: direction, amplitude, and velocity of eye movements. Head inertial movements are recorded by the velocity rate sensor attached to the head. Tracking eye movement from spot to spot in this way is called "active tracking". When used in a non-laboratory or a non-clinical setting, similar testing can be performed if there are objects available to serve the same purpose as the distant target in the laboratory setting. Testing of this type allows gain, phase, and asymmetry to be measured separately at each frequency. A more sophisticated approach would be to ask the subject to follow an object that is not necessarily moving at one specific frequency, but at a combination of frequencies and then using a Fourier transform to convolve the gain, phase, and asymmetry at various frequencies directly from the complex waveform that was being followed by the subject.

As described in the previous paragraph, in some embodiments of the present invention, the head movement tracked and measured can be active. Another approach is to use and measure natural movement that normally occurs during normal activities or activities associated with a person's work and to compare that to the eye movement that occurs at the same time using a Fourier transform. This approach can be called "natural tracking" A third approach is to attach the head to something that then forces the head to move in a specific pattern—which is called "passive tracking."

In embodiments of the present invention, head movement testing can sense horizontal, vertical or torsional movements at various linear velocities, angular velocities, linear accelerations, angular accelerations, or frequencies. Natural test method testing in the horizontal plane could utilize focusing on a target moving across the horizontal visual field. Watching a moving object ascend and descend in the air can serve as a natural vertical test.

Any combination of the discussed embodiments of head inertial trackers and eye tracking systems can be used to measure the ocular response (e.g. VOR) with head movement. If active tracking is used, the user visualizes a target of interest while moving the head. As the head moves, the ocular responses can be tracked and measured by a variety of modalities. A Fourier transform or other method of analysis can be used to compare the inertial head movement and eye muscle movement response at various frequencies in a complex waveform and software can analyze the data. The stored data can be displayed remotely and abnormalities of the related ocular response to the head movement can then predict the performance of the user when performing an occupational activity.

In the prior art, clinicians have looked at the VOR response and made a binary judgment (e.g. the VOR was abnormal or normal). This normal/abnormal criterion would then be used to determine whether vestibular rehabilitation was needed. A better method for evaluating the VOR response would be to measure vestibulo-ocular performance on a continuous scale, just like we measure the speed of an athlete. By doing this, one can get a subject's human performance measurement. Specifically, there can be a VOR response score that more clearly establishes the vestibulo-ocular response measurement and expresses this response measurement in language that can more appropriately be applied to human performance measurement and improvement. Establishing such a scoring system will enable people to more accurately predict human performance with specific activities. It may also help in the development of activities that improve the human performance in fields where above average vestibular ocular performance is of benefit. The same use of scoring on a continuous scale and multi-frequency composite scoring can apply to DVA, DVS and RIS.

Areas of Application

Embodiments of the systems and methods described herein could be used in a variety of areas, including but not limited to the military, sports, medical, and commercial businesses. In the tests described herein, all oculomotor responses can be measured in a faceguard. Eye features and movements, as well as eyelid, and head movements can be tracked. Eye muscle movement responses, eye position, fixation ability, visual acuity, pupil function, vergence and cognition can all be easily measured with this technology in the faceguard. These eye parameters can be correlated with movement of the extremities to assess hand eye coordination. The faceguard can be attached to a helmet and used for protection of at least part of the face when participating in potential physical contact activities including but not limited to football, lacrosse, hockey, horse-back riding, cycling, motor-cross, whitewater, climbing, baseball, construction or industrial applications and in helmets used by security and/or military forces.

Sports.

Embodiments of the present invention, using ocular performance measurements, can be used in sports/athletic environments where ocular parameter measurement can help predict player performance, player fatigue and early detection of abnormalities such as concussions and traumatic brain injury. For example, if a player has an abnormal VOR/DVA in the horizontal plane, that person may not be able to catch a ball when competing in athletic activities that require the head to rotate in a horizontal plane. Similarly, if a player has a vertical VOR/DVA abnormality and is running downfield while looking upwards over the shoulder, the ball will not be in focus. Specifically, the retinal visual stability and accuracy would be diminished. In this instance, there would a higher likelihood of dropping the ball compared to another athlete who has normal VOR responses with normal DVA. If a VOR abnormality was determined to be present prior to play, which could result in difficulty with foveal fixation, and athlete could undergo VOR retraining to rectify the abnormality and therefore improve play performance. Alternatively, the coaching staff could select another athlete who did not have this abnormality. For example, on game day if a football player had an abnormal VOR, with resultant decline in the DVA, in the vertical plane (e.g. lack of visual fixation on an object of interest with upwards and downwards movement of the head), then it can be predicted that the athlete is not likely to catch a ball while running downfield and looking upwards over the shoulder (e.g. you cannot catch, what you cannot accurately see). This would offer some value to the coaching staff in selecting plays for the player based on his/her predicted performance. Additionally, if an athlete had such an abnormality and could be given some rehabilitation methods prior to play, this could correct the abnormality and increase performance in that activity. Athletes who have had concussions or TBI can have a vestibular ocular performance (VOP) abnormality, with resultant decrements in the VOR, DVA, or RIS. Embodiments of the present invention can be an accurate method to determine when the athlete is ready to return to play activities, based on improvement of the VOR or DVA. It therefore can be utilized in TBI/concussion evaluation/assessment and management for return to play. It is also intended for athletes who wish to enhance their training and athletic/vocational performance. It can be used in fitness centers, sports training centers, athletic performance centers, and vocational performance centers. Some ocular performance measurements, including VOR, can also be adversely affected by alcohol and drug use. Potential use of this testing can also provide a drug screen for those individuals suspected of having suboptimal performance. Playing at higher performance levels demands excellent eye fixation on the visual target of interest while they are in motion. If athletes wanted to perform at a higher level, it could change the culture of adverse behavior activities, knowing that these activities would have a negative effect on their performance by having poor visual fixation while doing the activity they enjoy.

Military personnel functioning in a high-level environment and requiring target fixation of their eyes, while performing other activities such as with head or body movement, require a normal VOR and normal DVA. If the VOR/DVA is abnormal, the individual will not demonstrate peak human performance. Embodiments of the present invention can be used by the military in places such as the pilot selection process or special operations community to aid in the selection of individuals without a VOR/DVA abnormality. VOP measurement could enable other individuals, who had normal foveal fixation ability to be chosen for a particular task that has better predictable performance for a particular duty of the day. Like that discussed above with athletes, ocular performance measurements, including visual pursuit tracking and VOR, can be adversely affected by alcohol and drug use. This testing can provide evidence of military personnel suspected of having potential of suboptimal performance before performing specific duties requiring high performance with eye fixation.

Medical.

Similarly, any person with a motion sensitivity disorder (such as motion sickness, vection induced motion sickness, or visually induced motion sickness) or a balance problem, either of a central or peripheral origin, will have a VOR/DVA abnormality. Individuals with such an abnormality will express symptoms of dizziness, disorientation, difficulty with focusing, nausea, fuzziness, and such other complaints as not being clear headed. Embodiments of the present invention can be useful to people who have experienced a vestibular insult, vestibular dysfunction or labyrinthine dysfunction such as those caused by infection, concussive injury, traumatic brain injury, vascular disease, ototoxic or vestibulotoxic medication use, surgical complications, Meniere's disease, people experiencing chronic imbalance, such as, but not limited to, stroke victims, people with systemic illnesses, the elderly and other people who have experienced head injuries, especially those who have experienced cerebral or labyrinthine (inner ear) concussions. It also can be utilized other centers which perform vestibular rehabilitation and athletic/vocational enhancement environments. This ocular performance measurement method using a faceguard, can be used as an objective tool for assisting in the diagnosis of traumatic brain injury (TBI), concussion and other degenerative cerebellar disorders that cause highly abnormal results.

Vestibular Rehabilitation. VOR scoring can also be beneficial in determining who is likely to benefit with vestibular rehabilitation therapy. VOR scoring can also be used more objectively in determining the benefit or improvement with such therapy. The system can include improvement information that can be used by the user, a coach, a medical practitioner, or any other advisor to help interpret the scoring and provide advice and/or exercises to improve ocular reflex. Although vestibular rehabilitation therapy can improve the ocular responses, this scoring can accurately quantify the improvement and more ably predict who is able to return to their normal activity without loss of human performance. Having a VOP score can also provide feedback that helps to control abnormal VOR responses. When an ocular response is abnormal with head rotation (a VOR abnormality, for example), such a finding can also determine a need for improvement with rehabilitation. Repetitive head movement in the abnormal plane of rotation, while the eye remains fixed on a target of interest, can provide a means for improving or enhancing the VOR or other eye responses. Specifically, if a VOR abnormality is found to exist in the horizontal plane, VOR enhancement rehabilitation therapy is given in the same plane. In this instance, the user focuses on a target of interest and the user rotates the head horizontally, while continuing to look at the target. If a VOR abnormality is found to exist in the vertical plane, VOR enhancement rehabilitation therapy is also given in the similar plane of the abnormality. In this instance, the user focuses on a target of interest and the user rotates the head vertically, while continuing to look at the target. The head speed can be varied and the target, which the user is focused, can be changed. The process can be repeated as often as necessary until the VOR abnormality is corrected. This therapy can be performed in any plane where such an abnormality exists. The same use of scoring on a continuous scale and multi-frequency composite scoring can apply to DVA, DVS and RIS.

Embodiments of the inventions described herein can provide supernormal enhancement of these same systems where no balance disorder exists, as in the case for enhancement of athletic and vocational abilities. Embodiments can enable individuals to reach a higher level of performance in their occupation, enable them to have increased ocular performance functions when participating in their usual occupational or play activities as well as enabling cognitive training and rehabilitation. Such an enhancement methodology can be used in athletic/vocational enhancement or training.

Further Embodiments of the Invention

In another embodiment, an interactive ocular parameter program can be provided that uses image-based interactivities for testing and management of concussions/traumatic brain injury with periodic assessment to analyze the progress of cognitive deficits. A cognitive rehabilitative program can be used with specific identified cognitive conditions. The cognitive testing can also be used for assessing the neurologic status, alertness, fatigability, return to play readiness, situational awareness, unhealthy status, predicting human performance, stress and managing any deficits detected with a visually interactive cognitive program designed to correct those deficits.

In another embodiment, this faceguard technology can be used in gaming activities where multi-use players rely on observed measured visual accuracy of ocular parameters to compete against each other.

In another embodiment, a hand-held device, configured to measure any of the ocular parameters described herein, can be attached to a faceguard and can transmit the measured data to a remote electronic device and to the user. The hand-held device, such as a smart phone, iPad, or other specifically configured electronic device for measuring specific ocular parameters, can measure these responses using 2-D, 3-D, virtual reality or augmented reality system methods of display.

Collection of different imaging characteristics of the eye(s) can provide better tracking ability of the eye movements. In another embodiment, one eye sensor within or attached to the faceguard structural member, collects images of at least one part the eye(s) of a user and the same sensor collects images of different part of the eye(s). Alternatively, one sensor, within the faceguard structural member can collect images of at least one part of the eye(s) and another sensor, within the faceguard structural member having a slightly different focal length, can collect images of at least the same part, or of another part of the eye(s). Collection of different imaging characteristics of the eye(s) can provide better tracking ability of the eye movements.

In another embodiment, the eye sensor attached to the faceguard is an imaging sensor or image sensor. Since the images received are at a minimum of 90 frames per second, the imaging sensor is not receiving a stream of video, but rather is capturing single frames from the sensor and processing them single images. The imaging sensor type can include, but is not limited to infra-red, near infra-red, non-visual light, visible light, lidar, ultrasound and or combinations of different types.

In one embodiment, the present invention is comprised of an ocular performance measuring system with head tracking and ocular-based sensors integrated into a face guard. The system described is configured for measuring eye muscle movement responses and is comprised of at least one eye sensor, a head orientation sensor and electronic circuit. This system is responsive to a human generated input signal from the group of but not limited to an auditory human input signal, a haptic human input signal, a manual input signal. Alternatively, the system or other configured components can also be responsive to input signals including a remote input signal, accelerometer-based measures with pre-set impact thresholds, a digital auditory input signal, a digital haptic input signal, human eye muscle movement or a human gesture. As an example, eyelid closure, for a defined time, could also trigger the forward-facing camera. An algorithm measuring blinking time and duration to discriminate between voluntary and involuntary eye blinks could be used to issue an input signal to a controller to operate the camera system. The controller could communicate with other parts of the system to support the commands.

In another embodiment—there can be different modes of detection or types of input signals. For an on the field mode, this input control can be designed for use on the field of play. In this mode, testing is activated using 'triggers' such as impact acceleration event using pre-determined level and based on random timers. In another mode, the sideline modem, designed for testing and diagnostics, the testing can always be on the tracking loop with a 'look back trigger' for certain event thresholds which were measured. Embodiments can also have a USB-mini connection to facilitate data transfer.

In another embodiment, two or more image sensors are configured in a complementary fashion to increase sensor accuracy. Image sensors can be configured from the following group: image sensors of the same type across different focal lengths, image sensors of the same type across different angular locations and/or image sensors of differing types to provide composite images.

In an embodiment, the faceguard is attached to the helmet and has an aperture allowing the user to visualize the surrounding environment or scene. For some users, this aperture may be comprised of more structural elements for facial protection, dependent on the player position. Other players may have less structural elements protecting the face if more visualization is preferred. The structural elements can be configured to provide an aperture for unobstructed viewing of the surrounding scene. The aperture is configured to provide at least 10 degrees of viewing in all directions from a midpoint of the visual plane, when looking outward into the visual scene. The structural elements can be rigid to protect the face and others may have some flexibility to help mitigate the impacts to the facial structure and head.

Although the faceguard should be firmly coupled to the helmet, the faceguard can be configured to have an adjustable interface, positioned between the faceguard and helmet. This would allow the faceguard to be used with different helmets.

In another application embodiment, the faceguard system can be used for gambling sports, fantasy football as well as other fantasy sports. The ocular performance measures discussed herein can provide information about player's health condition, including concussion, traumatic brain injury, neurologic status, cognition, fatigue, alertness, impairments and/or oculomotor parameter measurements to participants viewing the data transmitted. Information acquired from the faceguard system can be transmitted to a mobile device, computer, or other electronic device in a variety of communication methods including a dedicated SMS text service. Users of the devices can track athlete injuries, measure and/or predict human performance of the athlete or team using the faceguard system. This data received can be used for draft assistance, measurement of play performance, predictions, injury assessments and as a measure for duration of play.

In another embodiment, an interactive ocular parameter program can be provided that uses image-based interactivities for testing and management of concussions/traumatic brain injury with periodic assessment to analyze the progress of cognitive deficits. A cognitive rehabilitative program can be used with specific identified cognitive conditions. The cognitive testing can also be used for assessing the neurologic status, alertness, fatigability, deployment readiness, situational awareness, unhealthy status, predicting human performance, stress and managing any deficits detected with a visually interactive cognitive program designed to correct those deficits.

In another embodiment, the faceguard system can be integrated with wireless systems and software, allowing the collection and analyzing of real-world eye tracking data from athletes on the field playing a sport. Mobile data logging allows the physiology data to be collected. Eye tracking metrics can also include gaze path, pupil diameter, blink frequency, heat map, areas of interest (AOI), moving areas of interest, fixations, fixations sequence, and dwells.

In another embodiment, the eye sensor can measure the pupil size; pupil muscle movement, pupil movement velocity changes and/or duration of pupil changes. These characteristics can be used to measure the health status related to a concussion, traumatic brain injury, neurologic status and neurologic disorders, cognition, mental activity, alertness, fatigue, impairment due to drugs and alcohol and vision impairment. It also can measure evidence of hearing loss, human behavior and situational awareness.

Although the invention herein has been described with reference to particular embodiments, it is to be understood that these embodiments are merely illustrative of the principles and applications of the present invention. For example, the present invention may be used to protect workers in an industrial setting, at a construction site, etc. In order to accomplish this, the device of the present invention may, for example, be attached to construction helmets. It is therefore to be understood that numerous modifications may be made to the illustrative embodiments and that other arrangements may be devised without departing from the spirit and scope of the present invention as defined by the appended claims.

A number of variations and modifications of the disclosed embodiments can also be used. The principles described here can also be used for applications other than sports. While the principles of the disclosure have been described above in connection with specific apparatuses and methods, it is to be clearly understood that this description is made only by way of example and not as limitation on the scope of the disclosure.

What is claimed is:

1. A faceguard wherein:
    the faceguard is configured for measuring an eye movement;
    the faceguard comprises:
        a structural member configured for protecting at least one part of a human face;
        at least one aperture configured for human vision through the faceguard;
        an eye sensor wherein:
            the eye sensor comprises an imaging sensor; and
            the eye sensor senses eye information selected from the group of:
                eye movement;
                pupil movement; and
                eyelid movement;
        a head orientation sensor wherein:
            the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
        an electronic circuit wherein:
            the electronic circuit comprises a central processing unit, and a memory unit;
            the electronic circuit is responsive to the eye information received from the eye sensor; and
            the electronic circuit is responsive to the head movement information received from the head orientation sensor.

2. The faceguard of claim 1 wherein:
    the faceguard is configured for attachment to a helmet wherein the helmet is configured for being worn by a human.

3. The faceguard of claim 1 wherein:
the faceguard is configured for measuring a human health condition selected from the group of:
a concussion; and
a traumatic brain injury.

4. The faceguard of claim 1 wherein:
the imaging sensor is below the inferior margin of the upper eyelid.

5. The faceguard of claim 1 wherein:
the faceguard further comprises an impact sensor and an alarm wherein the alarm is responsive to the impact sensor when an impact threshold has been reached.

6. The faceguard of claim 1 wherein:
the electronic circuit further comprises a communication unit; and
the communication unit is configured for wireless transmission of information selected from the group of:
the eye information;
the head movement information; and
the measured eye movement response.

7. The faceguard of claim 1 wherein:
the electronic circuit is configured for generating an alarm signal in response to information selected from the group of:
the eye information;
the head movement information; and
the measured eye movement response.

8. The faceguard of claim 1 wherein:
the faceguard is configured for measuring and correcting slippage offsets between the faceguard and a helmet.

9. The faceguard of claim 1 wherein:
the faceguard further comprises a forward-facing camera configured for recording video images at a minimum of 24 frames per second.

10. The faceguard of claim 1 wherein:
the imaging sensor comprises a video camera configured for receiving images at a minimum of 90 frames per second.

11. The faceguard of claim 1 wherein:
the faceguard further comprises a forward-pointing visual cue projector.

12. The faceguard of claim 1 wherein:
the head orientation sensor comprises a micro-electro-mechanical system integrated circuit comprising a module selected from the group consisting of an accelerometer, a magnetometer, and a gyroscope.

13. A human ocular performance measuring system wherein:
the system is configured for measuring an eye movement;
the system comprises:
an eye imaging sensor wherein:
the eye imaging sensor is affixed to a faceguard wherein the faceguard comprises:
a structural member configured for protecting at least one part of a human face; and
at least one aperture configured for human vision through the faceguard; and
the eye imaging sensor senses eye movement information selected from the group of:
horizontal eye movement;
vertical eye movement;
pupil movement; and
eyelid movement;
a head orientation sensor wherein:
the head orientation sensor is affixed to the faceguard;
the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
an electronic circuit wherein:
the electronic circuit comprises a central processing unit, and a memory unit;
the electronic circuit is responsive to the eye movement information received from the eye sensor; and
the electronic circuit is responsive to head movement information received from the head orientation sensor.

14. The human ocular performance measurement system of claim 13 wherein:
the system is responsive to a human generated input signal selected from the group of:
an auditory human input signal;
a haptic human input signal.

15. A method for measuring human ocular performance comprising the steps of:
establishing a faceguard that comprises:
a structural member configured for protecting at least one part of a human face, and at least one aperture configured for allowing human vision through the faceguard;
an eye sensor configured for sensing
eye movement information selected from the group of:
horizontal eye movement;
vertical eye movement;
pupil movement; and
eyelid movement;
a head orientation sensor configured for sensing a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
using an electronic circuit to:
receive eye movement information from the eye sensor;
receive head movement information from the head orientation sensor.

16. The faceguard of claim 1 wherein:
the faceguard is configured for measuring an ocular parameter from the group of:
vestibular ocular reflex;
smooth pursuit;
saccades; and
vergence.

17. The faceguard of claim 1 wherein:
the faceguard is configured for measuring visual pursuit wherein visual pursuit comprises:
measurement of eye movement while the eyes follow a moving visual element and the head remains motionless; followed by measurement of head and eye movement while the head is moving in the same direction as the moving visual element.

18. The faceguard of claim 1 wherein:
the faceguard is configured for detecting a cognitive deficit.

19. The faceguard of claim 1 wherein:
the faceguard is configured for detecting and measuring corrective saccade information from the group of:
the number of saccades associated with a person's eye movement to a fixation point;
a corrective saccade latency;
a corrective saccade amplitude;
a corrective saccade accuracy; and
a corrective saccade velocity.

20. The human ocular performance measurement system of claim 13 wherein:
the system is used to predict human performance in a setting selected from the group of:
an occupational activity;
a sports activity; and
a military activity.

\* \* \* \* \*